US012600705B2

(12) United States Patent
Wipf et al.

(10) Patent No.: US 12,600,705 B2
(45) Date of Patent: Apr. 14, 2026

(54) HEAT SHOCK PROTEIN MODULATORS AND ANTI-HUNTINGTON DISEASE THERAPEUTIC AGENTS

(71) Applicant: UNIVERSITY OF PITTSBURGH-OF THE COMMONWEALTH SYSTEM OF HIGHER EDUCATION, Pittsburgh, PA (US)

(72) Inventors: Peter Wipf, Pittsburgh, PA (US); Linh Khai Ngo, Pittsburgh, PA (US); Leila Terrab, Pittsburgh, PA (US); Jeffrey L. Brodsky, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 734 days.

(21) Appl. No.: 17/798,699

(22) PCT Filed: Feb. 12, 2021

(86) PCT No.: PCT/US2021/017890
§ 371 (c)(1),
(2) Date: Aug. 10, 2022

(87) PCT Pub. No.: WO2021/163513
PCT Pub. Date: Aug. 19, 2021

(65) Prior Publication Data

US 2023/0131668 A1 Apr. 27, 2023

Related U.S. Application Data

(60) Provisional application No. 62/976,838, filed on Feb. 14, 2020.

(51) Int. Cl.
*C07D 285/16* (2006.01)
*C07D 417/12* (2006.01)
*C07D 513/18* (2006.01)

(52) U.S. Cl.
CPC ......... *C07D 285/16* (2013.01); *C07D 417/12* (2013.01); *C07D 513/18* (2013.01)

(58) Field of Classification Search
CPC .................................................... C07D 285/16
See application file for complete search history.

(56) References Cited

U.S. PATENT DOCUMENTS 3,203,954 A 8/1965 Wright
5,411,955 A * 5/1995 Strasser .................. A61P 25/04 514/210.16
2017/0266263 A1 9/2017 Jensen et al.

FOREIGN PATENT DOCUMENTS

WO 2007/054601 A1 5/2007
WO 2020012423 A1 1/2020

OTHER PUBLICATIONS

Lee et al., Bull, Korean Chem. Soc. (1992), vol. 14(5) pp. 453-454.*
Extended European Search Report dated Feb. 1, 2024 in EP Application 21754284.4 (11 pages).
Wisen et al. "Chemical modulators of heat shock protein 70 (Hsp70) by sequential, microwave-accelerated reactions on solid phase," Bioorganic & Medicinal Chemistry Letters, 2007, 18(1), 60-65.
Lawson A. et al. Chemistry of Thiadiazole and Thiadiazine S-Oxides. Chem. Rev. 1970, 70, 593-618.
Petersen, H. Syntheses of Cyclic Ureas by a-Ureidoalkylation. Synthesis 1973, 243-292.
McDermott SD et al. Synthesis and Reactions of Sulfamides. A Review. Org. Prep. Proced. Int. 1984, 16, 49-77.
Gazieva GA et al. Sulfamides in the Synthesis of Heterocyclic Compounds. Russ. Chem. Rev. 2000, 69, 221-230.
Lee CH et al. Functionalized 5,6-Dihydro-2H-1,2,6-Thiadiazine 1,1-Dioxides. Synthesis, Structure and Chemistry. J. Heterocycl. Chem. 1990, 27, 2107-2111.
Lee CH et al. Synthesis of 4-Carbethoxy-5-Aryl-5,6-Dihydro-2H-1,2,6-Thiadiazine 1,1-Dioxides. Bull. Korean Chem. Soc. 1992, 13, 462-463.
Maskrey TS et al. A Five-Component Biginelli-Diels-Alder Cascade Reaction. Front. Chem. 2018, 6, 376.
Huryn DM et al. Chemical Methodology as a Source of Small-Molecule Checkpoint Inhibitors and Heat Shock Protein 70 (Hsp70) Modulators. Proc. Natl. Acad. Sci. U. S. A. 2011, 108, 6757-6762.
Goya P et al. Regioselective N-Alkylation of 1,2,6-Thiadiazine 1,1-Dioxide Derivatives. J. Heterocycl. Chem. 1981, 18, 459-462.
Goya P et al. Synthesis of 4-Substituted 3-Hydroxy- and 3-Amino-6H-1,2,6-Thiadiazine 1,1-Dioxides. J. Heterocycl. Chem. 1978, 15, 253-256.
Dusemund J. Reaction of Sulfamide with Aldehydes and Acetals. Arch. Pharm. 1974, 307, 881-883.
Lee CH et al. 3,7-Bis(Carboethoxy)Perhydro-1,5,2,4,6,8-Dithiatetrazocine 1,1,5,5-Tetroxide. Synthesis, Structure and Chemistry. Heterocycles 1988, 27, 2581-2588.
Lee CH et al. Intra- and Intermolecular a-Sulfamidoalkylation Reactions. J. Org. Chem. 1990, 55, 6098-6104.
Cava MP et al. Synthesis of Caseadine Methyl Ether. J. Org. Chem. 1969, 34, 2665- 2667.
Mitsunobu O et al. Preparation of Esters of Carboxylic and Phosphoric Acid Via Quaternary Phosphonium Salts. Bull. Chem. Soc. Jpn. 1967, 40, 2380-2382.
Shioiri T et al. Diphenylphosphoryl Azide: A New Convenient Reagent for a Modified Curtius Reaction and for the Peptide Synthesis. J. Am. Chem. Soc. 1972, 94, 6203-6205.
Chiang AN et al. Synthesis and Evaluation of Esterified Hsp70 Agonists in Cellular Models of Protein Aggregation and Folding. Bioorg. Med. Chem. 2019, 27, 79-91.

(Continued)

*Primary Examiner* — Paul V Ward
(74) *Attorney, Agent, or Firm* — Meunier Carlin & Curfman LLC

(57) ABSTRACT

Disclosed are thiadiazine compounds, derivatives and compositions thereof. The compounds, derivatives, and compositions can be used for treating or preventing a heat-shock protein responsive disorder or suppressing protein aggregation in a subject. The compounds and compositions can also be used for treating cancer, neurodegenerative disorders, and other heat-shock protein responsive disorders.

13 Claims, 11 Drawing Sheets

(56) References Cited

OTHER PUBLICATIONS

Kilpatrick K et al. Chemical Induction of Hsp70 Reduces a-Synuclein Aggregation in Neuroglioma Cells. ACS Chem. Biol. 2013, 8, 1460-1468.

Terrab L et al. Hsp70 and the Unfolded Protein Response as a Challenging Drug Target and an Inspiration for Probe Molecule Development. ACS Med. Chem. Lett. 2020, in press.

Davis AK et al. Targeting Hsp70 Facilitated Protein Quality Control for Treatment of Polyglutamine Diseases. Cell. Mol. Life Sci. 2019, Ahead of Print.

Siebzehnruebl FA et al. Early Postnatal Behavioral, Cellular, and Molecular Changes in Models of Huntington Disease Are Reversible by HDAC Inhibition. Proc. Natl. Acad. Sci. U. S. A. 2018, 115, E8765-E8774.

Pernet L et al. HDAC6-Ubiquitin Interaction Controls the Duration of HSF1 Activation after Heat Shock. Mol. Biol. Cell 2014, 25, 4187-4194.

Crotti A et al. Mutant Huntingtin Promotes Autonomous Microglia Activation Via Myeloid Lineage-Determining Factors. Nat. Neurosci. 2014, 17, 513-521.

Kim JY et al. The 70-kDa heat shock protein (Hsp70) as a therapeutic target for stroke. Expert Opin Ther Targets. Mar. 2018; 22(3): 191-199.

International Preliminary Report on Patentability issued for Application No. PCT/US2021/017890, dated Aug. 25, 2022.

International Search Report and Written Opinion received in PCT/US2021/017890, dated Apr. 26, 2021, 8 pages.

Lee et.al. ‘Synthesis of 4-Carbethoxy-5-aryl-5,6-dihydro-2H-1,2,6-thiadiazine 1, 1,-dioxides’ In Bull. Korean Chem. Soc., 1992, vol. 13(5), pp. 462-463. p. 462, col. 2, para 2, Scheme.

Veguillas et.al. Silver Effect in Regiodivergent Gold-Catalyzed Hydroaminations in ACS y Catalysis, 2019, vol. 9, pp. 2552-2557. p. 2553, Tabel 2.

* cited by examiner

MAL1-271

12g

10i

10g

11g
Molecular Weight: 536.42100

12g
Molecular Weight: 452.30300

5g
Molecular Weight: 451.31500

9g
Molecular Weight: 409.23400

7h
Molecular Weight: 485.33200

11h
Molecular Weight: 584.46500

12h
Molecular Weight: 500.34700

5i
Molecular Weight: 451.31500

6i
Molecular Weight: 641.55700

10i
Molecular Weight: 485.33200

930-62

(+)-951-66

(-)-951-67

930-63

930-60
Molecular Weight: 590.47200

930-64
Molecular Weight: 556.45500

959-74
Molecular Weight: 612.51900

944-54
Molecular Weight: 451.31500

959-21
Molecular Weight: 513.38600

Molecular Weight: 438.27600
930-91

Molecular Weight: 532.36440
962.04

930-79
Molecular Weight: 500.34700

959-30

995-28
Molecular Weight: 738.49500

978.02
Molecular Weight: 500.40600

944-071
Molecular Weight: 582.27000

1006-04
Molecular Weight: 596.29700

995-36
Molecular Weight: 499.35900

993-10
Molecular Weight: 499.35900

974-46
Molecular Weight: 505.38100

974-47
Molecular Weight: 463.32600

974-69
Molecular Weight: 462.29800

962-36
Molecular Weight: 437.28800

984-75
Molecular Weight: 422.37521

984-71
Molecular Weight: 408.34821

HEAT SHOCK PROTEIN MODULATORS AND ANTI-HUNTINGTON DISEASE THERAPEUTIC AGENTS

CROSS-REFERENCE TO RELATED APPLICATIONS

This application is a US national stage application under 35 U.S.C. § 371 of PCT/US2021/017890 filed Feb. 12, 2021, which claims priority to U.S. Provisional Patent Application No. 62/976,838 filed Feb. 14, 2020, each of which is incorporated herein by reference in its entirety.

STATEMENT REGARDING FEDERALLY SPONSORED RESEARCH

This invention was made with government support under grant GM131732 and DK079307 awarded by the National Institutes of Health. The government has certain rights in the invention.

BACKGROUND

Heat shock proteins (HSPs) support the folding of nascent polypeptides, prevent protein aggregation, and assist in the transport of other proteins across the membrane. Proteins in the Hsp70 family (collectively referred to as "Hsp70") play a dual role in protecting cells from lethal damage after environmental stress, while targeting cells for immune-mediated cytolytic attack. The increased expression of Hsp70 in the cytoplasm is known to protect many cell types under pressure by preventing misfolding, aggregation, and denaturation of cytoplasmic and organellar proteins and inhibiting various apoptotic pathways. However, plasma membrane-bound Hsp70 provides a target structure for lytic attack mediated by natural killer cells. Cells may be stressed by temperature; injury (trauma); hereditary disease; metabolic defects; apoptosis; infection; toxins; radiation; oxides; excess/lack of nutrients or metabolic products. It is known in the art that Hsp70 can mediate a response against cellular damage in various medical conditions, which otherwise result in protein misfolding/aggregation and cell death. There is a need for compounds that function as an Hsp70 agonist without increasing the levels of Hsp70, particularly compounds that blunt the formation of toxic aggregates in cells and counteract neurodegeneration.

Members of the Hsp70 family are highly expressed in many cancers. The overexpression of Hsp70 is associated with metastasis, whereas the repression of Hsp70 results in the inhibition of tumor cell proliferation and the induction of apoptosis. Hsp70 chaperone activity may also influence tumorigenesis by regulating the activity of proteins that are involved in the cell cycle machinery. Antagonists of Hsp70 have been known to inhibit or reduce tumor cell invasion or metastasis. For example, treatment with histone deacetylase (HDACs) inhibitors results in the hyperacetylation of chaperones including Hsp70, which affects their function. HDAC inhibitor-mediated deregulation of chaperone function, in turn, deregulates protein homeostasis and induces protein misfolding and proteotoxic stress. In the context of tumors which are particularly dependent on functional chaperones for maintaining protein homeostasis, HDAC inhibitors tip the balance toward lethal proteotoxic and ER stress. There is a need for compounds and compositions including heat shock protein antagonists to inhibit or reduce tumor cell invasion or metastasis.

The compounds, compositions, and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. The compounds and compositions can be used for treating or preventing a heat-shock protein responsive disorder or suppressing protein aggregation in a subject. The heat shock protein responsive disorder can be a Hsp70 responsive disorder including neurodegenerative disorders. The compounds are also suitable for use in treating cancer. The compounds disclosed herein include thiadiazines compounds and derivatives thereof having a structure represented by Formula I-A:

Formula I-A

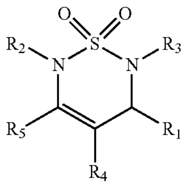

wherein $R_1$ is selected from aryl or heteroaryl, wherein $R_1$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_2$ is selected from H, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —R'$SO_3$H, —R'$SO_2$NHCOR", —R'CONH$SO_2$R", —R'NH$SO_2$R", —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ is selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2$H, —R'$CO_2$R", —R'$CONH_2$, —R'CONHR", —R'CONR"R'", —R'CONHOH, —R'CONHCN, —R'$SO_3$H, —R'$SO_2$NHCOR", —R'CONH$SO_2$R", —R'$SO_2$ NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_4$ is selected from —$CO_2H$, —R'$CO_2H$, —R'$CO_2$R", —$CO_2$R", —$CONH_2$, —R'$CONH_2$, —R'CONHR", —CONHR", —R'CONR"R"', —CONR"R"', —R'CONHOH, —CONHOH, —R'CONHCN, —CONHCN, —CHO, —R'CHO, —R'$NH_2$, —R'NHR", —R'NR"R"', —$NH_2$, —NHR", —NR"R"', —R'NHCOH, —R'NHCOR", —R'NR"COR"', —NHCOH, —NHCOR", —NR"COR"', wherein R', R", and R"' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R"' together with the atom to which they are attached combine to form a 5-6 membered ring, wherein R', R", and R"' are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl; and $R_5$ is selected from H, halogen, $C_1$-$C_6$ alkyl, $C_2$-$C_6$ alkenyl, $C_1$-$C_6$ alkoxy, $C_1$-$C_6$ haloalkyl, wherein $R_5$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl, wherein when $R_2$ is H, $R_3$ is not H.

Methods of preparing and using the thiadiazine compounds and derivatives thereof are also disclosed, as well as a method for resolution of racemic product mixtures by chromatography on chiral stationary phase.

DETAILED DESCRIPTION

Figure 1:
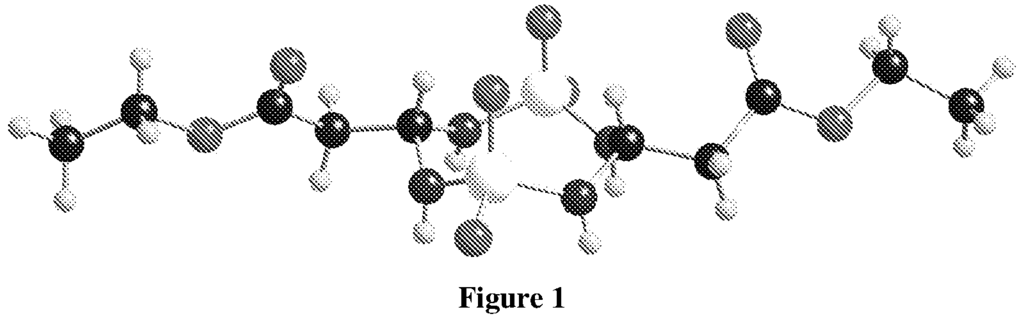
FIG. 1 shows X-ray structure of 1,1,5,5-tetraoxido-1,5,2,4,6,8-dithiatetrazocane-3,7-diyl)diacetate 3 (CCDC 1972400).

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word “comprise” and other forms of the word, such as “comprising” and “comprises,” means including but not limited to, and is not intended to exclude, for example, other additives, components, integers, or steps.

As used in the description and the appended claims, the singular forms “a,” “an,” and “the” include plural referents unless the context clearly dictates otherwise. Thus, for example, reference to “a composition” includes mixtures of two or more such compositions, reference to “an analog” includes mixtures of two or more such analogs, and the like.

“Optional” or “optionally” means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from “about” one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "Hsp70 responsive disorder" is meant a class of conditions or disorders that are regulated by Hsp70. Exemplary Hsp70 responsive disorder or conditions include, but are not limited to myopathy, both congenital such as muscle dystrophies, and acquired such as rhabdomyolysis, polymyositis, and dermatomyositis; acute trauma; traumatic toxicosis due to crash injury; ischemia-reperfusion injury including stroke and myocardial infarction; acute kidney injury; heart failure; muscle damage as a result of the excessive physical exercise, e.g., without anabolic effects such as increase in body mass; cancer; fibrosis, including liver, pulmonary and cystic fibrosis; neurodegenerative diseases such as Alzheimer's, Huntington's, Parkinson's, and amyotropic lateral sclerosis; certain inflammation; reduced physical performance (e.g., endurance), e.g., relative to absolute capability of individual; reduced mental performance, e.g., relative to absolute capability of individual; fatigue syndrome; sleep deprivation; sepsis; and hemorrhagic shock. In a particular example, the Hsp70 responsive disorder or condition may be muscle degeneration and impairment stemming from various causes including tissue ischemia, severe injury, exercise-induced tissue injury and fatigue, advanced age, muscular dystrophy resulting from genetic defects and also caused by major diseases such as cancer, kidney failure and others. In a particular embodiment, the Hsp70 responsive disorder or conditions is stroke or cancer, e.g., melanoma.

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. The substituent as described herein can include one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —$C(O)O^-$.

The term "ester" as used herein is represented by the formula —$OC(O)A^1$ or —$C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. Tautomers of certain embodiments comprising compounds disclosed herein would be recognized by those of skill in the art and are also expressly contemplated herein. Thus, in certain embodiments, the disclosure provides enantiomers, diastereomers, tautomers, and mixtures thereof, of compounds disclosed herein. It is to be understood that the chiral centers of the compounds provided herein may undergo epimerization in vivo depending on their rate of isomerization. As such, one of skill in the art will recognize that administration of a compound in its absolute configuration (such as R- or R,S-) is equivalent, for compounds that undergo epimerization in vivo, to administration of the compound as its epimer (such as S-, or S, S-).

The compounds disclosed herein can be prepared and/or administered as single enantiomers (enantiomerically pure and having an enantiomeric excess of >90%, preferably at least 97%, more preferably at least 99%), enantiomerically enriched (one of the enantiomers of a compound is present in excess compared to the other enantiomer), diastereomerically pure (having a diastereomeric p excess of >90%, preferably at least 97%, more preferably at least 99%), diastereomerically enriched (one of the diastereomers of a compound is present in excess compared to the other diastereomer), or as a racemic mixture (an equimolar mixture of two enantiomeric components).

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

Disclosed herein are compounds used for treating or preventing a heat-shock protein responsive disorder or suppressing protein aggregation in a subject. The compounds can include thiadiazines and derivatives thereof having a structure according to Formula I, Formula I

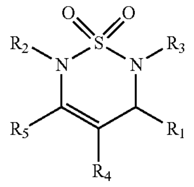

wherein $R_1$ is selected from aryl or heteroaryl, wherein $R_1$ is optionally substituted with one or more groups (such as a group selected from halogen, hydroxyl, carboxyl, amino, cyano, nitro, isocyano, alkyl, haloalkyl, haloalkoxy, cycloalkyl, heterocycloalkyl, aryl, or heteroaryl);

$R_2$ is selected from H, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —R'$SO_3$H, —R'$SO_2$NHCOR", —R'$CONHSO_2$R", —R'$NHSO_2$R", or —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups (such as a group selected from halogen, hydroxyl, carboxyl, amino, cyano, nitro, isocyano, alkyl, haloalkyl, haloalkoxy, cycloalkyl, heterocycloalkyl, aryl, or heteroaryl);

$R_3$ is selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2$H, —R'$CO_2$R", —R'$CONH_2$, —R'CONHR", —R'CONR"R'", —R'CONHOH, —R'CONHCN, —R'$SO_3$H, —R'$SO_2$NHCOR", —R'$CONHSO_2$R", or —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups (such as a group selected from halogen, hydroxyl, carboxyl, amino, cyano, nitro, isocyano, alkyl, haloalkyl, haloalkoxy, cycloalkyl, heterocycloalkyl, aryl, or heteroaryl);

$R_4$ is selected from —$CO_2$H, —R'$CO_2$H, —R'$CO_2$R", —$CO_2$R", —$CONH_2$, —R'$CONH_2$, —R'CONHR", —CONHR", —R'CONR"R'", —CONR"R'", —R'CONHOH, —CONHOH, —R'CONHCN, —CONHCN, —CHO, —R'CHO, —R'$NH_2$, —R'NHR", —R'NR"R'", —$NH_2$, —NHR", —NR"R'", —R'NHCOH, —R'NHCOR", —R'NR"COR'", —NHCOH, —NHCOR", or —NR"COR'", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring, wherein R', R", and R' are independently optionally substituted with one or more groups (such as a group selected from halogen, hydroxyl, carboxyl, amino, cyano, nitro, isocyano, alkyl, haloalkyl, haloalkoxy, cycloalkyl, heterocycloalkyl, aryl, or heteroaryl); or wherein $R_2$ and $R_4$ together with the atoms to which they are attached, combine to form a heterocyclic ring, wherein the heterocyclic ring is substituted or unsubstituted; and $R_5$ is selected from H, halogen, $C_1$-$C_6$ alkyl, $C_2$-$C_6$ alkenyl, $C_1$-$C_6$ alkoxy, or $C_1$-$C_6$ haloalkyl, wherein $R_5$ is optionally substituted with one or more groups (such as a group selected from halogen, hydroxyl, carboxyl, amino, cyano, nitro, isocyano, alkyl, haloalkyl, haloalkoxy, cycloalkyl, heterocycloalkyl, aryl, or heteroaryl), wherein when $R_2$ is H, $R_3$ is not H, or a pharmaceutically acceptable salt, stereoisomer, or tautomer thereof.

The thiadiazine compounds and derivatives thereof can have a structure according to Formula I-A, Formula I-A

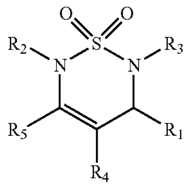

wherein $R_1$ is selected from substituted or unsubstituted aryl or substituted or unsubstituted heteroaryl;

$R_2$ and $R_3$ are independently selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —R'$SO_3$H, —R'$SO_2$NHCOR", —R'$CONHSO_2$R", —R'NH-$SO_2$R", —R'$SO_2$NHR", —CHO, —R'CHO, —R'$NH_2$, —R'NHR", —R'NR"R'41 , —$NH_2$, —NHR", —NR"R'", —R'NHCOH, —R'NHCOR", —R'NR-"COR'", —NHCOH, —NHCOR", or —NR"COR'", wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring; wherein $R_2$ and $R_3$ are independently and optionally substituted, wherein R', R", and R'" are independently optionally substituted;

$R_4$ is selected from —$CO_2H$, —R'$CO_2H$, —R'$CO_2$R", —$CO_2$R", —$CONH_2$, —R'$CONH_2$, —R'CONHR", —CONHR", —R'CONR"R'", —CONR"R'", —R'CONHOH, —CONHOH, —R'CONHCN, —CONHCN, —CHO, —R'CHO, —R'NHR", —R'NR"R'", —$NH_2$, —NHR", —NR"R'", —R'NHCOH, —R'NHCOR", —R'NR"COR'", —NHCOH, —NHCOR", —NR"COR'", wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring; wherein $R_4$ is optionally substituted, wherein R', R", and R'" are independently optionally substituted; and $R_5$ is selected from H, halogen, $C_1$-$C_6$ alkyl, $C_2$-$C_6$ alkenyl, $C_1$-$C_6$ alkoxy, $C_1$-$C_6$ haloalkyl, wherein $R_5$ is optionally substituted.

In some aspects of Formula I-A, $R_1$ is selected from aryl or heteroaryl, wherein $R_1$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_2$ and $R_3$ are independently selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2H$, —$CO_2$R", —R/$CO_2$R", —$CONH_2$, —R'$CONH_2$, —CONHR", —R'CONHR", —CONR"R'", —R'CONR"R'", —CONHOH, —R'CONHOH, —R'CONHCN, —R'$SO_3H$, —R'$SO_2$NHCOR", —R'$CONHSO_2$R", —R'NH-$SO_2$R", —R'$SO_2$NHR", —CHO, —R'CHO, —R'$NH_2$, —R'NHR", —R'NR"R'", —$NH_2$, —NHR", —NR"R'", —R'NHCOH, —R'NHCOR", —R'NR"COR'", —NHCOH, —NHCOR", or —NR"COR'", wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring, wherein R', R", and R' are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl, wherein $R_2$ and $R_3$ are independently and optionally substituted;

$R_4$ is selected from —$CO_2H$, —R'$CO_2H$, —R'$CO_2$R", —$CO_2$R", —$CONH_2$, —R'$CONH_2$, —R'CONHR", —CONHR", —R'CONR"R'", —CONR"R'", —R'CONHOH, —CONHOH, —R'CONHCN, —CONHCN, —CHO, —R'CHO, —R'$NH_2$, —R'NHR", —R'NR"R'", —$NH_2$, —NHR", —NR"R'", —R'NHCOH, —R'NHCOR", —R'NR"COR'", —NHCOH, —NHCOR", —NR"COR'", wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring; wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl, wherein $R_4$ is optionally substituted; and $R_5$ is selected from H, halogen, $C_1$-$C_6$ alkyl, $C_2$-$C_6$ alkenyl, $C_1$-$C_6$ alkoxy, $C_1$-$C_6$ haloalkyl, wherein $R_5$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl, wherein when $R_2$ is H, $R_3$ is not H.

In some aspects, the thiadiazine compound of Formula I-A, is such that:

Formula I-A

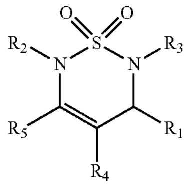

$R_1$ is selected from aryl or heteroaryl, wherein $R_1$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_2$ is selected from H, —R'$CO_2H$, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —R'$SO_3H$, —R'$SO_2$NHCOR", —R'$CONHSO_2$R", or —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl;

$R_3$ is selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2H$, —R'$CO_2$R", —R'$CONH_2$, —R'CONHR", —R'CONR"R'", —R'CONHOH, —R'CONHCN, —R'$SO_3H$, —R'$SO_2$NHCOR", —R'$CONHSO_2$R", or —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl;

$R_4$ is selected from —$CO_2$H, —R'$CO_2$H, —R'$CO_2$R", —$CO_2$R", —$CONH_2$, —R'$CONH_2$, —R'CONHR", —CONHR", —R'CONR"R'", —CONR"R'", —R'CONHOH, —CONHOH, —R'CONHCN, —CONHCN, —CHO, —R'CHO, —R'$NH_2$, —R'NHR", —R'NR"R'", —$NH_2$, —NHR", —NR"R'", —R'NHCOH, —R'NHCOR", —R'NR"COR'", —NHCOH, —NHCOR", or —NR"COR'", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring; and $R_5$ is selected from H, halogen, $C_1$-$C_6$ alkyl, $C_2$-$C_6$ alkenyl, $C_1$-$C_6$ alkoxy, or $C_1$-$C_6$ haloalkyl, wherein when $R_2$ is H, $R_3$ is not H.

In further aspects of Formula I-A, $R_1$ is selected from aryl or heteroaryl, wherein $R_1$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_2$ is selected from H, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —R'$SO_3$H, —R'$SO_2$NHCOR", —R'CONH$SO_2$R", —R'NH$SO_2$R", —R'$SO_2$NHR", wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ is selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2$H, —R'$CO_2$R", —R'$CONH_2$, —R'CONHR", —R'CONR"R'", —R'CONHOH, —R'CONHCN, —R'$SO_3$H, —R'$SO_2$NHCOR", —R'CONH$SO_2$R", —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_4$ is selected from —$CO_2$H, —R'$CO_2$H, —R'$CO_2$R", —$CO_2$R", —$CONH_2$, —R'$CONH_2$, —R'CONHR", —CONHR", —R'CONR"R'", —CONR"R'", —R'CONHOH, —CONHOH, —R'CONHCN, —CONHCN, —CHO, —R'CHO, —R'$NH_2$, —R'NHR", —R'NR"R'", —$NH_2$, —NHR", —NR"R'", —R'NHCOH, —R'NHCOR", —R'NR"COR'", —NHCOH, —NHCOR", —NR"COR'", wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl; and $R_5$ is selected from H, halogen, $C_1$-$C_6$ alkyl, $C_2$-$C_6$ alkenyl, $C_1$-$C_6$ alkoxy, $C_1$-$C_6$ haloalkyl, wherein $R_5$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl, wherein when $R_2$ is H, $R_3$ is not H.

In some embodiments of Formula I-A, $R_1$ can be an aryl or heteroaryl substituted with two or more halogens. For example, $R_1$ can be dichlorophenyl, preferably 2,4-$Cl_2C_6H_3$.

In some embodiments of Formula I-A, the thiadiazine compounds can have a structure according to Formula I-A-1, Formula I-A-1

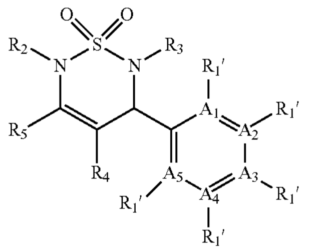

wherein $A_1$-$A_5$, are independently selected from C or N;

$R_1$', independently for each occurrence, is absent or selected from hydrogen, halogen, hydroxyl, carboxyl, amino, cyano, nitro, isocyano, alkyl (e.g., $C_1$, $C_2$, $C_3$, $C_4$, $C_5$, or $C_6$ alkyl), haloalkyl, haloalkoxy, cycloalkyl, heterocycloalkyl, aryl (e.g., $C_6$ aryl), or heteroaryl (e.g., $C_3$ to $C_5$ heteroaryl); and $R_2$ to $R_5$ are as described herein.

In some examples of Formula I-A-1, $R_1$', independently for each occurrence, is hydrogen or halogen (e.g., F, Cl, or Br). In some examples, at least one $R_1$' is a halogen selected from F, Cl, or Br, preferably F or Cl, more preferably Cl. In some examples, at least two $R_1$'s include a halogen selected from F, Cl, or Br, preferably F or Cl, more preferably Cl. When at least two $R_1$'s are present, one $R_1$' can be in the ortho position and one $R_1$' in the para position.

In some examples of Formula I-A-1, $R_1$', at least one of $A_1$, $A_2$, $A_3$, $A_4$, and $A_5$ is C. In some examples of Formula I-A-1, $R_1$', at least two of $A_1$, $A_2$, $A_3$, $A_4$, and $A_5$ is C. In some examples of Formula I-A-1, $R_1$', at least three of $A_1$, $A_2$, $A_3$, $A_4$, and $A_5$ is C. In some examples of Formula I-A-1, $R_1$', at least four of $A_1$, $A_2$, $A_3$, $A_4$, and $A_5$ is C. In some examples of Formula I-A-1, $R_1'$, $A_1$, $A_2$, $A_3$, $A_4$, and $A_5$ are all C. In some examples of Formula I-A-1, $R_1'$, at least one of $A_1$, $A_2$, $A_3$, $A_4$, and $A_5$ is N.

The compounds and derivatives thereof can have a structure according to Formula I-D, Formula I-D

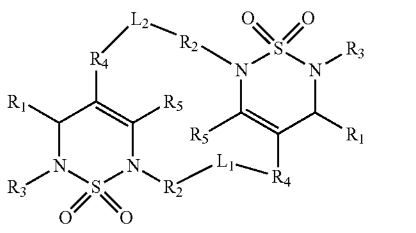

wherein $R_1$ is selected from aryl or heteroaryl, wherein $R_1$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl; $R_2$ is selected from —R'$CO_2$—, —$CO_2$R"—, —R'$CO_2$R"—, —CONH—, —R'CONH—, —CONHR"—, —R'CONHR"—, —CONR"R'"—, —R'CONR"R'"—, —CONHO—, —R'CONHO—, —R'CONCN—, —R'$SO_3$—, —R'$SO_2$NHCOR"—, —R'CONH$SO_2$R"—, —R'NH$SO_2$R"—, or —R'$SO_2$NHR"—, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ is selected from H, alkyl, alkoxy, cycloalkyl, alkylcycloalkyl, cycloalkenyl, alkylcycloalkenyl, cycloheteroalkyl, alkylcycloheteroalkyl, aryl, alkylaryl, heteroaryl, alkylheteroaryl, —R'$CO_2$H, —R'$CO_2$R", —R'$CONH_2$, —R'CONHR", —R'CONR"R'", —R'CONHOH, —R'CONHCN, —R'$SO_3$H, —R'$SO_2$NHCOR", —R'CONH$SO_2$R", or —R'$SO_2$NHR", wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, wherein R', R", and R'" are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl;

$R_4$ is selected from —$CO_2$—, —R'$CO_2$—, —R'$CO_2$R"—, —$CO_2$R"—, —CONH—, —R'CONH—, —R'CONHR"—, —CONHR"—, —R'CONR"R'"—, —CONR"R'"—, —R'CONHOH—, —CONHO—, —R'CONCN—, —CONCN—, —CO—, —R'CO—, —R'NH—, —R'NHR"—, —R'NR"R'"—, —NH—, —NHR"—, —NR"R'"—, —R'NHCO—, —R'NHCOR"—, —R'NR"COR'"—, —NHCO—, —NHCOR"—, or —NR"COR'"—, wherein R', R", and R' are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, alkylcycloalkenyl, cycloheteroalkyl, alkylcycloheteroalkyl, cycloheteroalkenyl, aryl, alkylaryl, heteroaryl, alkylheteroaryl, or R" and R'" together with the atom to which they are attached combine to form a 5-6 membered ring, wherein R', R", and R' are independently optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl; and $R_5$ is selected from H, halogen, $C_1$-$C_6$ alkyl, $C_2$-$C_6$ alkenyl, $C_1$-$C_6$ alkoxy, or $C_1$-$C_6$ haloalkyl, wherein $R_5$ is optionally substituted with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl, $L_1$ and $L_2$ are linkers that are independently absent or selected from the group consisting of —$C_2$-$C_6$ alkenyl- (such as —C═C—), —$C_1$-$C_6$ alkyl-; —C(═O)—; —C(═O)R'—; —OC(═O)R'—; —C(═O)NR'R"—; —NR'C(═O)R"—; —OR'—; —NR'R"—; —OC(═O)NR'R"—; wherein R' and R" are selected from $C_1$-$C_6$ alkyl or $C_2$-$C_6$ alkenyl.

In some embodiments of Formula I, Formula I-A, Formula I-A-1, or Formula I-D, $R_2$ can be selected from H, —R'$CO_2$H, —R'$CO_2$R", —R'$CONH_2$, —R'CONHR", —R'CONR"R'", —R'NH$SO_2$R", —R'CONHOH, wherein R' can be selected from $C_1$-$C_6$ alkyl (e.g., $C_1$, $C_2$, $C_3$, $C_4$, $C_5$, or $C_6$ alkyl) or alkylaryl (e.g., $C_1$, $C_2$, $C_3$, $C_4$, $C_5$, or $C_6$ alkylaryl), and R" and R'" can be independently selected from $C_1$-$C_6$ alkyl (e.g., $C_1$, $C_2$, $C_3$, $C_4$, $C_5$, or $C_6$ alkyl), $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloheteroalkyl, alkylcycloheteroalkyl, cycloalkenyl, cycloheteroalkenyl, aryl (e.g., $C_6$ aryl), or heteroaryl. R', R", and R'" as defined with respect to $R_2$ are each independently optionally substituted, such as with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl. In some examples, R', R", and R'" are each independently optionally substituted with one or more groups selected from halogen, hydroxyl, amino, or alkyl.

In some embodiments of Formula I-A or Formula I-A-1, $R_2$ can be selected from H, —R'$CO_2$H, —R'$CO_2$R", —R'$CONH_2$, —R'CONHR", —R'CONR"R'", or —R'CONHOH, wherein R' is selected from $C_1$-$C_6$ alkyl, and R" and R'" are independently selected from $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, cycloheteroalkyl, cycloalkenyl, cycloheteroalkenyl, aryl, or heteroaryl.

For purposes of this disclosure, the definitions of $R_2$ and $R_4$ with respect to Formula I-D, such as R'$CO_2$H, can exclude hydrogen substituents which satisfy the valencies of the defined moiety.

In some embodiments of Formula I, Formula I-A, Formula I-A-1, or Formula I-D, $R_2$ is not H. In some embodiments of Formula I-A or Formula I-A-1, $R_2$ is H and when $R_2$ is H, $R_3$ is not simultaneously H. In some examples of Formula I, Formula I-A, or Formula I-A-1, when $R_2$ is H, $R_3$ can be selected from —R'$CO_2$H, —R'$CO_2$R", —R'$CONH_2$, —R'CONHR", —R'CONR"R'", or —R'CONHOH, wherein R' can be selected from $C_1$-$C_6$ alkyl, and R" and R'" can be independently selected from $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, cycloheteroalkyl, cycloalkenyl, cycloheteroalkenyl, aryl, or heteroaryl.

In some embodiments of Formula I, Formula I-A, Formula I-A-1, or Formula I-D, $R_3$ can be selected from H, $C_1$-$C_6$ alkyl (e.g., $C_1$, $C_2$, $C_3$, $C_4$, $C_5$, or $C_6$ alkyl), $C_1$-$C_6$-alkylcycloalkyl, $C_1$-$C_6$ alkylaryl, $C_1$-$C_6$ alkylheteroaryl, —R'$CO_2$H, —R'$CO_2$R", —R'$CONH_2$, —R'CONHR", —R'CONR"R'", —R'CONHOH; R' can be selected from $C_1$-$C_6$ alkyl (e.g., $C_1$, $C_2$, $C_3$, $C_4$, $C_5$, or $C_6$ alkylaryl), $C_2$-$C_6$ alkenyl, cycloalkyl, cycloalkenyl, cycloheteroalkyl, $C_1$-$C_6$ alkyl cycloalkyl, $C_1$-$C_6$ alkyl cycloheteroalkyl, $C_1$-$C_6$ alkyl cycloalkenyl, aryl, $C_1$-$C_6$ alkyl aryl, heteroaryl, or $C_1$-$C_6$ alkyl heteroaryl; and R" and R'" can be independently selected from hydrogen, $C_1$-$C_6$ alkyl (e.g., $C_1$, $C_2$, $C_3$, $C_4$, $C_5$, or $C_6$ alkyl), $C_2$-$C_6$ alkenyl, $C_2$-$C_6$ alkynyl, $C_1$-$C_6$ alkoxy, $C_1$-$C_6$ haloalkyl, cycloalkyl, cycloheteroalkyl, cycloalkenyl, cycloheteroalkenyl, aryl, or heteroaryl. R', R", and R'" as defined with respect to $R_3$ are each independently optionally substituted, such as with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl. In some examples, R', R", and R'" are each independently optionally substituted with one or more groups selected from halogen, hydroxyl, amino, or alkyl.

In some embodiments of Formula I-A or Formula I-A-1, $R_3$ can be selected from H, $C_1$-$C_6$ alkyl, $C_1$-$C_6$ alkylaryl, $C_1$-$C_6$ alkylheteroaryl, —R'$CO_2$H, —R'$CO_2$R", —R'$CONH_2$, —R'CONHR", —R'CONR"R'", or —R'CONHOH; wherein R' is selected from $C_1$-$C_6$ alkyl, $C_2$-$C_6$ alkenyl, cycloalkyl, cycloalkenyl, cycloheteroalkyl, $C_1$-$C_6$ alkyl cycloalkyl, $C_1$-$C_6$ alkyl cycloheteroalkyl, $C_1$-$C_6$ alkylcycloalkenyl, aryl, $C_1$-$C_6$ alkylaryl, heteroaryl, or $C_1$-$C_6$ alkyl heteroaryl; and R" and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, cycloheteroalkyl, cycloalkenyl, cycloheteroalkenyl, aryl, or heteroaryl.

In some examples, $R_3$ can be selected from H, $C_1$-$C_6$ alkyl, —R'$CO_2$H, —R'$CO_2$R", —R'$CONH_2$, —R'CONHR", —R'CONR"R'", or —R'CONHOH; wherein R' can be selected from $C_1$-$C_6$ alkyl, $C_1$-$C_6$ alkyl aryl, or $C_1$-$C_6$ alkyl heteroaryl, and R" and R' can be independently selected from hydrogen, halogen, or $C_1$-$C_6$ alkyl. R', R", and R' are each independently optionally substituted, such as with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl.

In some embodiments of Formula I, Formula I-A, Formula I-A-1, or Formula I-D, $R_3$ is not H. In some embodiments of Formula I-A or Formula I-A-1, $R_3$ is H, and when $R_3$ is H, $R_2$ is not simultaneously H. In some examples of Formula I, Formula I-A, Formula I-A-1, or Formula I-D, when $R_3$ is H, $R_2$ can be selected from —R'$CO_2$H, —R'$CO_2$R", —R'$CONH_2$, —R'CONHR", —R'CONR"R'", or —R'CONHOH, wherein R' can be selected from $C_1$-$C_6$ alkyl, and R" and R'" can be independently selected from $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, cycloheteroalkyl, cycloalkenyl, cycloheteroalkenyl, aryl, or heteroaryl.

In some embodiments of Formula I, Formula I-A, Formula I-A-1, or Formula I-D, $R_4$ can be selected from —CONHOH, —$CO_2$H, —$CO_2$R", —$CONH_2$, —CONHR", —CONR"R'", —CONHOH, —CHO, —R'$NH_2$, —R'NHR", —R'NR"R'", —$NH_2$, —NHR", —NR"R'", —R'NHCHO, —R'NHCOR", —R'NR"COR'", —NHCHO, —NHCOR", or —NR"COR'", wherein R' is selected from a $C_1$-$C_6$ alkyl (e.g., $C_1$, $C_2$, $C_3$, $C_4$, $C_5$, or $C_6$ alkyl); and R" and R' are as described herein. In some examples, $R_4$ can be selected from —$CO_2$H or —$CO_2$R", and R" can be selected from $C_1$-$C_6$ alkyl (e.g., $C_1$, $C_2$, $C_3$, $C_4$, $C_5$, or $C_6$ alkyl), aryl, or alkylaryl. R', R", and R' as defined with respect to $R_4$ are each independently optionally substituted, such as with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl. In some examples, R', R", and R'" are each independently optionally substituted with one or more groups selected from halogen, hydroxyl, amino, or alkyl.

In some embodiments of Formula I, Formula I-A, Formula I-A-1, or Formula I-D, $R_4$ can be selected from —CONHOH, —$CO_2$H or —$CO_2$R", and R" is selected from $C_1$-$C_6$ alkyl, alkylcycloalkyl, alkylheteroaryl, aryl, or alkylaryl. R" is optionally substituted, such as with one or more groups selected from halogen, hydroxyl, carboxyl, amino, cyano, nitro, isocyano, alkyl, haloalkyl, haloalkoxy, cycloalkyl, heterocycloalkyl, aryl, or heteroaryl. In some examples, R" is optionally substituted with one or more groups selected from halogen, hydroxyl, amino, alkyl, or cyano.

In some embodiments of Formula I-A or Formula I-A-1, $R_4$ can be selected from —$CO_2$H or —$CO_2$R", wherein R" is selected from $C_1$-$C_6$ alkyl, aryl, or alkylaryl.

In some examples of Formula I, Formula I-A, and Formula I-A-1, the thiadiazine compounds and derivatives thereof can have a structure according to Formula I-A-2

Formula I-A-2

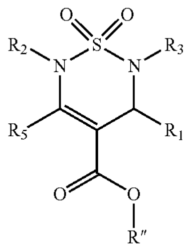

wherein R" is selected from hydrogen, $C_1$-$C_6$ alkyl (e.g., $C_1$, $C_2$, $C_3$, $C_4$, $C_5$, or $C_6$ alkyl), aryl (e.g., $C_6$ aryl), alkylaryl (e.g., $C_1$, $C_2$, $C_3$, $C_4$, $C_5$, or $C_6$ alkylaryl), heteroaryl (e.g., $C_2$-$C_6$ heteroaryl), or alkylheteroaryl (e.g., $C_1$-$C_6$alkyl-heteroaryl), wherein R" is substituted or unsubstituted, and $R_1$, $R_2$, $R_3$, and $R_5$ are as described herein.

In some embodiments of Formula I, Formula I-A, Formula I-A-1, Formula I-A-2, or Formula I-D, $R_5$ can be selected from H, halogen (F, Cl, or Br), $C_1$-$C_6$ alkyl (e.g., methyl, ethyl, or propyl), $C_1$-$C_6$ alkoxy (e.g., methoxy or ethoxy), of $C_1$-$C_3$ haloalkyl. In some examples, $R_5$ can be H. In some examples, $R_5$ can be $C_1$-$C_3$ alkyl such as methyl, ethyl, propyl, or isopropyl.

In some embodiments of Formula I-D, $L_1$ and $L_2$ are the same. For example, $L_1$ and $L_2$ are linkers independently selected from —$C_2$-$C_6$ alkenyl-, preferably —C═C—.

As described herein, $R_1$, $R_2$, $R_3$, $R_4$, and/or $R_5$ can be optionally substituted. In some embodiments, $R_1$, $R_2$, $R_3$, $R_4$, and/or $R_5$ can be optionally substituted with halogen, hydroxyl, amino, cyano, nitro, isocyano, carboxyl, hydroxyl, alkyl, alkoxy, alkenyl, haloalkyl, haloalkoxy, or cyclopropyl.

In some examples, the compounds according to Formula I, Formula I-A, Formula I-A-1, Formula I-A-2, or Formula I-D and derivatives thereof can have a structure below:

5g
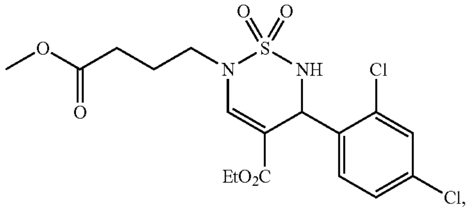
5i
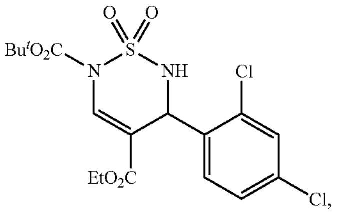
6i
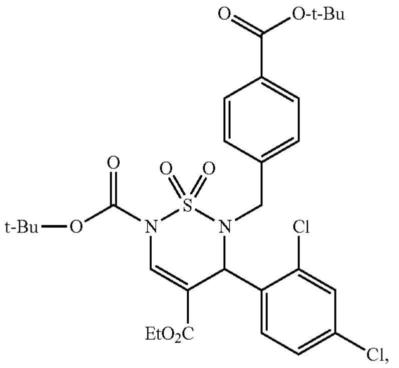
7g
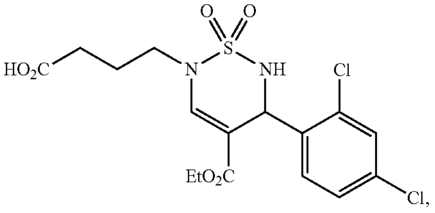
7h
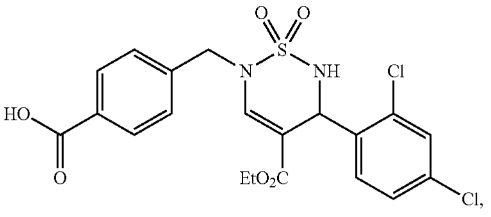
9g
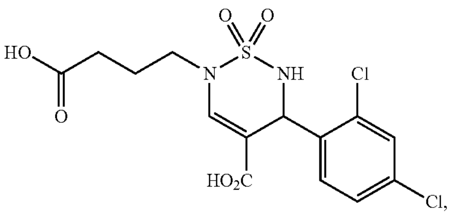
-continued
10g
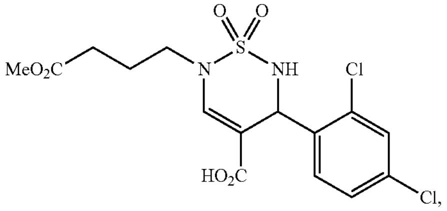
10i
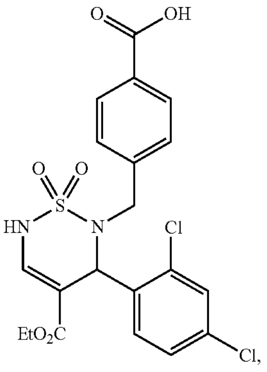
11g
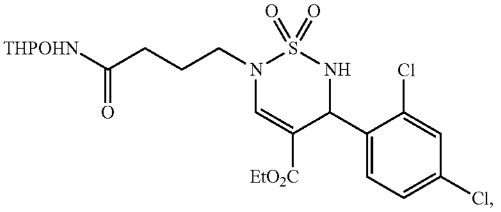
11h
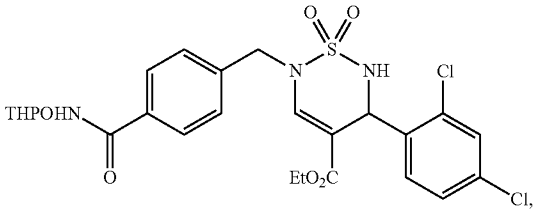
12g
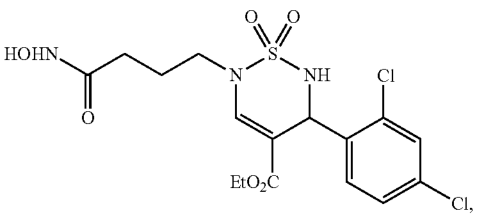
12h
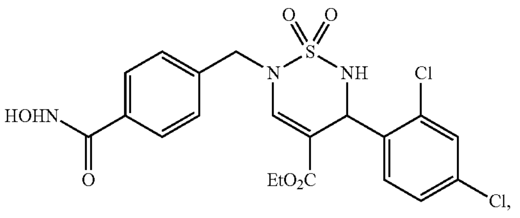

-continued
18g
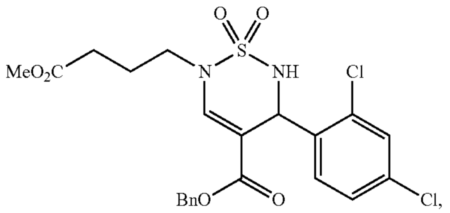
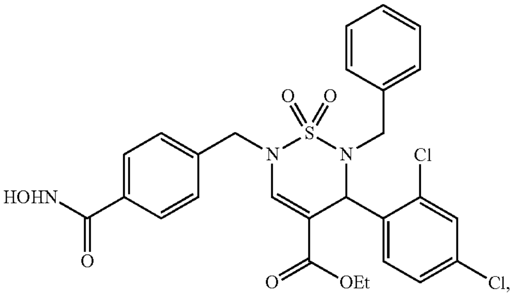
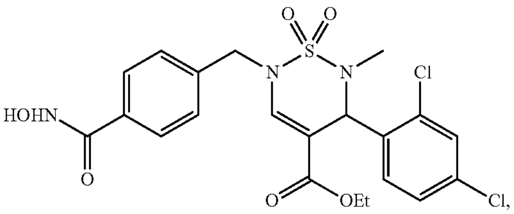
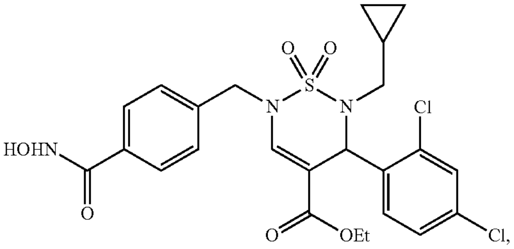
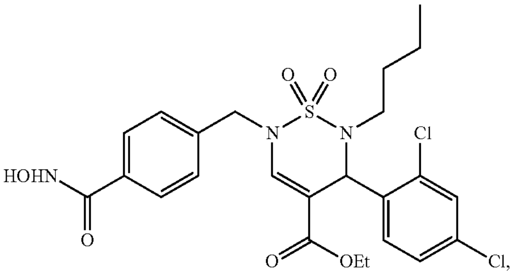
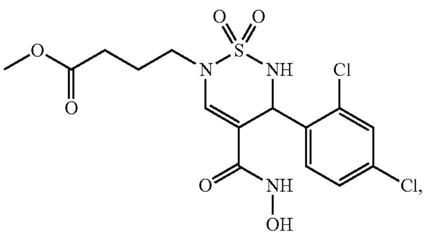
-continued
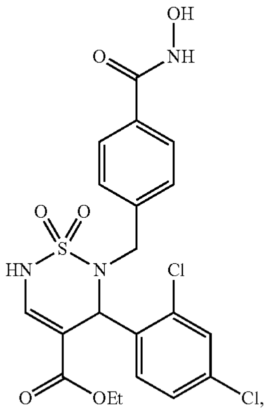
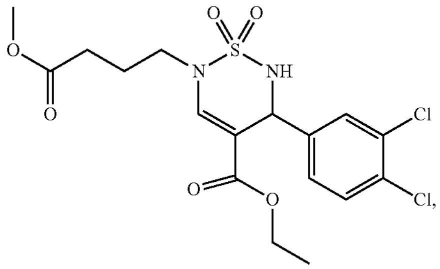
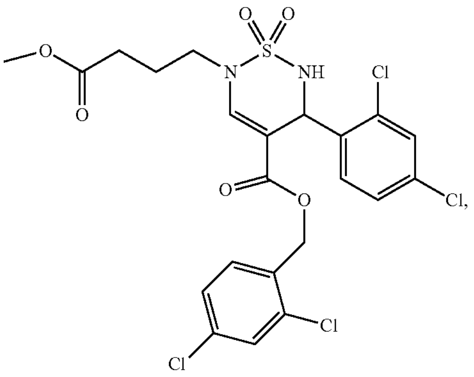
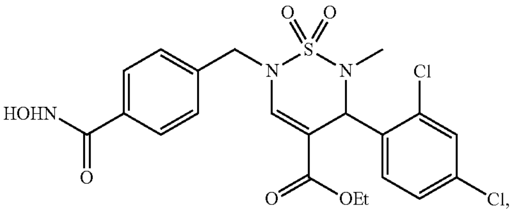
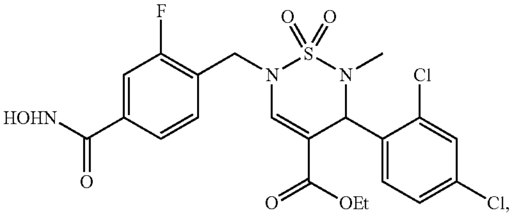

-continued
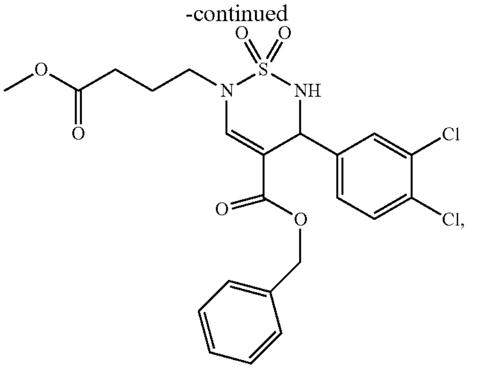
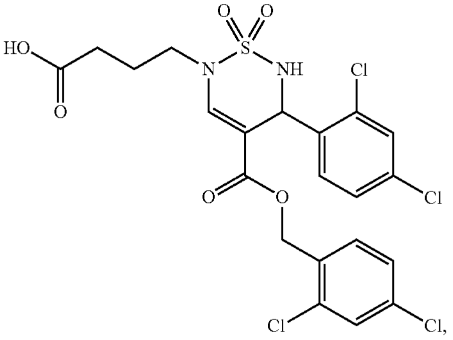
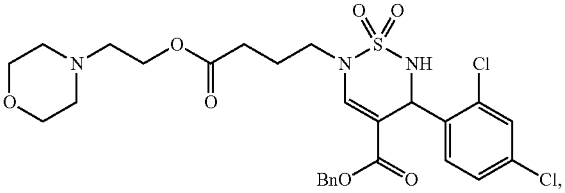
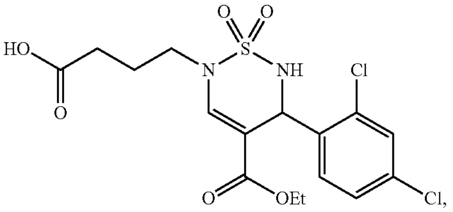
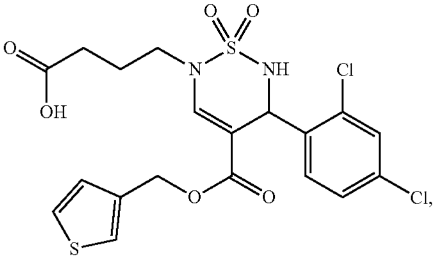
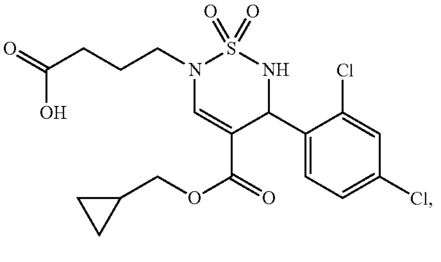
-continued
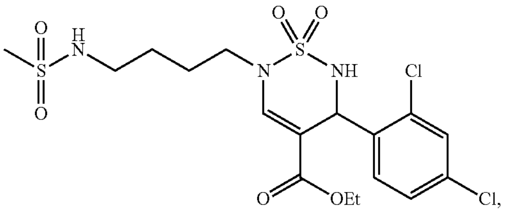
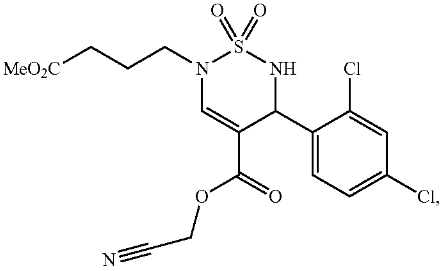
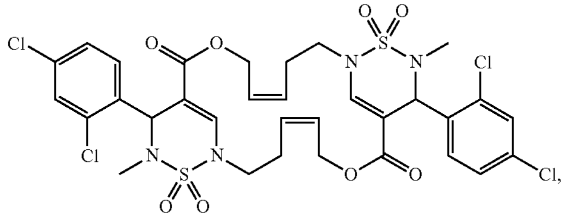
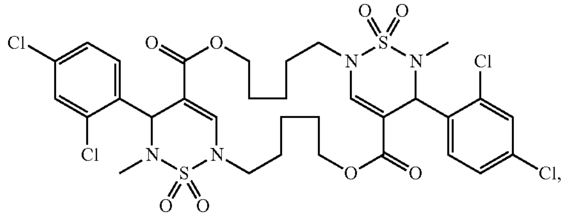
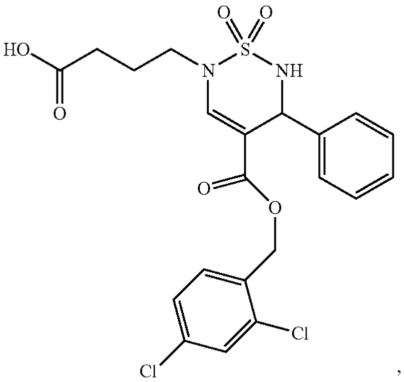
,
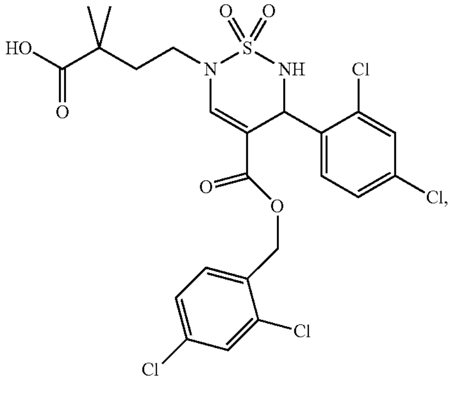

-continued
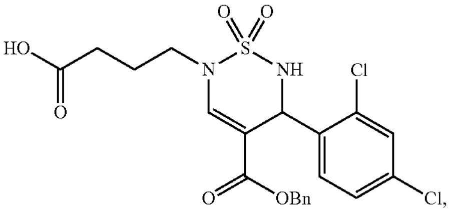
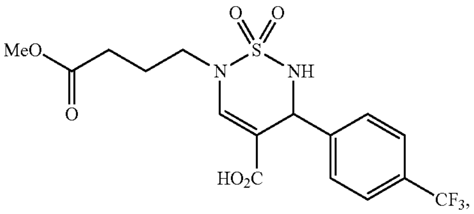
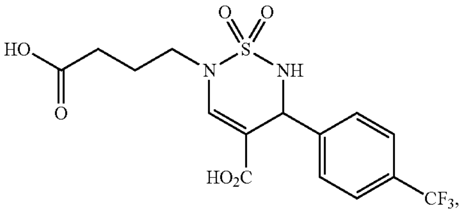
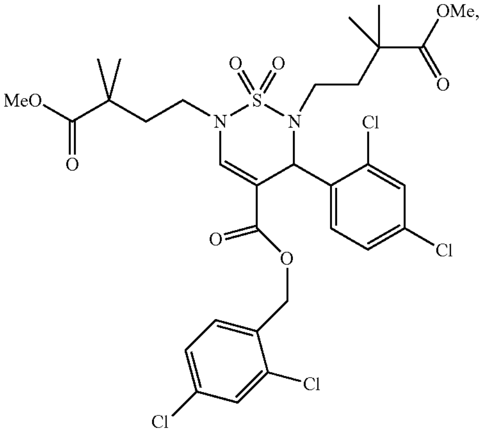
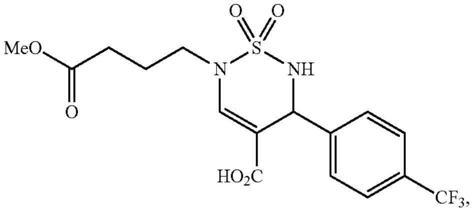
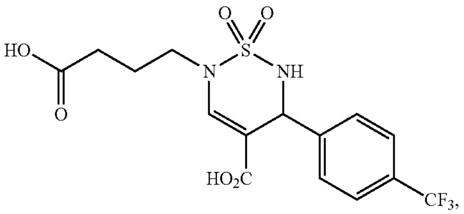
-continued
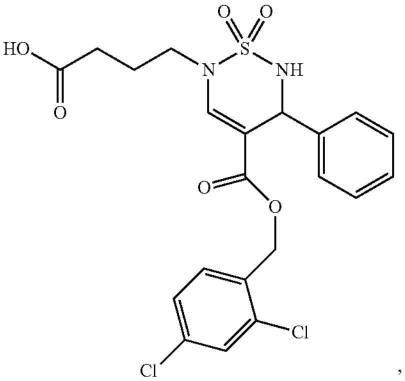
,
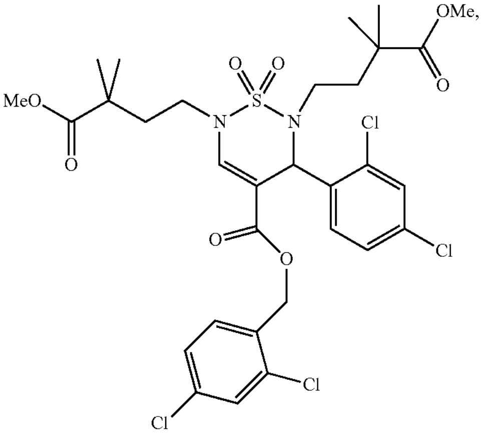
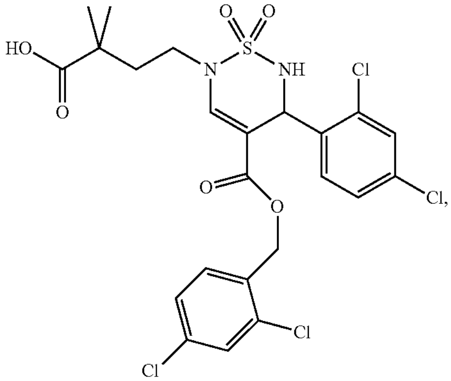
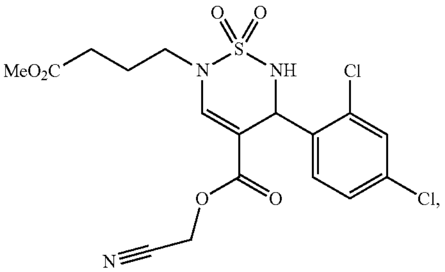
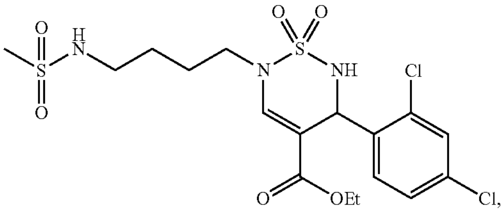
or -continued

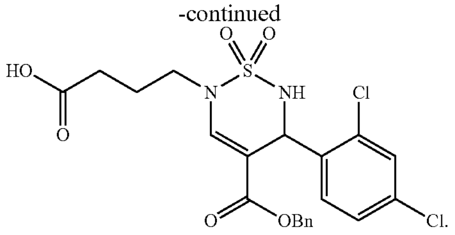

Method of Synthesis

Methods for preparing the thiadiazine compounds are also provided. The method can include condensing sulfamide with a 3,3-dialkoxypropionate in a suitable solvent to form a cyclic dimer. Examples of 3,3-dialkoxypropionate compounds include ethyl 3,3-diethoxypropionate. The sulfamide and the 3,3-dialkoxypropionate can be present in a 1:5 mole ratio. The method for preparing the thiadiazine compounds can further include condensing the cyclic dimer with an aldehyde, $R_1CHO$, in a suitable solvent to form a thiadiazine 1,1-dioxide core. $R_1$ in the aldehyde, $R_1CHO$, can be selected from $C_1$-$C_6$ alkyl, $C_6$ aryl, or $C_3$-$C_5$ heteroaryl. The cyclic dimer and the aldehyde can be present in a 1:1 mole ratio. Suitable solvents for the condensing steps can include TFA and/or $CH_2Cl_2$. The method for preparing the thiadiazine compounds can further include sequentially N-alkylating the thiadiazine 1,1-dioxide core to form the thiadiazine-1,1-dioxide compound. Suitable alkylating agents can be selected from $R_2OH$, $R_2X$ or $R_3X$, wherein X is a halogen. In some examples, $R_2$ and $R_3$ can be selected from alkyl, alkenyl, alkynyl, cycloalkyl, heterocycloalkyl, aryl, or heteroaryl. The method for preparing the thiadiazine compounds can further include saponifying the thiadiazine compound.

As described herein, the compounds can exist as a racemic mixture, as a mixture with an uneven ratio of two enantiomers, or as a mixture of diastereomers. Pure compounds can be obtained synthetically and post-synthetically. Synthetically, racemic mixtures can be avoided by using enantiomerically pure starting materials, stereocontrolled synthesis, asymmetric catalysis or biocatalysis. Post-synthetically, pure compounds can be obtained using chromatography or by the formation of diastereomeric salts or covalent derivatives and crystallization. Chiral stationary phases (for HPLC and SFC separations) can separate racemic mixtures into the individual stereoisomers and can be scaled-up preparatively. Diastereomers can also be separated by chromatographic techniques or crystallization.

Methods of Use

The compounds disclosed herein can be used for treating or preventing a heat-shock protein responsive disorder or suppressing protein aggregation in a subject. In one aspect, disclosed herein are compounds (including thiadiazine compounds and derivatives thereof) for use in the modulation of heat shock proteins, in particular Hsp70. As used herein, an Hsp responsive disorder is a medical condition in which stressed cells can be treated by increased Hsp70 expression. Such diseases can be caused by a wide variety of cellular stressors including, but not limited to, Alzheimer's disease; Huntington's disease; Parkinson's disease; frontotemporal dementia; spinal cord/medullary muscle atrophy (e.g., Kennedy's disease), spinocerebellar ataxic disease, and other neuromuscular atrophy; prion-related disorders; familial amyotrophic lateral sclerosis; ischemia; seizure; hypothermia; hyperthermia; burns; atherosclerosis hardening; acute kidney injury; injury resulting from ischemia-reperfusion including ischemic stroke and myocardial infarction; radiation exposure; glaucoma; toxin exposure; mechanical injury; inflammation; autologous disease; or an infection (bacterial, viral, fungal, or parasitic).

In some embodiments, the Hsp responsive disorder is a neurodegenerative disease. As used herein, neurodegenerative diseases include the degradation of neurons (e.g., cerebellum, spinal cord, and surrounding neurons (e.g., neuromuscular synapses), more typically brain and spinal cord neurons, or in a preferred embodiment, the degradation of neurons in the brain). Neurodegenerative diseases may include Alzheimer's disease; Huntington's disease; Parkinson's disease, Kennedy's disease, frontotemporal dementia, ischemia-reperfusion injury including ischemic stroke and myocardial infarction, a prion-related disorder, amyotrophic lateral sclerosis, and/or similar neurodegenerative condition. Neurodegenerative diseases may also include exposure to seizures, heat stress, radiation, toxins, infection, injury, acute trauma, traumatic toxicosis, heart failure, and the degradation of neurons.

In some embodiments, the Hsp responsive disorder is a protein aggregation/misfolded disease, such as Alzheimer's disease; Huntington's disease; Parkinson's disease; spongiform encephalopathies; and the like. In another embodiment, the Hsp70 responsive disorder is a disorder that causes or may cause neurological damage.

In some embodiments, the Hsp responsive disorder is sepsis, cardiac injury, muscular injury and degeneration, myopathy including congenital such as muscle dystrophies, and acquired such as rhabdomyolysis, polymyositis, and dermatomyositis, fibrosis including liver, pulmonary and cystic fibrosis, recovery from physical and exercise stress, spinal cord injury, traumatic brain injury, acute lung injury, acute kidney injury, eye neurodegenerative diseases including glaucoma and macular degeneration, certain inflammation, epilepsy, or sarcopenia as associated with aging and the progressive decline of muscle mass, strength, and quality.

The method for treating or preventing a heat-shock protein responsive disorder or suppressing protein aggregation can comprise administering to the subject, a therapeutic effective amount of a compound or composition as disclosed herein. The methods can further comprise administering a second compound or composition, such as, for example, therapeutically active co-agent used in the treatment of a neurodegenerative disease.

Another embodiment of the invention is a method of treating a subject having cancer. The disclosed compounds can exert anticancer effects due to inhibition of histone deacetylases (HDACs). Indirectly, HDAC modulation can also influence the heat shock response and thus exert synergy with Hsp70 modulation. The method of use can comprise administering to the subject, a therapeutic effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Kaposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pine blastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

Administration

The term "administration" and variants thereof (e.g., "administering" a compound) in reference to a compound disclosed herein means introducing the compound or a prodrug of the compound into the system of the animal in need of treatment. When a compound or prodrug thereof is provided in combination with one or more other active agents, "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, vaginal, intramuscular, intraperitoneal, intraarterial, intrathecal, intrabronchial, subcutaneous, intradermal, intravenous, buccal, sublingual, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, pessaries, emulsions, lotions, ointments, creams, gels, dusting powders, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, gentiles, drops, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.),) and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

For the treatment of neurodegenerative disorders, compounds and agents and compositions disclosed herein can be administered to a patient in need of treatment prior to, subsequent to, or in combination with other active agents that can treat neurodegenerative disorders.

Dosage

Appropriate dosage levels on the order of about 0.001 mg to about 5,000 mg per kilogram body weight of the compound active agent may be useful in the treatment of the diseases, disorders, and conditions contemplated herein. Typically, this effective amount of the active agent will generally comprise from about 0.001 mg to about 100 mg per kilogram of patient body weight per day. Moreover, it will be understood that this dosage of active agent can be administered in a single or multiple dosage units to provide the desired therapeutic effect.

The therapeutically effective dosage can be the amount of a compound of the present subject matter required to obtain a serum, in a concentration of 1 nM to 200 uM; 1 nM to 100 uM; 1 nM to 50 uM; 100 nM to 100 uM; 100 nM to 50 uM; 100 nM to 20 uM; 1 nM to 1 uM; and 1 nM to 100 nM. In one embodiment, the compound can be provided at a concentration of less than 200 uM; less than 100 uM; less than 50 uM; less than 25 uM; less than 15 uM; less than 10 μM; less than 5 uM; less than 2 uM; less than 1 uM; less than 500 nM; less than 200 nM; or less than 100 nM.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

The compounds or pharmaceutical compositions can be given in a single or multiple doses daily. In an embodiment, the compounds or pharmaceutical compositions are given from one to three times daily. Starting with a low dose twice daily and slowly working up to higher doses if needed is a strategy. The amount of compounds or pharmaceutically active ingredients that may be combined with the carrier materials to produce a single dosage form will vary depending upon the host treated, the nature of the disease, disorder, or condition, and the nature of the active ingredients. It is understood, however, that a specific dose level for any particular patient will vary depending upon a variety of factors, including the activity of the specific pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal pharmaceutical formulations will be determined by one skilled in the art depending upon considerations such as the particular pharmaceutically active agent combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

In an embodiment, the present compounds or pharmaceutical composition in accordance with the subject matter described herein may be an intravenous form or an oral dosage form, for example, a capsule, a tablet, liquid, and/or a powder packaged in, for example, a multi-use or single-use package, including for example, a container or bottle, a blister package.

Single dosage kits and packages containing once per day, or once per treatment, amount of the compounds or pharmaceutical composition may be prepared. Single dose, unit dose, and once-daily disposable containers of the present compounds or pharmaceutical compositions are contemplated as within the scope of the present subject matter.

Combination Therapy

As described herein, the present compounds or pharmaceutical compositions may be used in combination with an additional pharmaceutical dosage form to enhance their effectiveness in Hsp responsive disorder such as cancer, malignancy, or proliferative disorders; Alzheimer's disease; Huntington's disease; Parkinson's disease; frontotemporal dementia; spinal cord/medullary muscle atrophy (e.g., Kennedy's disease), spinocerebellar ataxic disease, and other neuromuscular atrophy; prion-related disorders; familial amyotrophic lateral sclerosis; ischemia; acute kidney injury; seizure; hypothermia; hyperthermia; burns; atherosclerosis hardening; radiation exposure; glaucoma; toxin exposure; mechanical injury; inflammation; autologous disease; or an infection (bacterial, viral, fungal, or parasitic). In this regard, the present preferred compositions may be administered as part of a regimen additionally including any other pharmaceutical and/or pharmaceutical dosage form known in the art as effective for the treatment of the specific Hsp responsive disorder. Similarly, a pharmaceutically active ingredient other than those specified herein can be added to the present preferred compositions to enhance their effectiveness in treating a specific Hsp responsive disorder. Accordingly, this additional pharmaceutically active ingredient or additional pharmaceutical dosage form can be administered to a patient either directly or indirectly, and concomitantly or sequentially, with the preferred compositions described herein.

In one embodiment, the present compounds or compositions and the additional pharmaceutical dosage form can be administered to a patient at the same time. In an alternative embodiment, one of the present preferred compounds or compositions and the additional pharmaceutical dosage form can be administered in the morning and the other can be administered in the evening.

In another embodiment, the presently described compounds can be administered to a patient in need thereof in multiple pharmaceutical dosage forms. This combination therapy may maximize the effectiveness of the present composition in treating a specific Hsp responsive disorder.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Synthesis and Selective Functionalization of Thiadiazine 1,1-Dioxides—Novel Heterocyclic Scaffolds with Efficacy in a Model of Huntington's Disease ABSTRACT: The scope of an acid-mediated sequential 3-component synthesis of thiadiazines was investigated. A selective functionalization of the six-membered heterocyclic core structure was accomplished by iterative alkylations, saponifications, and coupling reactions. Several new thiadiazines analogs showed activity in a cell based model of Huntington's Disease and low potency in biochemical histone deacetylase (HDAC) 1-8 counterassays.

Sulfamide-based heterocycles are attractive synthetic targets in medicinal chemistry; while they have a wide variety of biological activities, they have been relatively neglected in SAR studies, in part due to a dearth of synthetic methods, and therefore cyclic sulfamides still offer considerable opportunities in patent space. In addition to their function as urea bioisosteres, agents containing these building blocks have been shown to exhibit antibacterial, opioid receptor like-1 receptor (ORL1, NOP), colony stimulating factor-1 (CSF-1, implied in rheumatoid arthritis and metastatic bone cancer), and 11β-HSD1 (a target for type 2 diabetes) inhibitory activities. A subclass of sulfamide-containing heterocycles, 1,2,6-thiadiazine 1,1-dioxides, have been shown to act as cannabinoid agonists and antagonists and display modest antimicrobial activity, smooth muscle relaxation, and sedative effects. Additionally, the structurally related 2,1,3-benzothiadiazine-2,2-dioxides, such as the commercial herbicide bentazon, have demonstrated herbicidal activity.

The preparation of 1,2,6-thiadiazine 1,1-dioxides was first realized using an acid-mediated condensation of sulfamide and monoketones or β-diketones. Alternatively, functionalized thiadiazines have been prepared by base-mediated intramolecular cyclizations of sulfaminomethylene derivatives, condensation with substituted sulfamides and 3,3-diethoxypropane (1), condensation of sulfamide imines and 1, and the intramolecular Friedel-Crafts acylation of sulfamide iminium species. More recently, thiadiazines were prepared by joining an N,N'-dibenzylated sulfamide with 2-(acetoxymethyl)buta-2,3-dienoate, and by a silver- and gold-catalyzed hydroamination of propargyl sulfamides; but, overall, there is a surprising lack of 1,2,6-thiadiazine 1,1-dioxides with carboxylic acid substituents in the 4-position in the literature.

As part of the interests in the synthesis of novel heterocyclic compounds by multicomponent condensations (MCCs), it was envisioned that 1,2,6-thiadiazine 1,1-dioxides become readily available by a Biginelli-like MCC, and represent versatile scaffolds wherein the core heterocycle could be functionalized at several positions. Specifically, it was hypothesized that a variety of novel thiadiazines could be prepared by selective N-alkylations of the thiadiazine 1,1-dioxide core, followed by functional group interconversions of the 4-carboxylate ester. To this end, synthesis of the thiadiazine 1,1-dioxide core was investigated. The use of neat TFA as a solvent required long reaction times and gave inconsistent yields (Scheme 1, Equation 1). As a result, optimal thiadiazine formation conditions were sought. After considerable experimentation, it was found that condensation of sulfamide (2) with 1 in a 1:5 mixture of TFA and $CH_2Cl_2$ resulted in the formation of stable, crystalline 8-membered ring dimer 3 after 3 h at room temperature (Scheme 1, Equation 2). The unusual 8-membered ring structure and cis-configuration of dithiatetrazocane 3 was assigned based on an X-ray structure analysis (FIG. 1). Notably, there are very few compounds of similar connectivity in the literature.

Condensation of 3 with benzaldehyde in a 1:1 mixture of TFA and $CH_2Cl_2$ provided the desired thiadiazine 4a in 61% yield (Table 1, Entry 1). Alternative acidic conditions that were milder and provided 4a in a higher yield were also explored. Polyphosphate ester (PPE), $BF_3{\cdot}Et_2O$, triflamide, anhydrous HCl, methanesulfonic acid, and TFA:$CH_2Cl_2$ (1:5) yielded thiadiazine 4a in lower or comparable yields (Entries 2-7). When the quantity of TFA was reduced to 10 molar equivalents, the product was obtained in 59% yield (Entry 8). Further reduction of TFA to 2.5 molar equivalents were sufficient to obtain 4a in 57% yield if the reaction concentration was increased to 0.5 M and the mixture was heated to 40° C. for 30 h (Entry 9). Due to the limited solubility of the sulfamide dimer 3 in $CH_2Cl_2$ and the desire to increase the reaction rate, the solvent was changed to hexafluoroisopropanol (HFIP). It was envisioned that this non-nucleophilic alcohol with its remarkable hydrogen bond donor/acceptor capabilities would increase the dissolution of 3 and stabilize ionic intermediates, thus improving the conversion rate and product yield. However, the use of HFIP as a solvent in the presence of 2.5 equivalents of TFA provided a modest decrease of the reaction time while producing 4a in comparable yields (Entry 10).

Scheme 1. Precedent for thiadiazine 1,1-dioxide formation (Eq. 1) and preparation of dithiatetrazocane 3 (Eq. 2).

(1)

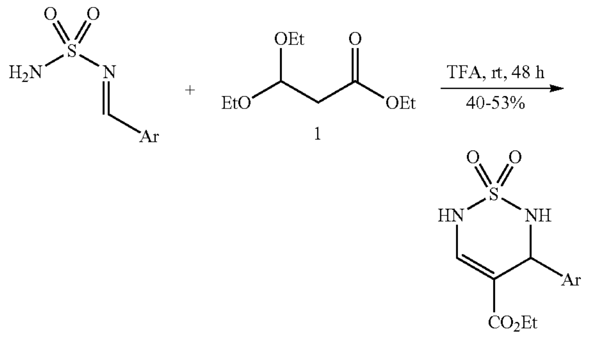

1

(2)

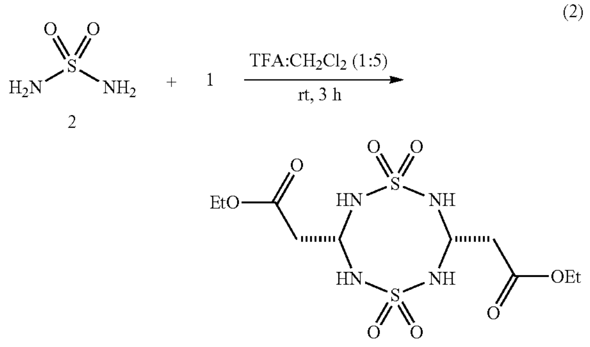

2

3
96% (>20g scale)

TABLE 1

Optimization of Thiadiazine 4a Formation from 3

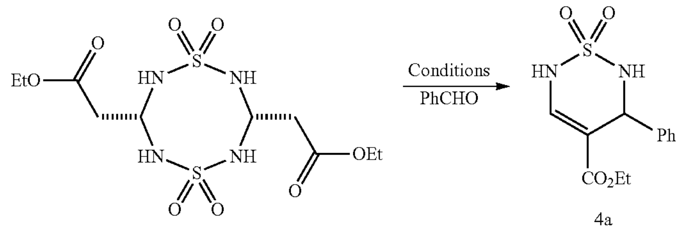

3
4a

| Entry | Conditions | Yield[a] |
|---|---|---|
| 1 | TFA:$CH_2Cl_2$ (1:1), rt, 30 min | 61% |
| 2 | PPE, THF, reflux, 40 min | 45% |
| 3 | $BF_3$•$OEt_2$ (2 equiv), $CH_2Cl_2$, rt, 6 h | 65% |
| 4 | 10% $Tf_2NH$, $CH_2Cl_2$, rt, 2.5 h | 42% |
| 5 | 4M HCl (10 equiv), dioxane, rt, 14 h | 47%[b] |
| 6 | $MeSO_3H$ (5.7 equiv), $CH_2Cl_2$, 0° C., 40 min | 39% |
| 7 | TFA:$CH_2Cl_2$ (1:5), rt, 3 h | 61% |
| 8 | TFA (10 equiv), $CH_2Cl_2$, rt, 60 h | 59% |
| 9 | TFA (2.5 equiv), $CH_2Cl_2$, 40° C., 30 h | 57%[c] |
| 10 | TFA (2.5 equiv), HFIP, 35-40° C., 17 h | 66%[d,e] |

[a]Isolated yield after chromatography on $SiO_2$;
[b]isolated in 85% purity;
[c]reaction was performed at 0.51M;
[d]reaction was performed at 0.50M;
[e]reaction in the absence of TFA led to the recovery of 81% of 3

Based on these optimizations, 10-20 molar equivalents of TFA in a solution of $CH_2Cl_2$ for further investigation was selected for the scope of compatible aldehydes in the thiadiazine 1,2-dioxide formation with 3 (Table 2). Aliphatic aldehydes (Entries 2-3), as well as electron deficient (Entries 4-8) and electron-rich aryl aldehydes (Entries 9-10) provided the cyclo-condensation products 4a-4j in 40-70% yield. The heterocyclic thiophene-3-carboxaldehyde provided 4k in a modest 30% yield (Entry 11). Other heterocyclic aldehydes (furans, quinolines, and pyridines) resulted in the formation of complex mixtures and were not further analyzed.

TABLE 2

Thiadiazine Formation with 3 and Various Aldehydes

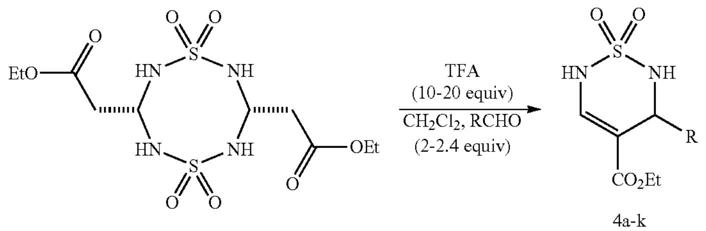

3 4a-k

| Entry | R | 4a-j | Yield[a] |
|---|---|---|---|
| 1 | Ph | 4a | 66%[b] |
| 2 | Me | 4b | 59% |
| 3 | Et | 4c | 56% |
| 4 | 2,4-$Cl_2C_6H_3$ | 4d | 70% |
| 5 | 4-$NCC_6H_4$ | 4e | 41% |
| 6 | 4-$MeCO_2C_6H_4$ | 4f | 57% |
| 7 | 4-$CF_3C_6H_4$ | 4g | 65% |
| 8 | 2-$BrC_6H_4$ | 4h | 45% |
| 9 | 4-$AcOC_6H_4$ | 4i | 48% |
| 10 | 3-$MeOC_6H_4$ | 4j | 62% |
| 11 | 3-thiophene | 4k | 30% |

[a]Isolated yield after chromatography on $SiO_2$;
[b]reaction was performed using TFA (2.5 equiv), HFIP, 35-40° C., 17 h Next, the possibility of regioselective sequential N-alkylation of the two sulfamide nitrogens was examined by exploiting their inherent difference in acidity (pKa[1] ca. 9.2 vs. pKa[2] ca. 9.5, i.e. the vinylogous carbamate sulfamide N(6)-H is calculated to be slightly more acidic) as well as their steric environment. Treatment of thiadiazine 4a with NaH followed by allyl iodide led to a mixture of mono- and di-alkylated products. In contrast, Mitsunobu conditions with allyl alcohol using DBAD led to a selective $(N)_6$-monoalkylation of thiadiazines 4a and 4b in good yields (Table 3, Entries 1-2). The regiochemistry was determined by NOESY correlations between the methylene hydrogens of the allyl group and the hydrogen of the thiadiazine alkene. Furanylmethanol required a change of the dialkylazodicarboxylate to DEAD, which simplified the purification (Entry 3). Simple or functionalized alkyl alcohols also gave good conversions (Entries 4, 5, and 7). While the yield was slightly lower with 1,4-phenylenedimethanol, monoalkylated product 5h was readily isolated (Entry 8), and a Boc-protection was also highly selective and generated thiadiazine 1,2-dioxide 5i in 86% yield (Entry 9). A symmetrical dialkylation was straightforward by treating 4a with an excess of MeI in the presence of $K_2CO_3$ to give 6f in excellent yield (Entry 6).

The alkylation of the thiadiazine N(2) amide was investigated next. Benzylations of 5a and 5b were achieved in the presence of NaH and TBAI to provide 6a and 6b in 68 and 71% yield, respectively (Table 4, Entries 1-2).

TABLE 3
Regioselective N(6)-Alkylation of Thiadiazines 4a-d
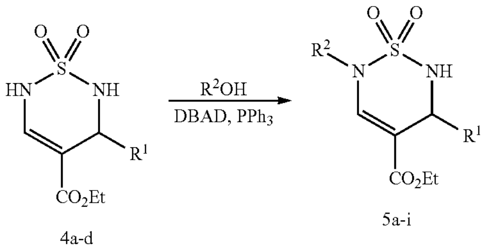
4a-d
5a-i
| Entry | 4 | $R^2OH$ | Yield | Product |
|---|---|---|---|---|
| 1 | 4a | 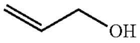 | 77% | 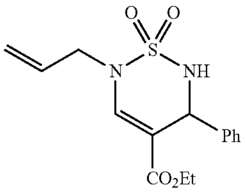 [SMILES: C=CCN1C=C(C(=O)OCC)C(c2ccccc2)NS1(=O)=O] 5a |
| 2 | 4b | 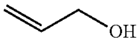 | 72% | 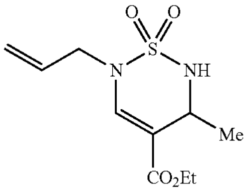 5b |
| 3 | 4c | 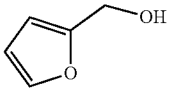 | 37%[a] | 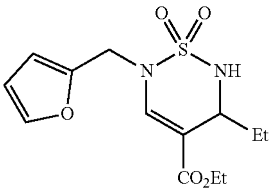 [SMILES: CCOC(=O)C1=CN(Cc2ccco2)S(=O)(=O)NC1CC] 5c |
| 4 | 4a | 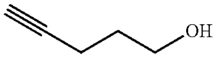 | 58% | 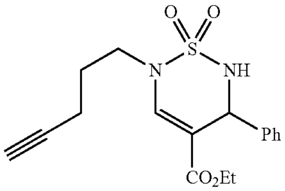 [SMILES: C#CCCCN1C=C(C(=O)OCC)C(c2ccccc2)NS1(=O)=O] 5d |
| 5 | 4a | EtOH | 75% | 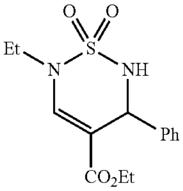 5e |

TABLE 3-continued
Regioselective N(6)-Alkylation of Thiadiazines 4a-d
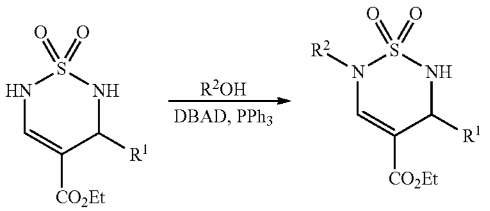
4a-d
5a-i
| Entry | 4 | $R^2OH$ | Yield | Product |
|---|---|---|---|---|
| 6 | 4a | MeI | Quant[b] | 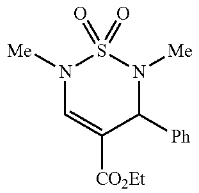 6f |
| 7 | 4d | 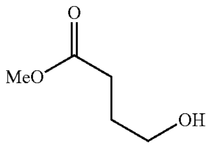 | 53% | 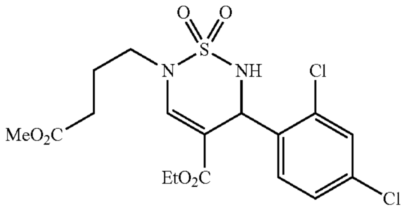 [SMILES: CCOC(=O)C1=CN(CCCC(=O)OC)S(=O)(=O)NC1c1ccc(Cl)cc1Cl] 5g |
| 8 | 4d | 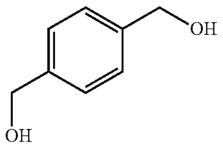 | 52% | 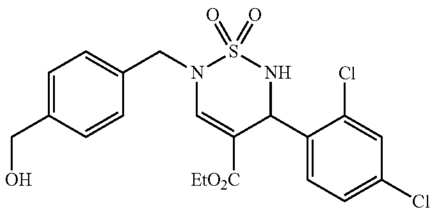 [SMILES: CCOC(=O)C1=CN(Cc2ccc(CO)cc2)S(=O)(=O)NC1c1ccc(Cl)cc1Cl] 5h |
| 9 | 4d | $Boc_2O$ | 86%[c] | 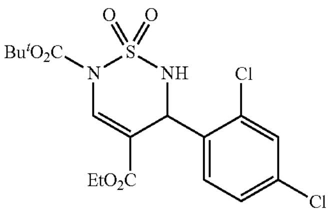 5i |
[a]DEAD was used in place of DBAD;
[b]4a was treated with MeI (5 equiv), $K_2CO_3$, MeCN;
[c]reaction with 4d (1.1 equiv), $Boc_2O$ (1 equiv), and $K_2CO_3$ (2.5 equiv)

N-Methylations of 5c-e were achieved with $K_2CO_3$ in MeCN and produced 6c-e in high yields (Table 4, Entries 3-5). An ester-functionalized benzyl bromide was similarly successfully introduced to generate the Boc-protected diester 6i (Entry 6).

TABLE 4

N(2)-Alkylation of Thiadiazines 5

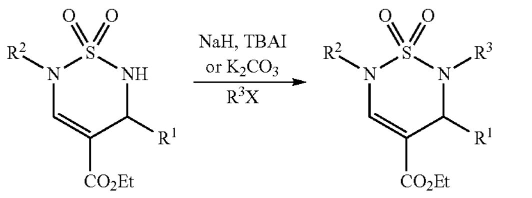

5a-i 6a-i

| Entry | 5 | $R^3X$ | Yield | Product 6 |
|---|---|---|---|---|
| 1 | 5a | BnBr | 68%[a] | 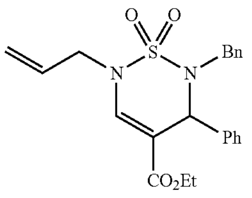 [SMILES: C=CCN1C=C(C(=O)OCC)C(c2ccccc2)N(Cc2ccccc2)S1(=O)=O] 6a |
| 2 | 5b | BnBr | 71%[a] | 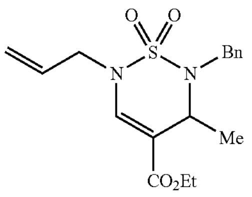 [SMILES: C=CCN1C=C(C(=O)OCC)C(C)N(Cc2ccccc2)S1(=O)=O] 6b |
| 3 | 5c | MeI | 91%[b] | 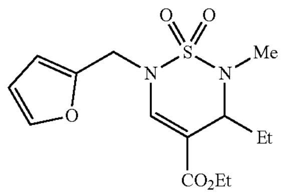 6c |
| 4 | 5d | MeI | 98%[b] | 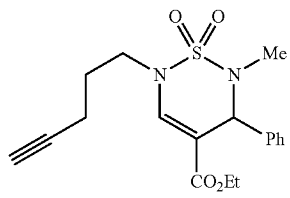 [SMILES: C#CCCCN1C=C(C(=O)OCC)C(c2ccccc2)N(C)S1(=O)=O] 6d |

TABLE 4-continued

N(2)-Alkylation of Thiadiazines 5

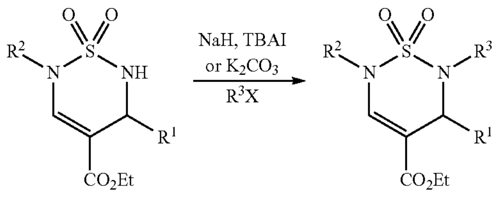

5a-i 6a-i

| Entry | 5 | $R^3X$ | Yield | Product 6 |
|---|---|---|---|---|
| 5 | 5e | MeI | Quant[b] | 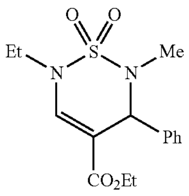 [SMILES: CCOC(=O)C1=CN(CC)S(=O)(=O)N(C)C1c1ccccc1] 6e |
| 6 | 5i | 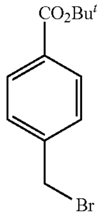 | 79%[b] | 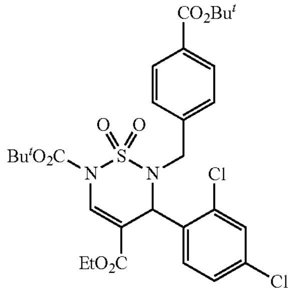 6i |

[a]NaH, TBAI, THF;
[b]$K_2CO_3$, MeCN

For additional chemical scaffold diversifications, selective conversions of the C(4)-esters (Scheme 2) was investigated. Initial attempts at a Lewis acid mediated transesterification, or a mild hydrolysis using TMSOK or $Bu_3SnOH$, were unsuccessful. However, ester hydrolysis was achieved by heating 5e, 6e, 6f, and 5g in 2 M KOH in EtOH to provide acids 7e, 8e, 8f and 9g, respectively. Under milder conditions with LiOH in THF, MeOH and water at room temperature, the aliphatic carboxylate in 5g was saponified selectively, and 7g was isolated in quantitative yield. Furthermore, diacid 9g could be selectively re-esterified to the monomethyl ester 10g under Fischer conditions, thus allowing for a regiospecific conversion of the carboxylate functional groups in diester 5g. Finally, a Curtius rearrangement of thiadiazine 8f with DPPA afforded the tert-butyl carbamate 11f, providing the first entry to this unprecedented thiadiazine 1,1-dioxide substitution pattern.

Jones oxidation of the side chain alcohol in 5h provided benzoic acid 7h in 94% yield, and treatment of 6i with TFA generated the regioisomeric benzoate 10i with concomitant removal of the Boc-group (Scheme 3). These transformations added additional versatility and valuable sites for diversifications to the collection of thiadiazine 1,1-dioxide building blocks.

Scheme 2. Saponification of Mono- and Dialkylated Thiaidiazines and Curtius Rearrangement of Carboxylate 8f.

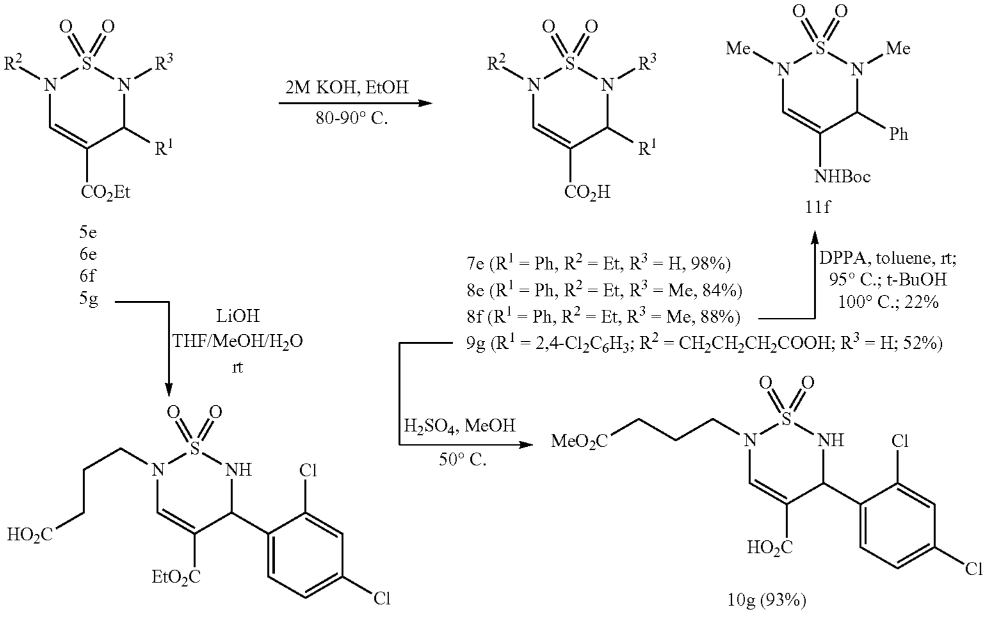

5e
6e
6f
5g

11f 7e ($R^1$ = Ph, $R^2$ = Et, $R^3$ = H, 98%)
8e ($R^1$ = Ph, $R^2$ = Et, $R^3$ = Me, 84%)
8f ($R^1$ = Ph, $R^2$ = Et, $R^3$ = Me, 88%)
9g ($R^1$ = 2,4-$Cl_2C_6H_3$; $R^2$ = $CH_2CH_2CH_2COOH$; $R^3$ = H; 52%)

10g (93%)

7g (quant.)

Scheme 3. Selective Formations of Mono-acid Thiadiazine 1,1-dioxides.

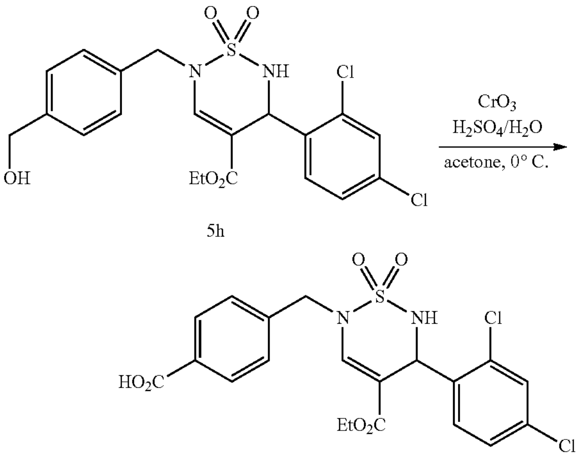

5h 7h (94%)

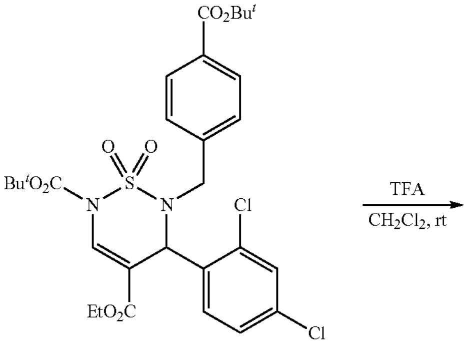

6i

-continued

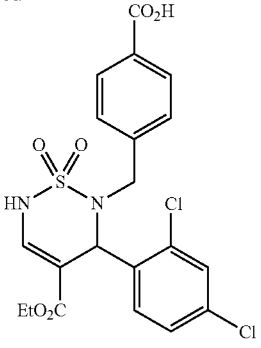

10i (98%)

In order to demonstrate the utility of these building blocks for the preparation of bioactive screening samples, a series of amide and ester analogs was generated, and subjected to a representative biological assay. Amide bond formation using PyBOP and DIPEA, or EDCI, DMAP, and DIPEA, with pyridinyl methanamine proceeded in good yield with thiadiazines 7e and 8e to give 11e and 13e (Table 5, Entries 1 and 4). Hydroxamic acids 12g and 12h were obtained by coupling of carboxylic acids 7g and 7h, respectively, with THP-protected hydroxylamine in the presence of $T_3P$ and TEA, followed by cleavage of the THP group with Amberlyst-15 resin (Entries 2 and 3). p-Methoxybenzylamine, N,N-dimethylethylenediamine, and morpholine yielded amides 14e, 15e, and 16e (Entries 5-7). The formation of hydroxamic esters 17e and 17f and benzyl ester 18g also occurred in moderate to high yield (Entries 8-10). Furthermore, methyl hydroxamate 17f was selectively reduced to the aldehyde 19f (Scheme 4). It was anticipated that this aldehyde would allow access to secondary amines by reductive amination. While one-pot imine formation-reduction conditions were unsuccessful, sequential imine formation using $Ti(i\text{-}PrO)_4$ followed by reduction with $NaBH_4$ provided amines 20f and 21f in 69% and 65% overall yield from 19f.

TABLE 5
Amidation and Esterification of Acids 7, 8, and 10
| Entry | Acid | Amine/Alcohol | Amide/Ester 11-18 |
|---|---|---|---|
| 1 | 7e | 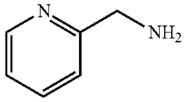 | 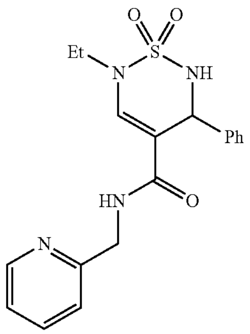<br>11e (72%)[a] |
| 2 | 7g | 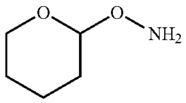 | 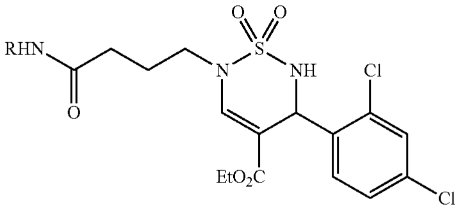<br>c<br>11g (R = OTHP, 77%)[b]<br>12g (R = OH, 53%) |
| 3 | 7h | 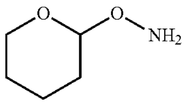 | 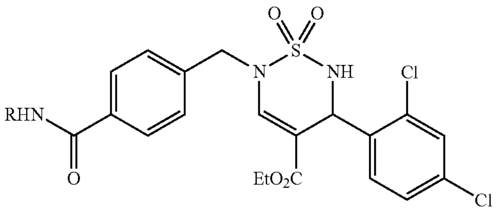<br>c<br>11h (R = OTHP, 81%)[b]<br>12h (R = OH, 82%) |
| 4 | 8e | 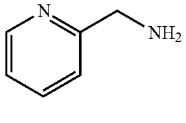 | 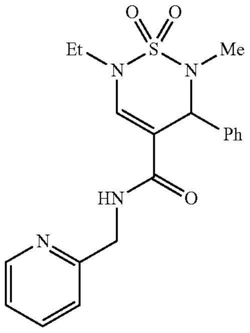<br>13e (85%)[d] |

TABLE 5-continued
| Entry | Acid | Amine/Alcohol | Amide/Ester 11-18 |
|---|---|---|---|
| Amidation and Esterification of Acids 7, 8, and 10 | | | |
| 5 | 8e | 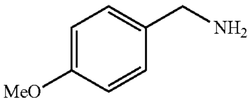 | 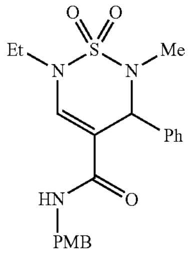 14e (83%)[d] |
| 6 | 8e | 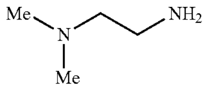 | 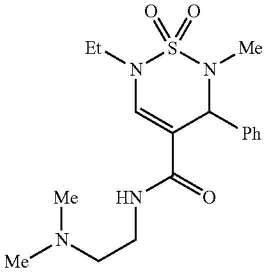 15e (76%)[d] |
| 7 | 8e | 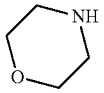 | 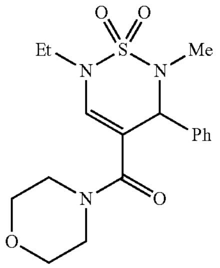 16e (84%)[d] |
| 8 | 8e | MeNH(OMe)•HCl | 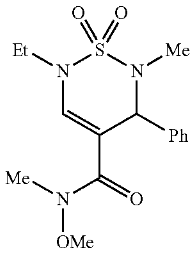 17e (90%)[d] |
| 9 | 8f | MeNH(OMe)•HCl | 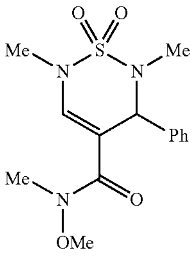 17f (94%)[d] |

TABLE 5-continued

| Amidation and Esterification of Acids 7, 8, and 10 | | | |
|---|---|---|---|
| Entry | Acid | Amine/Alcohol | Amide/Ester 11-18 |
| 10 | 10g | 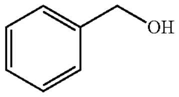 | 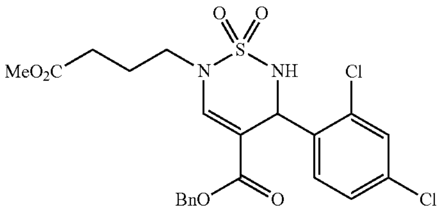 18g (60%)[a] |

[a]Coupling with EDCI, DMAP, DIPEA;
[b]$T_3P$ and TEA;
[c]Amberlyst-15, MeOH, rt;
[d]coupling with PyBOP, DIPEA Scheme 4. Reduction of Hydroxamide 17f and Reductive Amination of Aldehyde 19f.

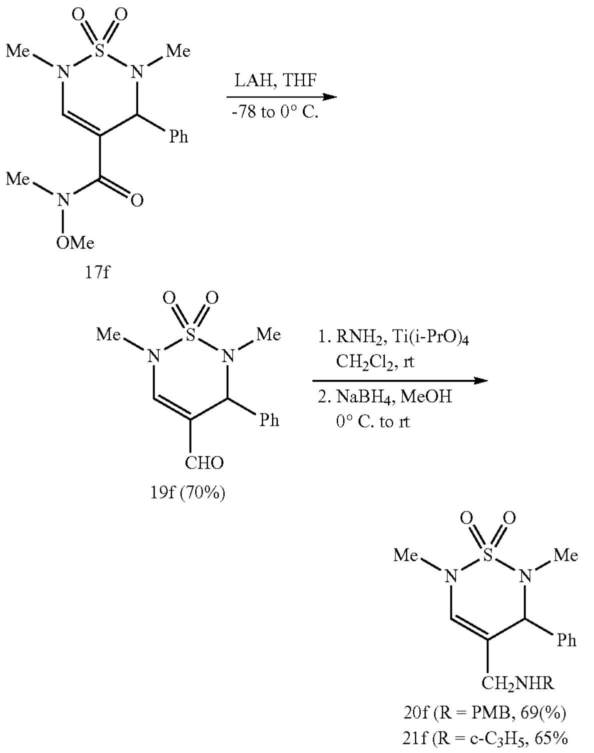

After developing a versatile strategy and reaction conditions for the preparation and sequential functionalization of thiadiazine 1,1-dioxides, the biological activity of the compound was investigated. Specifically, it was explored if thiadiazine 1,1-dioxides could serve as agonist of Hsp70 that reduces protein aggregation associated with neurodegenerative diseases. Therefore, ten structurally closely related analogs were selected for a cell-based screen in a Huntington's Disease (HD) model (FIG. 2).

Ten analogs, 5g, 5h, 6i, 7h, 9g, 10g, 10i, 12g, 12h, and 18g, were investigated for their ability to blunt the formation of toxic aggregates in HEK293 cells that express an HTT exon containing 17 glutamine repeats. Several analogs reduced the number of cellular puncta/aggregates compared to the DMSO control. Cells were stained for confocal microscope imaging with 4',6-diamidino-2-phenylindole (DAPI), a fluorescent dye with high affinity to adenine-thymine rich DNA regions. A bright spot detection tool was used to identify and quantify the number of protein aggregates ("dots") per cell.

Figure 2:
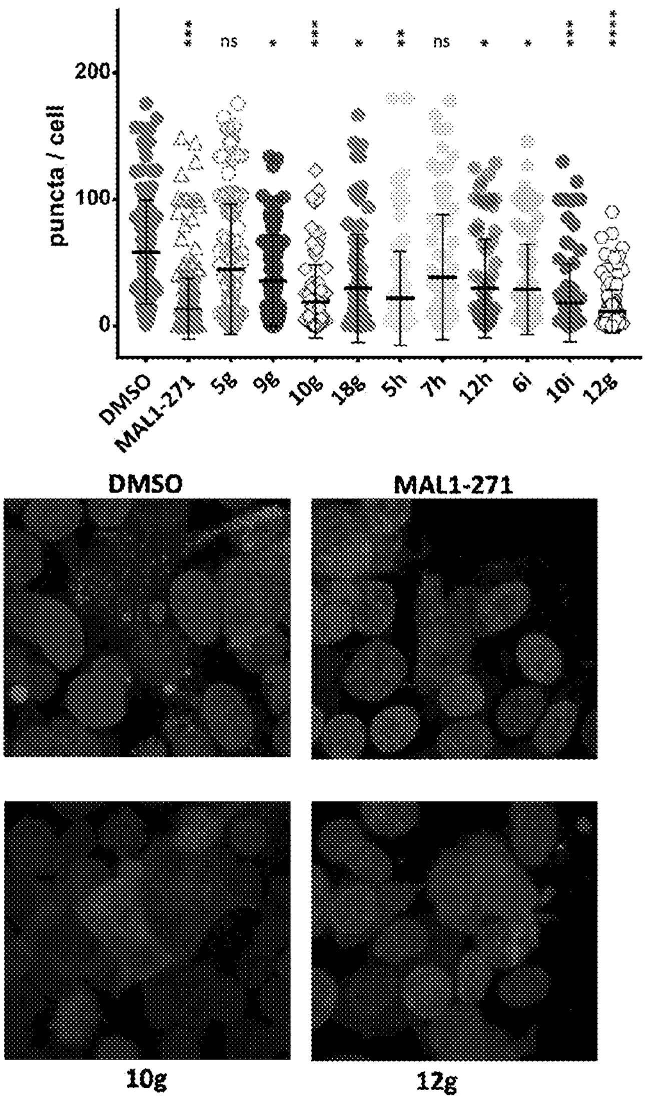
FIG. 2 shows graphs and images of HEK293H cells transfected with 4 μg of an HTT17Q-mCherry construct, and 24 h after transfection cells were treated with 10 μM compound or DMSO for 6 h. Top panel shows number of puncta per cell. Statistically significant differences between control and treated samples are indicated by asterisks. * $p<0.05$;  $p<0.005$; * $p<0.0005$; **** $p<0.00005$ compared to the DMSO control. Bottom panel shows representative cell images for negative control (DMSO), positive control (MAL1-271), and analogs 10g and 12g.
Figure 3:
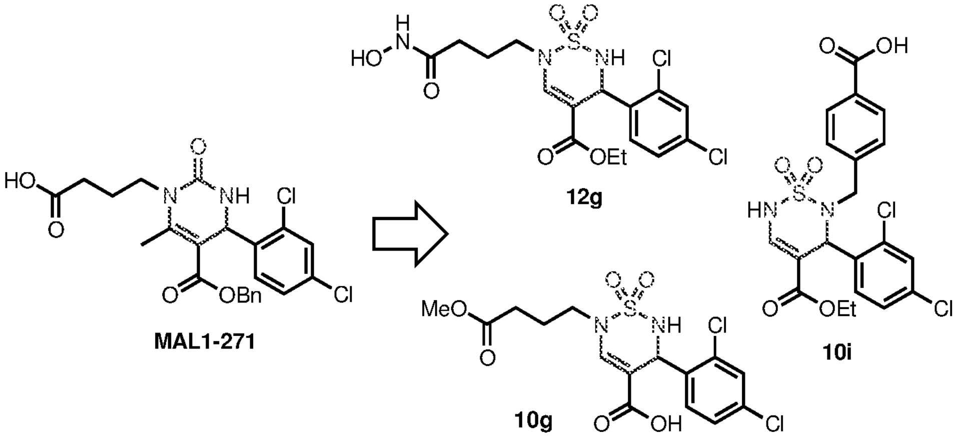
FIG. 3 shows structures of Hsp70 agonist MAL1-271 and thiadiazine 1,1-dioxide analogs that showed similar activity in the HD model assay. The respective Biginelli (dihydropyrimidinone) and thiadiazine scaffolds are highlighted.

Compared to the MAL1-271 positive control, 5g, 9g, 18g, 5h, 7h, 12h, and 6i were less effective ($p<0.0001$), whereas 10g and 10i were equally effective (FIG. 2). Thiadiazine 12g exhibited even a slightly greater effect on aggregate suppression than MAL1-271 ($p<0.05$). the compounds (especially 10g and 10i) represent novel heterocycle substitution patterns that can serve as starting points for new structure-activity studies (FIG. 3).

It is also interesting to note that 12g is a hydroxamic acid analog of MAL1-271; in order to address the possibility that 12g or another analog exerted anti-aggregation effects due to inhibition of a histone deacetylase (HDAC), actives 10g, 10i, 12g, and 12h (negative control) against HDAC 1-8 (Table 6) were counter-screened. None of the active compounds displayed >20% HDAC 1-4 inhibition at 1 μM concentration, or HDAC 5/7 inhibition at 0.2/0.1 μM, the highest tested concentrations for these targets. Only the negative control, hydroxamic acid 12h, showed 40% inhibition of HDAC 7 at 1 μM, and all compounds showed moderate inhibition (35-60%) of HDAC 8 at 1 μM concentration in the assay. The absence of a clear correlation between HDAC inhibition and activity in the HD assay for hydroxamates 12g and 12h suggests that the active hit compound 12g did not reduce cellular HTT aggregates due to direct HDAC inhibition. Moreover, HDAC6, which has been implicated in the heat shock protein gene expression, was also not inhibited by hydroxamates 12g and 12h at 0.2 μM concentration. However, since the biochemical assays at higher concentrations were prevented by low aqueous solubility, the possibility of a mechanism of action involving HDAC inhibition in HEK293H cells at 10 μM concentration cannot be excluded.

Methods: All glassware was flame dried or oven-dried and cooled under dry $N_2$ or Ar prior to use. All moisture sensitive reactions were performed under dry $N_2$ or Ar. Reactions carried out below 0° C. employed an acetone/dry ice bath or a cyrocool and an isopropanol/ethanol bath. Reagents obtained from commercial sources were used as received unless otherwise specified. THF, $Et_2O$, and 1,4-dioxane were distilled from sodium/benzophenone ketyl; DIPEA and TEA were distilled from $CaH_2$ and stored over KOH; t-BuOH was distilled over $CaH_2$; and $CH_2Cl_2$ and toluene were purified by passage through an activated alumina filtration system. HFIP was distilled from 4 Å MS and stored over 4 Å MS. Benzaldehyde was distilled under vacuum (~30 mmHg) immediately prior to use. Concentrating under reduced pressure refers to the use of a rotary evaporator connected to a membrane vacuum pump to remove solvent.

Melting points were determined using a Laboratory Devices Mel-Temp II in open capillary tubes and are uncorrected. Infrared spectra were determined as neat solids or oils (unless otherwise specified) on a Smiths Detection Identify IR FT-IR spectrometer or Perkin Elmer Spectrum 100; or as KBr pellets or thin films on a Nicolet Avatar 360 FT-IR. Low-resolution mass spectra were obtained on a Shimadzu 2020-LCMS or Agilent Technologies 1260 Infinity II LCMS. High-resolution mass spectra were obtained on a Micromass UK Limited, Q-TOF Ultima API or a Thermo Scientific Exactive Orbitrap LCMS. Purity of compounds tested in biological assays was assessed using an Agilent Technologies 1260 Infinity II LC at 220 nm UV absorption (Waters XBridge BEH $C_{18}$ 2.1×50 mm, 2.5 μm) or an Agilent Technologies 385-ELSD (Microsolv Cogent 2.0 Bidentate $C_{18}$ 2.1×50 mm, 2.2 μm; ELSD conditions: evaporator and nebulizer set at 45° C.; gas flow set at 1.80 standard liter/min).

$^1H$ and $^{13}C$ NMR spectra were recorded on a Bruker Avance III 300 MHz, 400 MHz, 500 MHz, and a cryoprobe equipped 600 MHz instruments. $CDCl_3$ was filtered through basic $Al_2O_3$ immediately prior to sample preparation. Chemical shifts (δ) were reported in parts per million with the residual solvent peak used as an internal standard δ $^1H/^{13}C$ (Solvent); 7.26/77.16 ($CDCl_3$); 2.50/39.52 (DMSO-$d_6$); 2.05/29.84 (acetone-$d_6$) and are tabulated as follows: chemical shift, multiplicity (s=singlet, bs=broad singlet, d=doublet, t=triplet, q=quartet, m=multiplet), number of protons, and coupling constant(s). $^{13}C$ NMR spectra were obtained at 75 MHz, 100 MHz, and 125 MHz using a proton-decoupled pulse sequence and are tabulated by observed peak. Thin-layer chromatography was performed using pre-coated silica gel 60 $F_{254}$ plates (EMD, 250 μm thickness) and visualization was accomplished with a 254 nm UV light and by staining with a phosphomolybdic acid solution (5 g of phosphomolybdic acid in 100 mL of 95% EtOH), a p-anisaldehyde solution (2.5 mL of p-anisaldehyde, 2 mL of AcOH, and 3.5 mL of conc. $H_2SO_4$ in 100 mL of 95% EtOH), a $KMnO_4$ solution (1.5 g of $KMnO_4$ and 1.5 g of $K_2CO_3$ in 100 mL of a 0.1% NaOH solution), or Vaughn's reagent (4.8 g of $(NH_4)_6Mo_7O_{24}\cdot 4H_2O$ and 0.2 g of $Ce(SO_4)_2$ in 100 mL of a 3.5 N $H_2SO_4$ solution). Flash chromatography on $SiO_2$ (Silicycle, Silia-P Flash Silica Gel or SiliaFlash® P60, 40-63 μm) was used to purify crude reaction mixtures.

Experimental Procedures

3

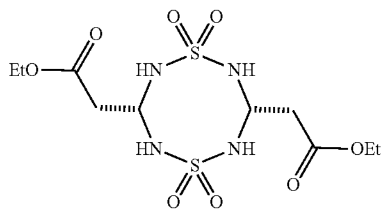

Diethyl 2,2'-((3SR,7SR)-1,1,5,5-tetraoxido-1,5,2,4,6,8-dithiatetrazocane-3,7-diyl)diacetate (3). To a suspension of sulfamide 2 (11.0 g, 113 mmol) in $CH_2Cl_2$ (217 mL) and TFA (44.0 mL, 586 mmol) was added diethoxypropionate 1 (25.5 mL, 125 mmol) over 5 min. The solution was stirred for 4 h at rt, filtered through a medium glass fritted funnel, washed with $CH_2Cl_2$ (~60 mL), MeOH (~50 mL), and $Et_2O$ (~50 mL), and dried under high vacuum to give 3 (21.2 g, 96%) as a colorless solid: Mp 183-183° C. ($CH_2Cl_2$); IR (ATR) 3318, 2990, 1717, 1348, 1335, 1048 $cm^{-1}$; $^1H$ NMR (DMSO-$d_6$, 400 MHz) δ 7.52 (d, 4H, J=9.4 Hz), 5.18 (ddt, 2H, J=9.2, 9.2, 7.3 Hz), 4.06 (q, 4H, J=7.1 Hz), 2.64 (d, 4H, J=7.2 Hz), 1.18 (t, 6H, J=7.1 Hz); $^{13}C$ NMR (DMSO-$d_6$, 100 MHz) δ 168.5, 62.1, 60.2, 41.1, 14.0; HRMS ($ESI^+$) m/z calcd for $C_{10}H_{21}N_4O_8S_2$ $[M+H]^+$ 389.0801, found 389.0779.

4a

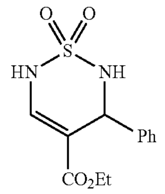

Ethyl 3-phenyl-3,6-dihydro-2H-1,2,6-thiadiazine-4-carboxylate 1,1-dioxide (4a). To a suspension of sulfamide 3 (9.76 g, 25.1 mmol) and benzaldehyde (5.20 mL, 51.2 mmol) in HFIP (100 mL) was added dropwise TFA (9.65 mL, 126 mmol). The solution was stirred at 35-40° C. in a round bottom flask capped with a glass stopper for 17 h. The solvent was evaporated under reduced pressure to give a yellow oil that was purified by chromatography on $SiO_2$ (2:8 to 4:6; EtOAc:hexanes) to give the thiadiazine 4a (9.33 g, 66%) as a colorless solid: Mp 144-145° C. ($CHCl_3$); IR (ATR) 3269, 3176, 2980, 1655, 1150, 1100 $cm^{-1}$; $^1H$ NMR (DMSO-$d_6$, 400 MHz) δ 10.82 (s, 1H), 7.93 (d, 1H, J=7.2 Hz), 7.49 (s, 1H), 7.31-7.21 (m, 5H), 5.33 (d, 1H, J=7.2 Hz), 4.01, 3.96 (dq, 2H, J=10.9, 7.1 Hz), 1.04 (t, 3H, J=7.1 Hz); $^{13}C$ NMR (DMSO-$d_6$, 100 MHz) δ 165.2, 139.0, 138.8, 127.9, 127.8, 127.3, 102.8, 59.6, 57.5, 14.0; HRMS ($ESI^+$) m/z calcd for $C_{12}H_{14}N_2O_4S$ $[M+H]^+$ 283.0753, found 283.0786.

SFC Separation: Chiral IA, run time 6.08 min; Peak A: 2.57 min, $[\alpha]_D$ −8.1 (c 0.16, $CH_2Cl_2$); Peak B: 3.08 min, $[\alpha]_D$+9.0 (c 0.13, $CH_2Cl_2$).

General Procedure A: Ethyl 3,6-dihydro-2H-1,2,6-thiadiazine-4-carboxylate 1,1-dioxide. To a stirred suspension of sulfamide dimer 3 (50 mg, 0.13 mmol) and aldehyde (0.26 mmol) in $CH_2Cl_2$ (2.0 mL) was added TFA (0.190 mL, 2.56 mmol) dropwise at rt. The suspension was stirred for 16 to 48 h while the solution turned clear. The reaction mixture was concentrated under reduced pressure and the residue was purified by chromatography on $SiO_2$ (EtOAc:hexanes) to give the desired ethyl 3,6-dihydro-2H-1,2,6-thiadiazine-4-carboxylate 1,1-dioxide.

4b

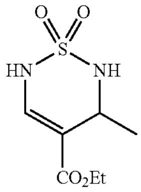

Ethyl 3-methyl-3,6-dihydro-2H-1,2,6-thiadiazine-4-carboxylate 1,1-dioxide (4b). According to General Procedure A, sulfamide 3 (2.00 g, 5.15 mmol), acetaldehyde (0.580 mL, 10.3 mmol), and TFA (7.73 mL, 101 mmol) were stirred at rt for 26 h and provided a crude residue that was purified by chromatography on $SiO_2$ (15:85 to 3:7; EtOAc:hexanes) to give 4b (1.34 g, 59%) as a colorless oil: IR (KBr) 1693, 1274, 1163 $cm^{-1}$; $^1H$ NMR (DMSO-$d_6$, 300 MHz) δ 10.61 (d, 1H, J=4.2 Hz), 7.60 (d, 1H, J=6.9 Hz), 7.20 (d, 1H, J=4.5 Hz), 4.25-3.95 (m, 3H), 1.37 (d, 3H, J=7.2 Hz), 1.19 (t, 3H, J=7.2 Hz); $^{13}C$ NMR (DMSO-$d_6$, 150 MHz) δ 164.9, 135.4, 107.8, 60.0, 51.6, 18.5, 13.5; MS (EI) m/z 220 ($M^+$); HRMS (EI) m/z calcd for $C_7H_{12}N_2O_4S$ [$M^+$] 220.0517, found 220.0518.

4c

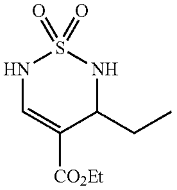

Ethyl 3-ethyl-3,6-dihydro-2H-1,2,6-thiadiazine-4-carboxylate 1,1-dioxide (4c). According to General Procedure A, sulfamide 3 (2.00 g, 5.15 mmol), propanal (0.900 mL, 12.4 mmol), and TFA (7.65 mL, 103 mmol) were stirred at rt for 24 h and provided a crude residue that was purified by chromatography on $SiO_2$ (100% hexanes to 35:65; EtOAc: hexanes) to give 4c (1.34 g, 56%) as a colorless solid: Mp 128-130° C.; IR (ATR) 3288, 3148, 1657, 1638, 1299, 1156 $cm^{-1}$; $^1H$ NMR (400 MHz, DMSO-$d_6$) δ 10.60 (d, 1H, J=5.6 Hz), 7.52 (d, 1H, J=6.6 Hz), 7.21 (d, 1H, J=5.8 Hz), 4.11 (dq, 1H, J=7.1, 3.7 Hz), 4.07 (dq, 1H, J=7.1, 3.8 Hz), 3.92 (ddd, 1H, J=10.8, 6.6, 3.8 Hz), 1.90-1.78 (m, 1H), 1.72-1.62 (m, 1H), 1.94 (t, 3H, J=7.1 Hz), 0.92 (t, 3H, J=7.2 Hz); $^{13}C$ NMR (100 MHz, DMSO-$d_6$) δ 165.3, 137.1, 104.9, 59.6, 56.7, 24.7, 14.2, 10.7; HRMS (ESI-ASAP) m/z calcd for $C_8H_{13}N_2O_4S$ $[M-H]^-$ 233.0596, found 233.0592.

4d

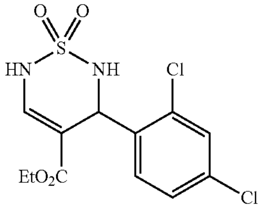

Ethyl 3-(2,4-dichlorophenyl)-3,6-dihydro-2H-1,2,6-thiadiazine-4-carboxylate 1,1-dioxide (4d). To a suspension of 3 (1.85 g, 4.69 mmol) in HFIP (18.5 mL) was added 2,4-dichlorobenzaldehyde (1.68 g, 9.38 mmol) and TFA (1.81 mL, 23.5 mmol) dropwise. The reaction mixture was stirred for 19 h at 35-40° C. The yellow solution was diluted with $CH_2Cl_2$, quenched with $NaHCO_3$ (20 mL), and the aqueous layer was extracted with $CH_2Cl_2$ (2×20 mL). The combined organic layers were washed with brine (40 mL) and concentrated to afford 4d (1.23 g, 73%) as an off-white solid: Mp 191-202° C.; IR (ATR) 3270, 3174, 2833, 1666, 1636 $cm^{-1}$; $^1H$ NMR (400 MHz, DMSO-$d_6$) δ 11.0 (bs, 1H) 8.17 (d, 1H, J=7.2 Hz) 7.62 (d, 1H, J=2 Hz), 7.59 (bs, 1H) 7.36 (dd, 1H, J=8.4, 2.0 Hz) 7.21 (d, 1H, J=8.4 Hz), 5.60 (d, 1H, J=7.2 Hz), 3.98 (dq, 2H, J=11.2, 7.3 Hz), 1.05 (t, 3H, J=7.2 Hz); $^{13}C$ NMR (100 MHz, DMSO-$d_6$) δ 164.8, 139.8, 135.1, 134.0 133.1, 131.4, 128.7, 126.7, 101.2, 59.8, 54.0, 14.0); HRMS ($ESI^+$) m/z calcd for $[M+H]^+$ 350.9973, found 350.9944.

4e

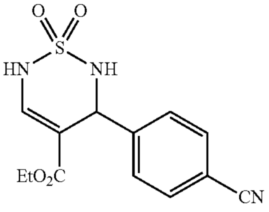

Ethyl 3-(4-cyanophenyl)-3,6-dihydro-2H-1,2,6-thiadiazine-4-carboxylate 1,1-dioxide (4e). According to General Procedure A, sulfamide 3 (0.050 g, 0.13 mmol), 4-formylbenzenecarbonitrile (0.0360 mL, 0.261 mmol), and TFA (0.100 mL, 1.31 mmol) were stirred at rt for 22 h. The reaction was incomplete, and TFA (0.100 mL, 1.31 mmol) was added. The reaction mixture was stirred for another 24 h and provided a crude residue that was purified by chromatography on $SiO_2$ (1:3 to 35:65; EtOAc:hexanes) to give 4e (0.0320 g, 41%) as a colorless solid: Mp 185-186° C.; IR (KBr) 1698, 1268, 1156 $cm^{-1}$; $^1H$ NMR (DMSO-$d_6$, 300 MHz) δ 11.02 (s, 1H), 8.15 (d, 1H, J=7.2 Hz), 7.76 (d, 2H, J=8.4 Hz), 7.56 (s, 1H), 7.43 (d, 2H, J=8.4 Hz), 5.41 (d, 1H, J=7.2 Hz), 4.07-3.99 (m, 2H), 1.07 (t, 3H, J=7.2 Hz); $^{13}C$ NMR (DMSO-$d_6$, 150 MHz) δ 165.0, 144.8, 139.5, 131.7, 128.9, 118.8, 110.0, 101.4, 59.7, 56.6, 14.0; MS (EI) m/z 307 ($M^+$, 60), 242 ($[M-SO_2]^+$, 90); HRMS (EI) m/z calcd for $C_{13}H_{13}N_3O_4S$ [$M^+$] 307.0627 found 307.0623.

4f

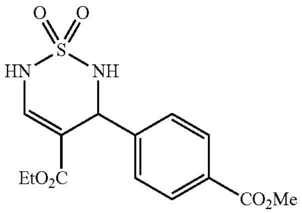

Ethyl 3-(4-(methoxycarbonyl)phenyl)-3,6-dihydro-2H-1,2,6-thiadiazine-4-carboxylate 1,1-dioxide (4f). According to General Procedure A, sulfamide 3 (0.050 g, 0.13 mmol), methyl 4-formylbenzoate (0.047 g, 0.26 mmol), and TFA (0.190 mL, 2.48 mmol) were stirred at rt for 20 h and provided a crude residue that was purified by chromatography on $SiO_2$ (100% hexanes to 35:65; EtOAc:hexanes) to give 4f (49.4 mg, 57%) as a colorless solid: Mp 176-178° C.;

IR (KBr) 1700, 1286, 1159 $cm^{-1}$; $^{1}H$ NMR (DMSO-$d_6$, 600 MHz) 10.98 (s, 1H), 8.12 (d, 1H, J=7.2 Hz), 7.93 (d, 2H, J=8.2 Hz), 7.59 (s, 1H), 7.43 (d, 2H, J=8.4 Hz), 5.44 (d, 1H, J=6.6 Hz), 4.09-4.01 (m, 2H), 3.88 (s, 3H), 1.11 (t, 3H, J=7.2 Hz); $^{13}C$ NMR (DMSO-$d_6$, 150 MHz) δ 166.1, 165.0, 144.5, 139.3, 128.7, 128.6, 128.2, 101.9, 59.7, 56.8, 52.1, 14.0; MS (EI) m/z 340 ($M^+$, 15), 275 ($[M-SO_2]^+$, 100); HRMS (EI) m/z calcd for $C_{14}H_{16}N_2O_6S$ [$M^+$ ] 340.0729, found 340.0727.

4g

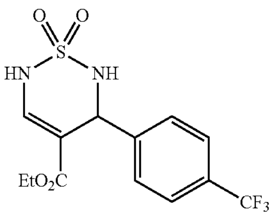

Ethyl 3-(4-(trifluoromethyl)phenyl)-3,6-dihydro-2H-1,2,6-thiadiazine-4-carboxylate 1,1-dioxide (4g). According to General Procedure A, sulfamide 3 (1.00 g, 2.57 mmol), 4-(trifluoromethyl)benzaldehyde (0.850 mL, 6.20 mmol), and TFA (3.80 mL, 49.6 mmol) were stirred at rt for 36 h and provided a crude residue that was purified by chromatography on $SiO_2$ (100% hexanes to 35:65; EtOAc:hexanes) to give 4g (1.17 g, 65%) as a colorless solid: Mp 179-181° C.; IR (KBr) 1696, 1280, 1163 $cm^{-1}$; $^{1}H$ NMR (DMSO-$d_6$, 600 MHz) δ 10.98 (s, 1H), 8.14 (d, 1H, J=6.6 Hz), 7.68 (d, 1H, J=7.8 Hz), 7.57 (s, 1H), 7.48 (d, 1H, J=7.8 Hz), 5.44 (d, 1H, J=7.6 Hz), 4.12-3.99 (m, 2H), 1.08 (t, 3H, J=7.2 Hz); $^{13}C$ NMR (MeOD-$d_4$, 150 MHz) δ 166.0, 143.5, 139.4, 129.2 (q, $J_{C-F}$=30 Hz), 128.4, 124.5, 124.3 (q, $J_{C-F}$=269 Hz) 102.7, 60.1, 57.5, 13.0; MS (EI) m/z 350 ($M^+$); HRMS (EI) m/z calcd for $C_{13}H_{13}F_3N_2O_4S$ [$M^+$ ] 350.0548, found 350.0546.

4h

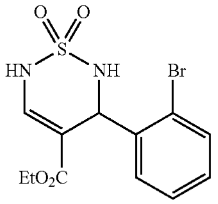

Ethyl 3-(2-bromophenyl)-3,6-dihydro-2H-1,2,6-thiadiazine-4-carboxylate 1,1-dioxide (4h). According to General Procedure A, sulfamide 3 (0.050 g, 0.13 mmol), 2-bromobenzaldehyde (0.031 mL, 0.26 mmol), and TFA (0.193 mL, 2.52 mmol) were stirred at rt for 16 h and provided a crude residue that was purified by chromatography on $SiO_2$ (1:3 to 3:7; EtOAc:hexanes) to give 4h (0.042 g, 45%) as a colorless solid: Mp 172-174° C.; IR (KBr) 1682, 1275, 1150 $cm^{-1}$; $^{1}H$ NMR (DMSO-$d_6$, 600 MHz) δ 10.94 (s, 1H), 8.11 (d, 1H, J=7.2 Hz), 7.62 (d, 1H, J=7.2 Hz), 7.57 (s, 1H), 7.31-7.22 (m, 3H), 5.64 (d, 1H, J=7.2 Hz), 4.01-3.94 (m, 2H), 1.03 (t, 3H, J=6.8 Hz); $^{13}C$ NMR (MeOD-$d_4$, 150 MHz) δ 165.8, 139.4, 137.4, 132.5, 129.9, 129.2, 126.6, 124.1, 103.2, 60.0, 57.6, 13.0; MS (EI) 360/362 ($M^+$); HRMS (EI) m/z calcd for $C_{12}H_{13}N_2O_4SBr$ [$M^+$ ] 360.9858, found 360.9861.

4i

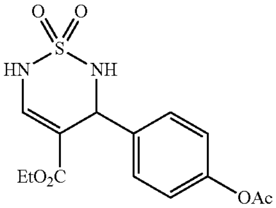

Ethyl 3-(4-acetoxyphenyl)-3,6-dihydro-2H-1,2,6-thiadiazine-4-carboxylate 1,1-dioxide (4i). According to General Procedure A, sulfamide 3 (0.050 g, 0.13 mmol), 4-formylphenyl acetate (0.0370 mL, 0.260 mmol), and TFA (0.190 mL, 2.48 mmol) were stirred at rt for 16 h and provided a crude residue that was purified by chromatography on $SiO_2$ (15:85 to 35:65; EtOAc:hexanes) to give 4i (0.042 g, 48%) as a colorless solid: Mp 126-127° C.; IR (KBr) 1724, 1704, 1276, 1158 $cm^{-1}$; $^{1}H$ NMR (DMSO-$d_6$, 600 MHz) δ 10.86 (s, 1H), 7.98 (d, 1H, J=7.2 Hz), 7.51 (s, 1H), 7.28 (d, 2H, J=8.4 Hz), 7.05 (d, 2H, J=7.8 Hz), 5.35 (d, 1H, J=7.2 Hz), 4.06-3.97 (m, 2H), 2.26 (s, 3H), 1.07 (t, 3H, J=7.2 Hz); $^{13}C$ NMR (DMSO-$d_6$, 150 MHz) δ 169.1, 165.1, 149.6, 138.9, 136.5, 128.9, 122.0, 102.6, 59.6, 56.9, 20.8, 14.0; MS (EI) m/z 340 ($M^+$); HRMS (EI) m/z calcd for $C_{14}H_{16}N_2O_6S$ [$M^+$] 340.0729, found 340.0735.

4j

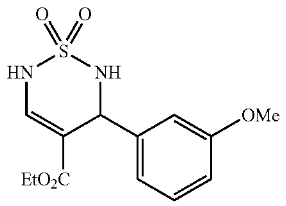

Ethyl 3-(3-methoxyphenyl)-3,6-dihydro-2H-1,2,6-thiadiazine-4-carboxylate 1,1-dioxide (4j). According to General Procedure A, sulfamide 3 (2.00 g, 5.15 mmol), 3-methoxybenzaldehyde (1.38 mL, 11.3 mmol), and TFA (7.65 mL, 99.9 mmol) were stirred at rt for 48 h and provided a crude residue that was purified by chromatography on $SiO_2$ (100% hexanes to 35:65; EtOAc:hexanes) to give 4j (2.00 g, 62%) as a colorless solid: Mp 74-77° C.; IR (KBr) 1701, 1265, 1156 $cm^{-1}$; $^{1}H$ NMR (DMSO-$d_6$, 300 MHz) δ 10.80 (s, 1H), 7.89 (d, 1H, J=7.5 Hz), 7.48 (s, 1H), 7.21 (t, 1H, J=7.8 Hz), 6.85-6.79 (m, 3H), 5.30 (d, 1H, J=7.5 Hz), 4.04-3.95 (m, 2H), 3.73 (s, 3H), 1.06 (t, 3H, J=7.2 Hz); $^{13}C$ NMR (MeOD-$d_4$, 150 MHz) δ 166.1, 157.2, 138.6, 128.9, 128.6, 126.6, 119.5, 110.4, 104.5, 59.8, 54.7, 52.5, 12.9; MS (EI) m/z 312 ($M^+$, 10), 247 ($[M-SO_2]^+$, 60); HRMS (EI) m/z calcd for $C_{13}H_{16}N_2O_5S$ [$M^+$] 312.0780, found 312.0769.

4k

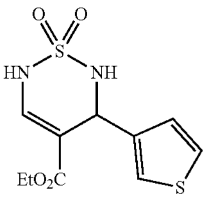

Ethyl 3-(thiophen-3-yl)-3,6-dihydro-2H-1,2,6-thiadiazine-4-carboxylate 1,1-dioxide (4k). According to General Procedure A, sulfamide 3 (0.101 g, 0.260 mmol), thiophene-3-carbaldehyde (0.0455 mL, 0.519 mmol), and TFA (0.385 mL, 5.18 mmol) were stirred at rt for 23 h and provided a crude residue that was purified by chromatography on $SiO_2$ (2:8 to 4:6; EtOAc:hexanes) to give 4k (0.0455 g, 30%) as a colorless solid: Mp 147-148° C. ($CHCl_3$); IR (ATR) 3241, 3129, 1663, 1281, 1150 $cm^{-1}$; $^1H$ NMR (DMSO-$d_6$, 400 MHz) δ 10.78 (bs, 1H), 7.90 (d, 1H, J=7.0 Hz), 7.43-7.38 (m, 2H), 7.21-7.16 (m, 1H), 7.03 (dd, 1H, J=5.0, 1.1 Hz), 5.36 (d, 1H, J=6.9 Hz), 4.03 (dq, 2H, J=10.8, 7.1 Hz), 1.09 (t, 3H, J=7.1 Hz); $^{13}C$ NMR (DMSO-$d_6$, 100 MHz) δ 165.2, 140.2, 138.2, 127.7, 125.1, 123.1, 103.6, 59.6, 53.3, 14.1; HRMS ($ESI^+$) m/z calcd for $C_{10}H_{12}N_2O_4S_2Na$ $[M+Na]^+$ 311.0136, found 311.0116.

5a

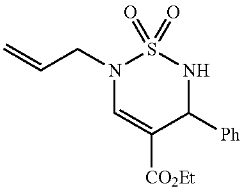

General Procedure B: Preparation of monoalkylated thiadiazines. Ethyl 3-(thiophen-3-yl)-3,6-dihydro-2H-1,2,6-thiadiazine-4-carboxylate 1,1-dioxide (5a). To a solution of thiadiazine 4a (0.130 g, 0.460 mmol) and allyl alcohol (0.0380 mL, 0.550 mmol) in THF (4 mL) was added $PPh_3$ (0.144 g, 0.550 mmol) and DBAD (0.127 g, 0.550 mmol). The reaction mixture was stirred at rt for 1 h, concentrated under reduced pressure, and purified by chromatography on $SiO_2$ (1:6 to 1:2; EtOAc:hexanes) to give 5a (0.144 g, 77%) as a colorless oil: IR (KBr) 1701, 1266, 1180 $cm^{-1}$; $^1H$ NMR ($CDCl_3$, 600 MHz) δ 7.41 (s, 1H), 7.35-7.30 (m, 5H), 5.94-5.88 (m, 1H), 5.56 (d, 1H, J=8.4 Hz), 5.40 (d, 1H, J=16.8 Hz), 5.36 (d, 1H, J=10.2 Hz), 4.74 (d, 1H, J=8.4 Hz), 4.18-4.12 (m, 2H), 4.03-3.99 (m, 1H), 3.98-3.93 (m, 1H), 0.98 (t, 3H, J=7.2 Hz); $^{13}C$ NMR ($CDCl_3$, 150 MHz) δ 164.5, 140.5, 137.6, 131.1, 127.9, 126.9, 119.8, 106.7, 59.8, 59.0, 50.8, 27.5, 13.3; MS (EI) m/z 323 ($M^+$); HRMS ($ESI^+$) m/z calcd for $C_{15}H_{19}N_2O_4S$ [$M^+$ ] 323.1066, found 323.1062.

5b

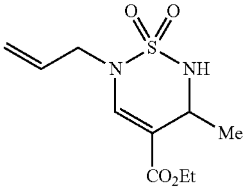

Ethyl 6-allyl-3-methyl-3,6-dihydro-2H-1,2,6-thiadiazine-4-carboxylate 1,1-dioxide (5b). According to General Procedure B, 4b (0.120 g, 0.545 mmol), allyl alcohol (0.0440 mL, 0.645 mmol), $PPh_3$ (0.171 g, 0.652 mmol), and DBAD (0.150 g, 0.651 mmol) in THF (4 mL) were stirred at rt for 30 min and provided a crude residue that was purified by chromatography on $SiO_2$ (1:2; EtOAc:hexanes) to give 5b (0.102 g, 72%) as a colorless oil: IR (KBr) 1700, 1265, 1179 $cm^{-1}$; $^1H$ NMR ($CDCl_3$, 600 MHz) δ 7.18 (s, 1H), 5.91-5.85 (m, 1H), 5.38-5.33 (m, 2H), 4.68 (d, 2H, J=7.8 Hz), 4.50 (quint., 1H, J=7.2 Hz), 4.23-4.17 (m, 2H), 4.13 (dd, 2H, J=11.2, 6.0 Hz), 1.59 (d, 3H, J=7.2 Hz), 1.29 (t, 3H, J=7.2 Hz); $^{13}C$ NMR ($CDCl_3$, 150 MHz) δ 165.3, 139.3, 131.8, 120.2, 108.6, 60.5, 52.2, 51.3, 19.4, 14.3; MS ($ESI^+$) m/z 260 ($M^+$); HRMS ($ESI^+$) m/z calcd for $C_{10}H_{16}N_2O_4S$ ($M^+$) 260.0831, found 260.0837.

5c

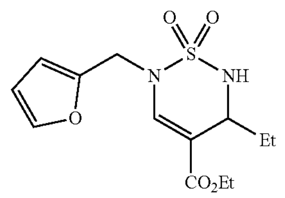

Ethyl 3-ethyl-6-(furan-2-ylmethyl)-3,6-dihydro-2H-1,2,6-thiadiazine-4-carboxylate 1,1-dioxide (5c). According to General Procedure B, 4c (0.211 g, 0.900 mmol), 2-furylmethan-1-ol (0.0650 mL, 0.747 mmol), $PPh_3$ (0.236 g, 0.900 mmol), and DEAD (0.142 mL, 0.900 mmol) in THF (6 mL) were stirred at 0° C. for 10 min and provided a crude residue that was purified by chromatography on $SiO_2$ (1:10 to 1:4; EtOAc:hexanes) to give 5c (0.088 g, 37%) as a colorless oil: IR (ATR) 3263, 1690, 1625, 1353, 1236, 1176 $cm^{-1}$, $^1H$ NMR ($CDCl_3$, 300 MHz) δ 7.42 (d, 1H, J=1.8 Hz), 7.26 (s, 1H), 6.41 (d, 1H, J=2.1 Hz), 6.37-6.35 (m, 1H), 4.67, 4.62 (d, 2H, J=15.8 Hz), 4.46 (d, 1H, J=7.2 Hz), 4.25-4.12 (m, 3H), 2.06-1.83 (m, 2H), 1.27 (t, 3H, J=7.2 Hz), 1.02 (t, 3H, J=7.2 Hz). $^{13}C$ NMR ($CDCl_3$, 75 MHz) δ 165.3, 148.3, 143.5, 139.3, 110.8, 110.3, 108.4, 60.5, 58.3, 44.9, 25.2, 14.3, 10.4; HRMS (EI) calcd for $C_{13}H_{18}N_2O_5S$ ($M^+$) 314.0936, found 314.0937.

5d

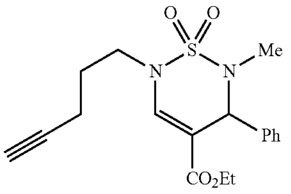

Ethyl 6-(pent-4-yn-1-yl)-3-phenyl-3,6-dihydro-2H-1,2,6-thiadiazine-4-carboxylate 1,1-dioxide (5d). According to General Procedure B, 4a (1.45 g, 5.12 mmol), 4-pentyn-1-ol (0.572 mL, 6.15 mmol), $PPh_3$ (1.46 g, 5.52 mmol), and DBAD (1.30 g, 5.55 mmol) in THF (30 mL) were stirred at rt for 5 h and provided a crude residue that was purified by chromatography on $SiO_2$ (1:9 to 1:1; EtOAc:hexanes) to give 5d (1.033 g, 58%) as a colorless oil: IR (ATR) 3439, 3282, 1685, 1618, 1165, 1034 $cm^{-1}$; $^1H$ NMR ($CDCl_3$, 500 MHz) δ 7.50 (d, 1H, J=0.9 Hz), 7.38-7.30 (m, 5H), 5.55 (d, 1H, J=8.5 Hz), 4.55 (d, 1H, J=8.5 Hz), 4.03, 3.96 (dq, 2H, J=10.9, 7.2 Hz), 3.73 (dt, 2H, J=14.5, 7.1 Hz), 2.34 (td, 2H, J=6.8, 2.7 Hz), 2.06 (t, 1H, J=2.7 Hz), 1.97 (quint., 2H, J=6.9 Hz), 1.00 (t, 3H, J=7.2 Hz); $^{13}C$ NMR ($CDCl_3$, 125 MHz) δ 165.2, 142.3, 138.3, 128.9, 128.7, 127.6, 106.7, 82.6, 70.2, 60.5, 59.8, 49.2, 28.1, 15.6, 14.0; HRMS ($ESI^+$) m/z calcd for $C_{14}H_{19}N_2O_4S$ $[M+H]^+$311.1066, found 311.1069.

5e

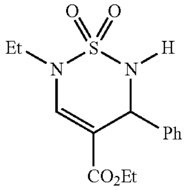

Ethyl 6-ethyl-3-phenyl-3,6-dihydro-2H-1,2,6-thiadiazine-4-carboxylate 1,1-dioxide (5e). According to General Procedure B, 4a (0.871 g, 3.09 mmol), ethanol (0.213 mL, 3.70 mmol), $PPh_3$ (0.984 g, 3.72 mmol), and DBAD (0.853 g, 3.63 mmol) in THF (20 mL) were stirred at rt for 4.5 h and provided a crude residue that was purified by chromatography on $SiO_2$ (15:85 to 3:7; EtOAc:hexanes) to give 5e (0.723 g, 75%) as a colorless solid: Mp 99-101° C. ($CH_2Cl_2$); IR (ATR) 3197, 1661, 1609, 1171 $cm^{-1}$; $^1H$ NMR (acetone-$d_6$, 400 MHz) δ 7.63 (s, 1H), 7.39-7.35 (m, 2H), 7.34-7.23 (m, 3H), 6.95 (d, 1H, J=7.6 Hz), 5.55 (d, 1H, J=7.7 Hz), 4.03, 3.97 (dq, 2H, J=10.8, 7.1 Hz), 3.73, 3.68 (dq, 2H, J=14.5, 7.2 Hz), 1.32 (t, 3H, J=7.2 Hz), 1.03 (t, 3H, J=7.1 Hz); $^{13}C$ NMR (acetone-$d_6$, 100 MHz) δ 165.8, 142.6, 139.9, 129.0, 128.8, 128.4, 106.3, 60.4, 59.5, 45.6, 15.6, 14.4; HRMS ($ESI^+$) m/z calcd for $C_{14}H_{19}N_2O_4S$ $[M+H]^+$ 311.1066, found 311.1069.

5g

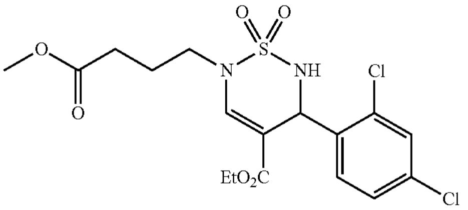

Ethyl 3-(2,4-dichlorophenyl)-6-(4-methoxy-4-oxobutyl)-3,6-dihydro-2H-1,2,6-thiadiazine-4-carboxylate 1,1-dioxide (5g). To a solution of 4d (3.15 g, 8.96 mmol) in THF (55 mL) was added methyl 4-hydroxybutanoate (1.00 mL, 8.96 mmol). $PPh_3$ (2.37 g, 8.96 mmol) and DBAD (2.08 g, 8.96 mmol) were sequentially added at 0° C. The reaction mixture was warmed to rt, stirred for 15 h, and quenched with $H_2O$ (50 mL). The aqueous layer was extracted with $CH_2Cl_2$ (3×50 mL). The combined organic layers were washed with brine (150 mL), concentrated, and purified by column chromatography on $SiO_2$ (2:3, EtOAc:hexanes, followed by 3:7, acetone:hexanes) to afford 5g (4.04 g, 53%) as a sticky clear foam: IR (ATR) 3197, 3064, 2953, 1725, 1664, 1626, 1589, 759 $cm^{-1}$; $^1H$ NMR (500 MHz, $CDCl_3$) δ 7.51 (bs, 1H), 7.43 (d, 1H, J=2 Hz), 7.28 (d, 1H), 7.2 (dd, 1H, J=2, 9 Hz), 5.9 (d, 1H, J=8 Hz), 4.91 (d, 1H, J=8 Hz), 4.07 (dq, 2H, J=4.0, 7.2 Hz), 3.70 (app bs, 3H), 3.68 (dt, 2H, J=3, 6.8 Hz), 2.46 (t, 2H, J=7 Hz), 2.09 (dquint, 2H, J=6.8, 7.0 Hz), 1.09 (t, 3H, J=7.2 Hz); $^{13}C$ NMR (125 MHz, $CDCl_3$) δ 173.3, 164.9, 142.4, 134.9, 134.6, 133.8, 130.6, 129.7, 127.0, 104.6, 60.1, 55.6, 52.0, 49.5, 30.7, 24.8, 14.1; HRMS ($ESI^+$) calcd for $C_{17}H_{21}O_6N_2Cl_2S$ $[M+H]^+$ 451.0419, found 451.0493. LCMS-ELSD purity 100%.

5h

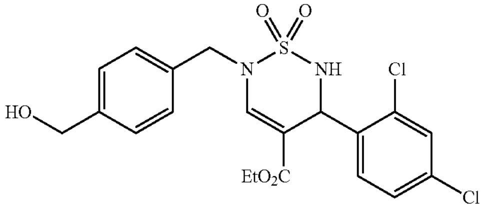

Ethyl 3-(2,4-dichlorophenyl)-6-(4-(hydroxymethyl)benzyl)-3,6-dihydro-2H-1,2,6-thiadiazine-4-carboxylate 1,1-dioxide (5h). In a 500-mL 3-neck flask equipped with a $N_2$ inlet, septum, and a $N_2$-sparge needle, thiadiazine 4d (1.02 g, 2.90 mmol), THF (16.0 mL), and 1,4-benzenedimethanol (0.398 g, 2.88 mmol) were added. The reaction mixture was sparged with $N_2$ and cooled to 0° C. After 5 min, $PPh_3$ (0.748 g, 2.85 mmol) was added, followed by a portionwise addition of DBAD (0.671 g, 2.91 mmol). After 30 min, the reaction was warmed to rt, and the $N_2$-sparge line was removed. The reaction mixture was stirred for 20 h and was treated with water (40 mL), transferred to a separatory funnel, and extracted with EtOAc (3×40 mL). The combined organic layers were washed with brine (40 mL), dried ($Na_2SO_4$), filtered, and concentrated. Purification by chromatography on $SiO_2$ (100% hexanes to 1:1; EtOAc:hexanes) afforded a mixture of the alkylated product and 1,4-benzenedimethanol. The mixture was dissolved in acetone (4 mL) and triturated with hexanes (20 mL), and the white precipitate was filtered under vacuum to afford 5h (0.714 g, 52%) as a white solid: Mp 75-77° C.; IR (ATR, $CH_2Cl_2$) 3467, 3074, 1686, 1625, 1270, 1174 $cm^{-1}$; $^1H$ NMR (500 MHz; DMSO-$d_6$) δ 8.70 (d, 1H, J=7.2 Hz) 7.73 (s, 1H), 7.64 (d, 1H, J=2.15 Hz), 7.38 (dd, 1H, J=8.4, 2.1 Hz) 7.36-7.33 (m, 4H), 7.21 (d, 1H, J=8.4 Hz), 5.62 (d, 1H, J=7.2 Hz), 5.20 (t, 1H, J=5.7 Hz), 4.86 (d, 1H, J=15.7 Hz), 4.78 (d, 1H, J=15.7 Hz), 4.50 (d, 1H, J=5.7 Hz), 4.02-3.91 (m, 2H), 1.01 (t, 3H, J=7.05 Hz); $^{13}C$ NMR (126 MHz; DMSO-$d_6$) δ 164.4, 142.9, 134.7, 134.6, 133.9, 133.2, 131.3, 128.8, 127.7, 126.75, 126.71, 102.5, 62.6, 59.9, 53.9, 51.4, 14.0; HRMS ($ESI^+$) m/z calcd for $C_{20}H_{21}O_5N_2Cl_2S$ $[M+H]^+$ 471.0543, found 471.0547; LCMS-220 nm purity 100%.

5i

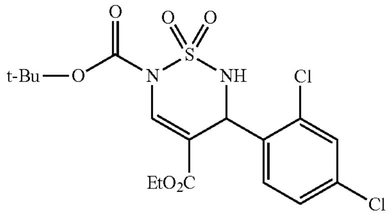

2-(tert-Butyl) 4-ethyl 5-(2,4-dichlorophenyl)-5,6-dihydro-2H-1,2,6-thiadiazine-2,4-dicarboxylate 1,1-dioxide (5i). A solution of compound 4d (5.06 g, 14.4 mmol) in acetonitrile (120 mL) was treated with $K_2CO_3$ (4.45 g, 13.2 mmol). After stirring at rt for 25 min, $Boc_2O$ (2.8 g, 13.0 mmol) was added and the reaction mixture was stirred for 7 h. The mixture was treated with water (300 mL), transferred to a separatory funnel, and extracted with EtOAc (3×300 mL). The combined organic layers were washed with brine (200 mL), dried ($Na_2SO_4$), filtered, and concentrated. The residue was purified by chromatography on $SiO_2$ (100% hexanes to 1:1; EtOAc:hexanes) to afford 5i (5.08 g, 86%) as a white solid: Mp 56-58° C. (dec); IR (ATR, $CH_2Cl_2$) 3246, 2985, 1745, 1709, 1372, 1254, 1141 $cm^{-1}$; $^1H$ NMR (500 MHz; DMSO-$d_6$) δ 9.36 (d, 1H, J=5.5 Hz), 8.07 (d, 1H, J=0.6 Hz), 7.69 (d, 1H, J=2.2 Hz), 7.38 (dd, 1H, J=8.4, 2.2 Hz), 7.27 (d, 1H, J=8.4 Hz), 5.59 (d, 1H, J=5.2 Hz), 4.12-4.01 (m, 2H), 1.52 (m, 9H), 1.09 (t, 3H, J=7.1 Hz); $^{13}C$ NMR (500 MHz; DMSO-$d_6$) δ 163.7, 147.5, 135.9, 133.9, 133.7, 133.3, 131.4, 128.9, 127.0, 108.2, 86.1, 60.7, 53.1, 27.4, 13.8; HRMS (ESI$^+$) m/z calcd for $C_{17}H_{19}O_6N_2Cl_2$ S $[M-H]^-$ 449.0335, found 449.0333.

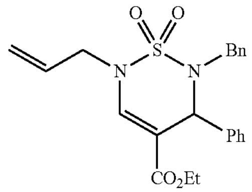

6a

Ethyl 6-allyl-2-benzyl-3-phenyl-3,6-dihydro-2H-1,2,6-thiadiazine-4-carboxylate 1,1-dioxide (6a). To a suspension of NaH (0.022 g, 0.92 mmol) in THF (4.0 mL) cooled to 0° C. was added thiadiazine 5a (0.071 g, 0.22 mmol). The reaction mixture was stirred for 30 min at 0° C., treated with benzyl bromide (0.0560 g, 0.330 mmol), warmed to rt, stirred for 30 min, and treated with TBAI (0.0053 g, 0.022 mmol). The reaction mixture was stirred for an additional 10 min, quenched with sat. aq. $NH_4Cl$ (3 mL), and diluted with EtOAc (5 mL). The organic layer was separated and the aqueous layer was extracted with EtOAc (3×7 mL). The combined organic layers were washed with brine, dried ($MgSO_4$), filtered, and concentrated under reduced pressure. The crude residue was purified by chromatography on $SiO_2$ (1:9 to 4:6; EtOAc:hexanes) to give 6a (0.061 g, 68%) as a colorless oil: IR (KBr) 1701, 1263, 1180 $cm^{-1}$; $^1H$ NMR ($CDCl_3$, 600 MHz) δ 7.55 (s, 1H), 7.50-7.44 (m, 1H), 7.43-7.41 (m, 1H), 7.23-7.20 (m, 3H), 7.04-7.02 (m, 2H), 5.96-5.91 (m, 1H), 5.45-5.37 (m, 3H), 4.83 (d, 1H, J=13.2 Hz), 4.26-4.12 (m, 4H), 3.73 (d, 1H, J=13 Hz), 1.14 (t, 3H, J=7.0 Hz); $^{13}C$ NMR ($CDCl_3$, 150 MHz) δ 165.9, 140.6, 138.0, 134.6, 132.0, 129.7, 129.0, 128.7, 127.8, 127.6, 127.5, 120.4, 102.4, 61.8, 60.6, 55.4, 51.9, 14.2; MS (ESI$^+$) m/z 435 $[M+Na]^+$; HRMS (ESI$^+$) m/z calcd for $C_{22}H_{24}N_2O_4NaS$ $[M+Na]^+$ 435.1354, found 435.1352.

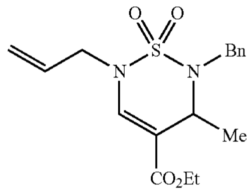

6b

Ethyl 6-allyl-2-benzyl-3-methyl-3,6-dihydro-2H-1,2,6-thiadiazine-4-carboxylate 1,1-dioxide (6b). To a suspension of NaH (0.023 g, 0.96 mmol) in THF (4.0 mL) cooled to 0° C. was added thiadiazine 5b (0.061 g, 0.24 mmol). The reaction mixture was stirred for 30 min at 0° C., treated with benzyl bromide (0.060 g, 0.35 mmol), warmed to rt, stirred for 30 min, and treated with $NH_4I$ (0.0035 g, 0.024 mmol). The reaction mixture was stirred for an additional 10 min, quenched with sat. aq. $NH_4Cl$ (3 mL), and diluted with EtOAc (5 mL). The organic layer was separated and the aqueous layer was extracted with EtOAc (3×7 mL). The combined organic layers were washed with brine, dried ($MgSO_4$), filtered, and concentrated under reduced pressure. The crude residue was purified by chromatography on $SiO_2$ (1:9 to 4:6; EtOAc:hexanes) to give 6b (0.058 g, 71%) as a colorless oil: IR (KBr) 1698, 1265, 1180 $cm^{-1}$; $^1H$ NMR ($CDCl_3$, 600 MHz) δ 7.39-7.32 (m, 5H), 7.20 (s, 1H), 5.92-5.88 (m, 1H), 5.41 (d, 1H, J=17.4 Hz), 5.36 (d, 1H, J=10.2 Hz), 4.70 (d, 1H, J=14.4H), 4.25 (q, 1H, J=7.2 Hz), 4.22-4.13 (m, 4H), 3.69 (d, 1H, J=14.4 Hz), 1.53 (d, 3H, J=7.2 Hz), 1.26 (t, 3H, J=7.2 Hz); $^{13}C$ NMR ($CDCl_3$, 150 MHz) δ 165.6, 138.6, 134.9, 132.1, 128.8, 128.5, 128.2, 120.2, 106.3, 60.5, 56.9, 55.3, 51.6, 20.2, 14.3; MS (ESI$^+$) m/z 350 ($M^+$); HRMS (EI$^+$) calcd for $C_{17}H_{22}N_2O_4S$ [$M^+$ ] 350.1300, found 350.1308.

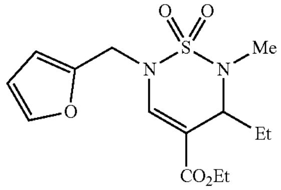

6c

Ethyl 3-ethyl-6-(furan-2-ylmethyl)-2-methyl-3,6-dihydro-2H-1,2,6-thiadiazine-4-carboxylate 1,1-dioxide (6c). To a suspension of thiadiazine 5c (0.029 g, 0.090 mmol) and $K_2CO_3$ (0.037 g, 0.27 mmol) in $CH_3CN$ (2 ml) was added iodomethane (0.015 ml, 0.23 mmol). The reaction mixture was stirred at rt for 16 h and diluted with EtOAc and water. The aqueous layer was extracted with EtOAc. The combined organic layers were washed with brine, dried ($Na_2SO_4$), filtered, and concentrated under reduced pressure to give 6c (0.027 g 91%) as a colorless oil: IR (ATR) 2976, 1694, 1623, 1366, 1165 $cm^{-1}$; $^1H$ NMR ($CDCl_3$, 300 MHz) δ 7.42 (dd, 1H, J=1.8, 0.6 Hz), 7.29 (s, 1H), 6.42 (dd, 1H, J=3.0, 0.6 Hz), 6.37 (dd, 1H, J=3.3, 1.8 Hz), 4.74 (d, 2H, J=15.9 Hz), 4.59 (d, 2H, J=15.9 Hz), 4.19 (q, 2H, J=6.9 Hz), 3.95 (dd, 1H, 11.4, 4.2 Hz), 2.71 (s, 3H), 2.17-2.06 (m, 1H), 1.90-1.81 (m, 1H), 1.29 (t, 3H, J=7.2 Hz), 1.04 (t, 3H, J=7.2 Hz); $^{13}C$ NMR ($CDCl_3$, 75 MHz) δ 165.8, 148.7, 143.3, 138.1, 110.7, 110.0, 105.6, 67.1, 60.4, 45.3, 40.4, 25.9, 14.2, 10.6; HRMS (EI) m/z calcd for $C_{14}H_{20}N_2O_5S$ [$M^+$] 328.1093, found 328.1090.

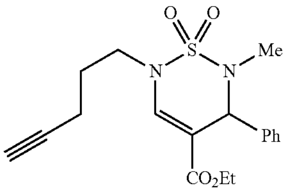

6d

Ethyl 2-methyl-6-(pent-4-yn-1-yl)-3-phenyl-3,6-dihydro-2H-1,2,6-thiadiazine carboxylate 1,1-dioxide (6d). To a suspension of thiadiazine 5d (1.01 g, 2.90 mmol) and $K_2CO_3$ (1.21 g, 8.74 mmol) in MeCN (14 mL) was added iodomethane (0.450 mL, 7.23 mmol) over 5 min. The solution was stirred at rt for 3.5 h. The reaction mixture was diluted with water (25 mL) and EtOAc (25 mL). The organic layer was separated, and the aqueous layer was extracted with EtOAc (3×10 mL). The combined organic layers were washed with sat. aq. $Na_2SO_3$ (1×20 mL), sat. aq. $NaHCO_3$ (1×20 mL), and brine (1×20 mL), dried ($Na_2SO_4$), filtered, and concentrated under reduced pressure. The crude oil was purified by chromatography on $SiO_2$ (1:9 to 2:8; EtOAc:hexanes) to give 6d (1.03 g, 98%) as a colorless oil: IR (ATR) 3286, 1692, 1622, 1366, 1161 $cm^{-1}$; $^1H$ NMR ($CDCl_3$, 500 MHz) δ 7.57 (s, 1H), 7.33-7.26 (m, 5H), 5.46 (s, 1H), 4.16, 4.10 (dq, 2H, J=10.9, 7.2 Hz), 3.77, 3.70 (dt, 2H, =14.7, 6.3 Hz), 2.32 (dt, 2H, J=6.7, 2.6 Hz), 2.07 (t, 1H, J=2.4 Hz), 2.01-1.88 (m, 2H), 1.15 (t, 3H, J=7.2 Hz); $^{13}C$ NMR ($CDCl_3$, 125 MHz) δ 166.0, 141.3, 138.0, 128.1, 128.0, 127.8, 102.2, 82.4, 70.2, 66.4, 60.7, 49.5, 39.6, 28.5, 15.5, 14.3; HRMS ($ESI^+$) m/z calcd for $C_{18}H_{23}N_2O_4S$ $[M+H]^+$ 363.1379, found 363.1400.

6e

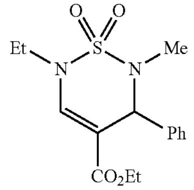

Ethyl 6-ethyl-2-methyl-3-phenyl-3,6-dihydro-2H-1,2,6-thiadiazine-4-carboxylate 1,1-dioxide (6e). To a suspension of thiadiazine 5e (0.741 g, 2.39 mmol) and $K_2CO_3$ (1.01 g, 7.27 mmol) in MeCN (24 mL) was added iodomethane (0.372 mL, 5.98 mmol). The reaction mixture was stirred at rt for 2.5 h, then diluted with water (20 mL) and EtOAc (10 mL). The organic layer was separated and the aqueous layer was extracted with EtOAc (2×10 mL). The combined organic layers were washed with sat. aq. $Na_2SO_3$ (1×15 mL) and brine (1×15 mL), dried ($Na_2SO_4$), decanted, and concentrated under reduced pressure to give a yellow crude oil. The crude oil was purified by chromatography on $SiO_2$ (15:85 to 2:8; EtOAc:hexanes) to give the dialkylated thiadiazine 6e (0.782 g, 100%) as a light yellow viscous oil: IR (ATR) 2977, 1692, 1141, 1038 $cm^{-1}$; $^1H$ NMR (acetone-$d_6$, 400 MHz) δ 7.70 (s, 1H), 7.34-7.17 (m, 5H), 5.52 (s, 1H), 4.10, 4.06 (dq, 2H, J=10.8, 7.1 Hz), 3.73 (q, 2H, J=7.2 Hz), 2.95 (s, 3H), 1.32 (t, 3H, J=7.2 Hz), 1.12 (t, 3H, J=7.1 Hz); $^{13}C$ NMR (acetone-$d_6$, 100 MHz) δ 166.3, 141.6, 140.0, 128.8, 128.4, 128.1, 102.7, 67.0, 60.7, 46.0, 40.1, 15.8, 14.5; HRMS ($ESI^+$) m/z calcd for $C_{15}H_{21}N_2O_4S$ $[M+H]^+$ 325.1222, found.

6f

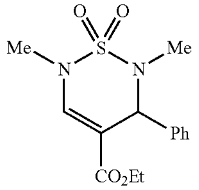

Ethyl 2,6-dimethyl-3-phenyl-3,6-dihydro-2H-1,2,6-thiadiazine-4-carboxylate 1,1-dioxide (6f). To a suspension of thiadiazine 4a (2.39 g, 8.47 mmol) and $K_2CO_3$ (7.00 g, 50.7 mmol) in MeCN (40 mL) was added iodomethane (2.65 mL, 42.6 mmol). The reaction mixture was stirred at rt for 2.25 h, then diluted with water (50 mL) and EtOAc (50 mL). The organic layer was separated and the aqueous layer was extracted with EtOAc (3×15 mL). The combined organic layers were washed with sat. aq. $Na_2SO_3$ (1×25 mL), sat. aq. $NaHCO_3$ (1×25 mL), and brine (1×25 mL), dried ($Na_2SO_4$), filtered, and concentrated under reduced pressure to give a light yellow sticky oil. The crude oil was purified by chromatography on $SiO_2$ (1:9 to 2:8; EtOAc:hexanes) to give 16 (2.620 g, 100%) as a light yellow oil: IR (ATR) 2977, 2932, 1691, 1366 $cm^{-1}$; $^1H$ NMR ($CDCl_3$, 400 MHz) δ 7.45 (s, 1H), 7.34-7.25 (m, 5H), 5.46 (s, 1H), 4.15, 4.11 (dq, 2H, J=10.9, 7.1 Hz), 3.28 (s, 3H), 2.93 (s, 3H), 1.15 (t, 3H, J=7.1 Hz); $^{13}C$ NMR ($CDCl_3$, 100 MHz) δ 166.0, 142.1, 138.0, 128.1, 128.0, 127.8, 102.4, 66.4, 60.7, 39.8, 36.8, 14.3; HRMS ($ESI^+$) m/z calcd for $C_{14}H_{19}N_2O_4S$ $[M+H]^+$ 311.1066, found 311.1103.

6i

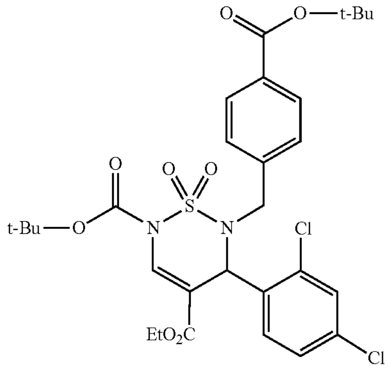

2-(tert-Butyl) 4-ethyl 6-(4-(tert-butoxycarbonyl)benzyl)-5-(2,4-dichlorophenyl)-5,6-dihydro-2H-1,2,6-thiadiazine-2,4-dicarboxylate 1,1-dioxide (6i). To a suspension of 5i (4.43 g, 9.81 mmol) and $K_2CO_3$ (7.49 g, 54.2 mmol) in MeCN (125 mL) was added the bromide (2.80 g, 10.3 mmol). The reaction mixture was stirred at rt for 2 h, diluted with water (150 mL)/brine (150 mL) and EtOAc (200 mL). The layers were transferred to a separatory funnel and separated. The aqueous layer was extracted with EtOAc (2×300 mL). The combined organic layers were dried ($Na_2SO_4$), filtered, and concentrated. Purification by chromatography on $SiO_2$ (100% hexanes to 1:5; EtOAc:hexanes) afforded 6i (5.00 g, 79%) as a white solid: Mp 99-102° C.; IR (ATR, $CH_2Cl_2$) 2981, 1746, 1709, 1396, 1242, 1142 $cm^{-1}$; $^1H$ NMR (300 MHz; $CDCl_3$) δ 7.933 (d, 2H, J=8.2 Hz), 7.927 (s, 1H), 7.45 (d, 2H, J=8.2 Hz), 7.37 (s, 1H), 7.16-7.14 (m, 2H), 5.77 (s, 1H), 4.75 (d, 1H, J=14.8 Hz), 4.61 (d, 1H, J=14.8H), 4.20-4.01 (m, 2H), 1.60 (s, 9H), 1.59 (s, 9H), 1.16 (t, 3H, J=7.1 Hz); $^{13}C$ NMR (75 MHz; $CDCl_3$) δ 165.3, 164.2, 148.0, 138.1, 136.1, 135.3, 134.9, 133.0, 132.5, 131.4, 129.7, 129.6, 129.64, 139.61, 126.8, 107.3, 87.1, 81.5, 61.3, 60.2, 57.4, 28.3, 28.0, 28.3, 28.0, 14.3; HRMS ($ESI^+$) m/z calcd for $C_{29}H_{35}O_8N_2Cl_2S$ $[M+H]^+$ 641.1486, found 641.1513; LCMS-220 nm purity 100%.

7e

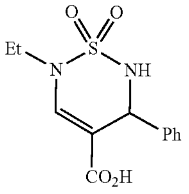

6-Ethyl-3-phenyl-3,6-dihydro-2H-1,2,6-thiadiazine-4-carboxylic acid 1,1-dioxide (7e). To a suspension of ester 5e (0.250 g, 0.805 mmol) in EtOH (1.0 mL) was added in one portion 2 M KOH (4.0 mL, 8.0 mmol). The reaction mixture was stirred at 80° C. for 4 h then cooled to rt, diluted with EtOAc (5 mL), and acidified with 5 M HCl (~2 mL). The aqueous layer was extracted with EtOAc (3×5 mL). The combined organic layers were dried ($Na_2SO_4$), decanted, and concentrated under reduced pressure to give acid 7e (0.222 g, 98%) as a yellow-orange solid: Mp 170-175° C. (dec, $CH_2Cl_2$); IR (ATR) 3245, 2922, 1661, 1152 $cm^{-1}$; $^1H$ NMR (acetone-$d_6$, 400 MHz) δ 10.53 (bs, 1H), 7.66 (s, 1H), 7.40-7.37 (m, 2H), 7.32-7.22 (m, 3H), 7.01 (d, 1H, J=7.5 Hz), 5.56 (d, 1H, J=7.5 Hz), 3.74, 3.69 (dq, 2H, J=14.4, 7.1 Hz), 1.33 (t, 3H, J=7.2 Hz); $^{13}C$ NMR (acetone-$d_6$, 100 MHz) δ 167.0, 143.1, 139.9, 129.0, 128.7, 128.3, 105.6, 59.2, 45.6, 15.6; HRMS ($ESI^-$) m/z calcd for $C_{12}H_{13}N_2O_4S$ $[M-H]^-$ 281.0596, found 281.0609.

7g

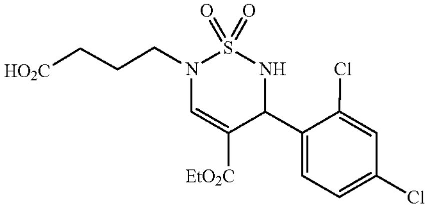

4-(5-(2,4-Dichlorophenyl)-4-(ethoxycarbonyl)-1,1-dioxido-5,6-dihydro-2H-1,2,6-thiadiazin-2-yl)butanoic acid (7g). A solution of 5g (0.851 g, 1.89 mmol) in THF/MeOH (4 mL/4 mL) was treated with a solution of LiOH monohydrate (0.791 g, 18.9 mmol) in water (4 mL). After stirring at rt for 1 h, the reaction mixture was concentrated at 22° C. The residue was acidified with 0.5 M HCl (15 mL) and extracted with EtOAc (3×100 mL). The combined organic layers were washed with 1:1 brine/water (50 mL), dried ($Na_2SO_4$), filtered, and concentrated, yielding 7g (0.865 g, quant.) as an off-white solid that still contained a small amount of residual solvent and was used for the next step without further purification: Mp 56-58° C. (dec, EtOAc); IR (ATR, $CH_2Cl_2$) 3218, 2984, 1705, 1626, 1353, 1172 $cm^{-1}$; $^1H$ NMR (400 MHz; DMSO-$d_6$) δ 12.16 (bs, 1H), 8.60 (s, 1H), 7.74 (s, 1H), 7.64 (d, 1H, J=2.1 Hz), 7.38 (dd, 1H, J=8.4, 2.1 Hz), 7.23 (d, 1H, J=8.4 Hz), 5.59 (s, 1H), 4.06-3.93 (m, 2H), 3.65 (t, 2H, J=7.3 Hz), 1.89-1.82 (m, 2H), 1.05 (t, 3H, J=7.1 Hz); $^{13}C$ NMR (500 MHz; DMSO-$d_6$) δ 173.8, 164.5, 143.3, 134.8, 133.9, 133.2, 131.3, 128.7, 126.7, 102.2, 59.8, 53.8, 48.6, 30.2, 24.9, 14.0; HRMS ($ESI^-$) m/z calcd for $C_{16}H_{17}O_6N_2Cl_2S$ $[M-H]^-$ 435.0179, found 435.0174.

7h

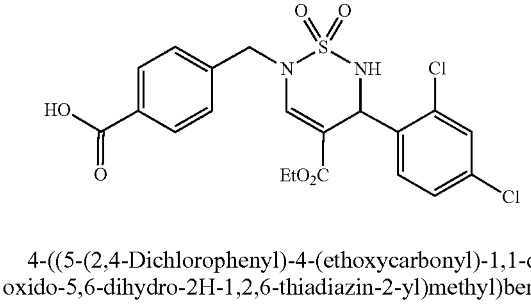

4-((5-(2,4-Dichlorophenyl)-4-(ethoxycarbonyl)-1,1-dioxido-5,6-dihydro-2H-1,2,6-thiadiazin-2-yl)methyl)benzoic acid (7h). A 0° C. solution of 5h (2.39 g, 5.07 mmol) in acetone (18 mL) was treated with dropwise addition of the Jones Reagent (2.5 M, 5.00 mL, 12.5 mmol). The reaction mixture was stirred at 0° C. for 1.5 h. The dark/brown solution was quenched with a small amount of iPrOH (6 mL) and the reaction mixture was stirred for 5 min. The blue mixture was treated with water (60 mL) and extracted with $Et_2O$ (3×100 mL). The combined organic layers were washed with water (100 mL), brine (100 mL), dried ($Na_2SO_4$), filtered, and concentrated to yield 11f (2.32 g, 94%) as a white solid: Mp 101-104° C.; IR (ATR, $CH_2Cl_2$) 3183, 2983, 1687, 1614, 1270, 1175 $cm^{-1}$; $^1H$ NMR (300 MHz; DMSO-$d_6$) δ 12.99 (s, 1H), 8.76 (d, 1H, J=7.2 Hz), 7.97 (d, 2H, J=8.3 Hz), 7.81 (s, 1H), 7.65 (d, 1H, J=2.2 Hz), 7.51 (d, 2H, J=8.3 Hz), 7.40 (dd, 1H, J=8.4, 2.2 Hz), 7.25 (d, 1H, J=8.4 Hz), 5.64 (d, 1H, J=7.1 Hz), 4.99 (d, 1H, J=16.4 Hz), 4.91 (d, 1H, J=16.5 Hz), 4.06-3.90 (m, 2H), 1.02 (t, 3H, J=7.1 Hz); $^{13}C$ NMR (75 MHz; DMSO-$d_6$) δ 167.1, 164.3, 143.2, 141.5, 134.6, 133.9, 133.3, 131.3, 130.3, 129.6, 128.8, 127.8, 126.8, 102.8, 60.0, 53.9, 51.4, 14.0; HRMS ($ESI^+$) m/z calcd for $C_{20}H_{19}O_6N_2Cl_2S$ $[M+H]^+$ 485.0335, found 485.0360; LCMS-220 nm purity 100%.

8e

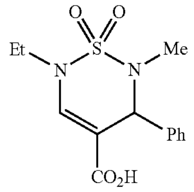

6-Ethyl-2-methyl-3-phenyl-3,6-dihydro-2H-1,2,6-thiadiazine-4-carboxylic acid 1,1-dioxide (8e). To a solution of dialkylated thiadiazine 6e (2.69 g, 8.29 mmol) in EtOH (10 mL) was added in one portion 2 M KOH (43 mL, 85 mmol). The reaction mixture was warmed to 90° C. and stirred for 5 h, cooled to rt, diluted with EtOAc (50 mL), cooled to 0° C., and acidified with 5 M HCl (~17 mL). The aqueous layer was extracted with EtOAc (3×20 mL). The combined organic layers were washed with water (1×10 mL) and brine (1×10 mL), dried ($Na_2SO_4$), decanted, and concentrated under reduced pressure. The crude product contained AcOH that was removed by evaporating with hexanes and $CHCl_3$ to give the acid 8e (2.06 g, 84%) as a light yellow powder: Mp 157-159° C. (dec, $CH_2Cl_2$); IR (ATR) 2969, 2563, 1668, 1655, 1169, 1154 $cm^{-1}$; $^1H$ NMR ($CDCl_3$, 500 MHz) δ 10.96 (bs, 1H), 7.63 (s, 1H), 7.37-7.26 (m, 5H), 5.41 (s, 1H), 3.62 (q, 2H, J=7.2 Hz), 2.91 (s, 3H), 1.33 (t, 3H, J=7.2 Hz); $^{13}C$ NMR ($CDCl_3$, 100 MHz) δ 171.9, 142.9, 137.8, 128.1, 128.0, 127.7, 100.1, 66.1, 45.9, 40.1, 15.5; MS ($ESI^-$) m/z 295 ($[M-1]^-$, 100), 231 (—$SO_2$, 85); HRMS ($ESI^-$) m/z calcd for $C_{13}H_{15}N_2O_4S$ $[M-H]^-$ 295.0753, found 295.0795.

8f

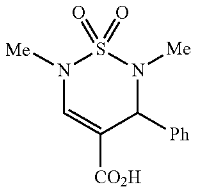

2,6-Dimethyl-3-phenyl-3,6-dihydro-2H-1,2,6-thiadiazine-4-carboxylic acid 1,1-dioxide (8f). To a solution of thiadiazine 6f (2.59 g, 8.34 mmol) in EtOH (10 mL) was added in one portion 2 M KOH (41.5 mL, 83.0 mmol). The reaction mixture was heated to 75° C. and stirred for 3.5 h. The reaction mixture was cooled to rt, diluted with water (10 mL), and acidified with conc. aq. HCl (~5 mL). The aqueous layer was extracted with $Et_2O$ (3x20 mL). The combined organic layers were washed with brine (1x20 mL), dried ($MgSO_4$), filtered, and concentrated under reduced pressure. The crude oil was placed under high vacuum for 6 h to give the desired acid 8f (2.06 g, 88%) as a light yellow solid: Mp 158-161° C. (dec, $Et_2O$); IR (ATR) 3062, 2951, 2626, 2561, 1663, 1279, 1248 $cm^{-1}$; $^1H$ NMR ($CDCl_3$, 400 MHz) δ 8.70 (bs, 1H), 7.56 (s, 1H), 7.37-7.27 (m, 5H), 5.42 (s, 1H), 3.26 (s, 1H), 2.95 (s, 1H); $^{13}C$ NMR ($CDCl_3$, 100 MHz) δ 171.6, 144.4, 137.7, 128.2, 127.7, 100.2, 66.1, 40.3, 37.0; HRMS ($ESI^-$) m/z calcd for $C_{12}H_{13}N_2O_4S$ $[M-H]^-$ 281.0596, found 281.0632.

9g

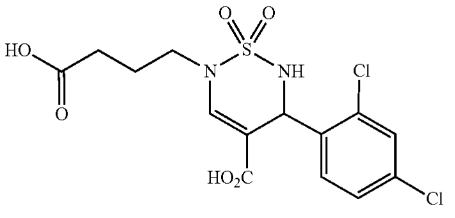

6-(3-Carboxypropyl)-3-(2,4-dichlorophenyl)-3,6-dihydro-2H-1,2,6-thiadiazine-4-carboxylic acid 1,1-dioxide (9g). To a solution of 5g (0.231 g, 0.514 mmol) in EtOH (2.6 mL) was added 2M KOH (3.6 mL, 7.2 mmol) in one portion. The solution was stirred at 80-85° C. for 5 h. Upon completion, the solution was cooled to rt, diluted with EtOAc, and acidified with 5M HCl. The aqueous layer was extracted with EtOAc (3x5 mL). The combined organic layers were washed with brine (15), dried ($Na_2SO_4$), and concentrated to afford 9g (0.110 g, 52%) as an off-white solid: Mp 193-196° C.; IR (ATR) 3168 1718 1660 1631 $cm^{-1}$; $^1H$ NMR (500 MHz, DMSO-$d_6$) δ 12.2 (bs, 2H), 8.55 (bs, 1H), 7.69 (s, 1H), 7.62 (d, 1H, J=2.5 Hz), 7.38 (dd, 1H, J=8.5, 2.5 Hz), 7.24 (d, 1H, J=8.5 Hz), 5.55 (s, 1H), 3.63 (t, 2H, J=7.5 Hz), 3.61 (s, 3H) 2.40 (t, 2H, J=7.5 Hz), 1.85 (dquint, 2H, J=7.0 Hz); $^{13}C$ NMR (125 MHz, DMSO-$d_6$) δ 173.8, 166.1, 143.0, 135.0, 133.9, 133.1, 131.4, 128.7, 126.7, 102.7, 53.8, 48.5, 30.2, 24.8; HRMS ($ESI^+$) m/z calcd for $C_{14}H_{15}Cl_2N_2O_6S$ $[M+H]^+$ 409.0023, found 409.0020. LCMS-ELSD purity 100%.

10g

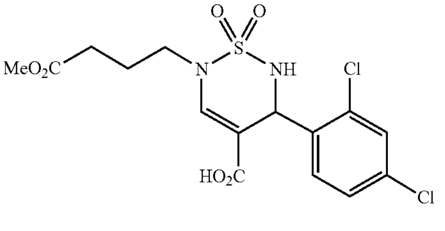

3-(2,4-Dichlorophenyl)-6-(4-methoxy-4-oxobutyl)-3,6-dihydro-2H-1,2,6-thiadiazine-4-carboxylic acid 1,1-dioxide (10g). A solution of compound 9g (0.102 g, 0.249 mmol) in MeOH (3.5 mL) was treated with 0.2 mL of a $H_2SO_4$/MeOH (0.1 mL/25 mL) solution. The reaction mixture was stirred for 6 h at 50° C. Analysis by LCMS indicated >95% conversion to the methyl ester. The mixture was treated with brine (15 mL) and extracted with EtOAc (3x15 mL). The combined organic layers were washed with brine (5 mL), dried ($Na_2SO_4$), filtered, and concentrated to give 10g (0.0981 g, 93%) as an off-white solid: Mp 188-191° C.; IR (ATR, $CH_2Cl_2$) 3162, 3129, 1720, 1674, 1609, 1354, 1169 $cm^{-1}$; $^1H$ NMR (500 MHz; DMSO-$d_6$) δ 12.27 (s, 1H), 8.55 (d, 1H, J=6.9 Hz), 7.70 (s, 1H), 7.38 (dd, 1H, J=8.4, 2.1 Hz), 7.23 (d, 1H, J=8.4 Hz), 5.55 (d, 1H, J=6.4 Hz), 3.63 (t, 2H, J=7.5 Hz), 3.61 (s, 3H), 2.40 (t, 2H, J=7.6 Hz), 1.93-1.84 (m, 2H); $^{13}C$ NMR (126 MHz; DMSO-$d_6$) δ 172.7, 166.1, 143.0, 134.9, 133.9, 133.1, 131.4, 128.7, 126.6, 102.7, 53.8, 51.4, 48.4, 29.9, 24.7; HRMS ($ESI^+$) m/z calcd for $C_{15}H_{15}O_5N_2Cl_2S$ $[M+H]^+$ 405.0073, found 405.0073; LCMS-ELSD purity 100%.

10i

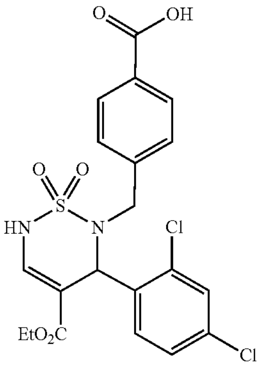

4-((3-(2,4-Dichlorophenyl)-4-(ethoxycarbonyl)-1,1-dioxido-3,6-dihydro-2H-1,2,6-thiadiazin-2-yl)methyl)benzoic acid (10i). A solution of compound 6i (4.80 g, 7.48 mmol) in $CH_2Cl_2$ (25 mL) was treated with TFA (11.1 mL, 150 mmol), and the reaction mixture was stirred at rt under $N_2$. After 1.5 h, TLC (2:1; $CH_2Cl_2$:EtOAc) indicated reaction completion. The reaction mixture was treated with water (~80 mL), and the precipitate was filtered in vacuo to give 10i (3.56 g, 98%) as a white solid: Mp 213-215° C.; IR (ATR, $CH_2Cl_2$) 3185, 1287, 1662, 1634, 1286, 1166 cm-1; $^1H$ NMR (500 MHz; DMSO-$d_6$) δ 12.99 (s, 1H), 11.42 (s, 1H), 7.91 (d, 2H, J=8.1 Hz), 7.54-7.51 (m, 4H), 7.33 (dd, 1H, J=8.5, 2.1 Hz), 7.20 (d, 1H, J=8.5 Hz), 5.64 (s, 1H), 4.55 (d, 1H, J=15.1 Hz), 4.37 (d, 1H, J=15.1 Hz), 4.06-3.94 (m, 2H), 1.07 (t, 3H, J=7.1 Hz); $^{13}C$ NMR (126 MHz; DMSO-$d_6$) δ 167.1, 164.5, 140.3, 139.1, 134.8, 133.9, 133.2, 132.3, 130.2, 129.5, 129.0, 128.5, 126.4, 99.9, 61.3, 59.9, 55.5, 14.0; HRMS ($ESI^+$) m/z calcd for $C_{20}H_{19}O_6N_2Cl_2S$ $[M+H]^+$ 485.0335, found 485.0357; LCMS-220 nm purity 100%.

11f

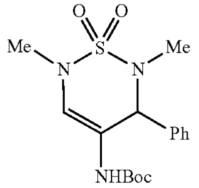

tert-Butyl (2,6-dimethyl-1,1-dioxido-3-phenyl-3,6-dihydro-2H-1,2,6-thiadiazin yl)carbamate (11f). To a suspension of dimethyl thiadiazine carboxylate 8f (0.0770 g, 0.273 mmol) in toluene (0.6 mL) was added TEA (0.0840 mL, 0.598 mmol). The reaction mixture was degassed by FPT (3×), backfilled with Ar, and treated with DPPA (0.0640 mL, 0.297 mmol). The reaction mixture was stirred at rt for 2 h, and heated to 95° C. for 1 h (during which time bubbling occurred for 30 min then stopped). The mixture was then cooled to rt, treated with t-BuOH (0.200 mL, 2.10 mmol) and heated to 100° C. for 3 h. The reaction mixture was cooled to rt, diluted with EtOAc (5 mL) and washed with 1 M NaOH (1×5 mL). The aqueous layer was extracted with EtOAc (3×5 mL). The combined organic layers were washed with sat. aq. $NaHCO_3$ (1×10 mL) and brine (1×10 mL), dried ($Na_2SO_4$), filtered, and concentrated under reduced pressure. The crude material was purified by chromatography on $SiO_2$ (1:9 to 2:8; EtOAc:hexanes), dissolved in $CHCl_3$ and concentrated under reduced pressure (3×) to remove trace EtOAc to give N-Boc amine 11f (21.5 mg, 22%) as a colorless solid: Mp 125-127° C. ($CHCl_3$); IR (ATR) 3336, 2973, 1722 $cm^{-1}$; $^1H$ NMR ($CDCl_3$, 500 MHz) δ 7.45-7.37 (m, 5H), 6.69 (bs, 1H), 5.08 (s, 1H), 4.77 (s, 1H), 3.10 (s, 3H), 2.56 (s, 3H), 1.36 (s, 9H); $^{13}C$ NMR ($CDCl_3$, 125 MHz) δ 152.9, 135.2, 129.6, 129.5, 129.3, 122.2, 119.3, 81.0, 68.7, 38.7, 34.8, 28.3; HRMS ($ESI^+$) m/z calcd for $C_{16}H_{23}N_3O_4SNa$ $[M+Na]^+$ 376.1307, found 376.1346.

11e

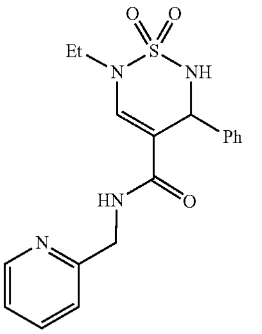

6-Ethyl-3-phenyl-N-(pyridin-2-ylmethyl)-3,6-dihydro-2H-1,2,6-thiadiazine-4-carboxamide 1,1-dioxide (11e). To a solution of monoalkylated thiadiazine 7e (0.101 g, 0.357 mmol), 2-pyridylmethylamine (0.445 mL, 0.428 mmol), EDCI (0.0756 g, 0.394 mmol), and DMAP (0.0267 g, 0.219 mmol) in $CH_2Cl_2$ (0.5 mL) was added DIPEA (0.0445 mL, 0.432 mmol). The reaction mixture was sealed under Ar in a screw cap vial, stirred at rt for 15 h, quenched with sat. aq. $NH_4Cl$ (2 mL), diluted with EtOAc (5 mL), and separated. The aqueous layer was extracted with EtOAc (3×5 mL). The combined organic layers were washed with sat. aq. $NaHCO_3$ (1×5 mL), water (1×5 mL), and brine (1×5 mL), dried ($Na_2SO_4$), decanted, and concentrated under reduced. The crude solid was purified by chromatography on $SiO_2$ (6:94; MeOH:$CH_2Cl_2$) to give amide 11e (0.0950 g, 72%) as a colorless solid: Mp 157-158° C. ($CHCl_3$); IR (ATR) 3333, 3314, 3066, 1644, 1171 $cm^{-1}$; $^1H$ NMR (acetone-$d_6$, 400 MHz) δ 8.41 (ddd, 1H, J=4.8, 1.8, 0.9 Hz), 7.57 (td, 1H, J=7.6, 1.8 Hz), 7.53-7.48 (m, 1H), 7.48-7.44 (m, 2H), 7.41-7.40 (m, 1H), 7.34-7.26 (m, 3H), 7.15 (ddd, 1H, J=7.4, 4.8, 0.8 Hz), 6.98 (d, 1H, J=7.6 Hz), 6.92 (d, 1H, J=7.8 Hz), 5.77 (d, 1H, J=7.4 Hz), 4.45, 4.36 (dd, 2H, J=16.2, 5.7 Hz), 3.64, 3.59 (dq, 2H, J=10.9, 7.2 Hz), 1.30 (t, 3H, J=7.2 Hz); $^{13}C$ NMR (acetone-$d_6$, 100 MHz) δ 166.5, 159.5, 149.6, 139.5, 137.8, 137.2, 129.4, 128.9, 128.7, 122.7, 121.7, 111.6, 59.7, 45.3, 45.2, 15.3; HRMS ($ESI^+$) m/z calcd for $C_{18}H_{21}N_4O_3S$ $[M+H]^+$ 373.1334, found 373.1348.

11g

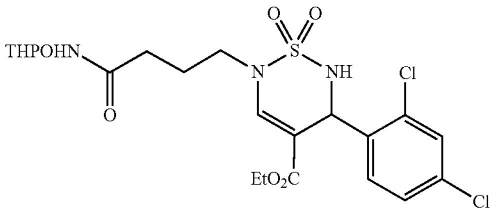

Ethyl 3-(2,4-dichlorophenyl)-6-(4-oxo-4-(((tetrahydro-2H-pyran-2-yl)oxy)amino)butyl)-3,6-dihydro-2H-1,2,6-thiadiazine-4-carboxylate 1,1-dioxide (11g). A solution of compound 7g (0.500 g, 1.143 mmol) in $CH_2Cl_2$ (3 mL) was treated with 0-(tetrahydro-2H-pyran-2-yl)hydroxylamine (0.411 g, 3.51 mmol). The reaction mixture was cooled to 0° C. and treated with $T_3P$ (50% in EtOAc, 1.00 mL, 1.68 mmol) and TEA (0.480 mL, 3.44 mmol). The reaction mixture was warmed to rt, and stirred under $N_2$. After 14 h, the mixture was diluted with $CH_2Cl_2$ (10 mL), washed with 0.25 M HCl (10 mL), brine (10 mL), dried ($Na_2SO_4$), filtered, and concentrated. Purification by chromatography on $SiO_2$ (100% hexanes to 100% EtOAc), afforded 11g (0.470 g, 77%, dr~1:1 based on $^1H$ NMR) as a white solid: $^1H$ NMR (500 MHz; $CDCl_3$) δ 8.47 (s, 1H), 8.40 (s, 1H), 7.45-7.6 (m, 4H), 7.37 (d, 1H, J=8.2 Hz), 7.29-7.26 (m, 1H), 7.21-7.18 (m, 2H), 6.30 (d, 1H, J=6.1 Hz), 5.89 (d, 1H, J=6.8 Hz), 5.85 (d, 1H, J=7.9 Hz), 5.82 (bs, 1H), 5.00 (s, 2H), 4.10-4.00 (m, 4H), 4.00-3.95 (m, 1H), 3.75-3.63 (m, 4H), 3.63-3.54 (m, 2H), 2.28-2.18 (m, 6H), 2.14-2.04 (m, 2H), 1.90-1.72 (m, 6H), 1.52-1.47 (m, 3H), 1.33-1.25 (m, 2H), 1.12-1.08 (m, 6H); HRMS ($ESI^-$) m/z calcd for $C_{21}H_{26}O_7N_3Cl_2S$ $[M-H]^-$ 534.0863, found 534.0859.

11h

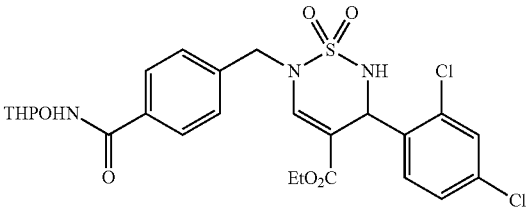

Ethyl 3-(2,4-dichlorophenyl)-6-(4-(((tetrahydro-2H-pyran yl)oxy)carbamoyl)benzyl)-3,6-dihydro-2H-1,2,6-thiadiazine-4-carboxylate 1,1-dioxide (11h). A solution of compound 7h (1.80 g, 3.71 mmol) in $CH_2Cl_2$ (12 mL) was treated with 0-(tetrahydro-2H-pyran-2-yl)hydroxylamine (1.24 g, 10.6 mmol). The mixture was cooled to 0° C., and treated with $T_3P$ (50%, 3.30 mL, 5.54 mmol) and TEA (1.60 mL, 11.5 mmol). The reaction mixture was warmed to rt, and stirred under Na. After 4 h, the mixture was diluted with $CH_2Cl_2$ (150 mL), washed with 0.25 M HCl (100 mL), brine (100 mL), dried ($Na_2SO_4$), filtered, and concentrated. Purification by chromatography on $SiO_2$ (100% hexanes to 100% EtOAc), afforded 11h (1.76 g, 81%, dr ~1:1 based on $^1H$ NMR) as a white solid: Mp 115-117° C. (dec, hexanes); IR (ATR, $CH_2Cl_2$) 3183, 2949, 2871, 1627, 1269, 1176 $cm^{-1}$; $^1H$ NMR (500 MHz; $CDCl_3$) δ 9.35 (s, 1H), 7.64 (app d, 2H, J=8.0 Hz), 7.63 (app d, 2H, J=7.9 Hz), 7.43 (app d, 2H, J=5.5 Hz), 7.41 (app d, 2H, J=2.1 Hz), 7.36 (app dd, 4H, J=8.2, 2.1 Hz), 7.24 (app dd, 2H, J=8.4, 1.5 Hz), 7.17 (app dd, 2H, J=8.4, 2.0 Hz), 6.24-6.20 (m, 2H), 5.91 (app d, 2H, J=7.7 Hz), 5.02 (s, 2H), 4.80 (d, 1H, J=15.9 Hz), 4.78 (d, 1H, J=15.8 Hz), 4.63 (d, 1H, J=15.8 Hz), 4.62 (d, 1H, J=15.9H), 4.03-3.93 (m, 6H), 3.65-3.63 (m, 2H), 1.88-1.81 (m, 8H), 1.66-1.57 (m, 2H), 1.016 (t, 3H, J=7.1 Hz), 1.014 (t, 3H, J=7.1 Hz); $^{13}$C NMR (500 MHz; $CDCl_3$) δ 165.7, 164.9, 141.96, 141.93, 139.47, 139.46, 135.0, 134.7, 133.8, 131.98, 131.97, 130.7, 129.7, 128.37, 128.35, 128.1, 127.0, 105.59, 105.56, 102.9, 62.95, 62.91, 55.5, 52.2, 52.1, 28.2, 25.1, 18.7, 14.1; HRMS (ESI$^-$) m/z calcd for $C_{25}H_{26}O_7N_3Cl_2S$ $[M-H]^-$ 582.0863, found 582.0860.

12g

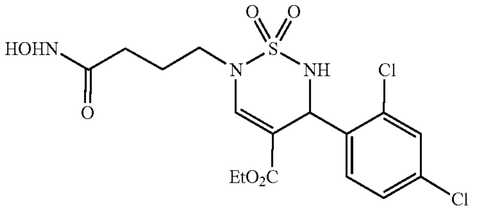

Ethyl 3-(2,4-dichlorophenyl)-6-(4-(hydroxyamino)-4-oxobutyl)-3,6-dihydro-2H-1,2,6-thiadiazine-4-carboxylate 1,1-dioxide (12g). To a solution of 11g (0.465 g, 0.867 mmol) in MeOH (5.0 mL) was added Amberlyst-15 (0.174 g, 818 mmol) at rt under Na. After 21 h of stirring, the reaction mixture was filtered through Celite®, rinsed with MeOH, and concentrated. Purification by chromatography on $SiO_2$* (100% EtOAc) afforded 12g (0.206 g, 53%) as a white solid: Mp 76-78° C.; IR (ATR, $CH_2Cl_2$) 3190, 2985, 1622, 1349, 1167 cm-1; $^{1}$H NMR (400 MHz; DMSO-$d_6$) δ 10.43 (s, 1H), 8.74 (s, 0.9H), 8.60 (d, 1H, J=6.4 Hz), 7.75 (s, 1H), 7.64 (s, 1H), 7.37 (d, 1H, J=8.4 Hz), 7.24 (d, 1H, J=8.4 Hz), 5.59 (d, 1H, J=5.9 Hz), 4.06-3.93 (m, 2H), 3.70-3.57 (m, 2H), 2.03 (t, 2H, J=7.6 Hz), 1.90-1.81 (m, 2H), 1.05 (d, 3H, J=7.0 Hz); $^{13}$C NMR (101 MHz; DMSO-$d_6$) δ 168.3, 164.5, 143.4, 134.8, 133.9, 133.2, 131.4, 128.7, 126.7, 102.1, 59.9, 53.8, 49.0, 34.2, 28.9, 25.6, 14.1; HRMS (ESI+) m/z calcd for $C_{16}H_{20}O_6N_3Cl_2S$ $[M+H]^+$ 452.0444, found 452.046; LCMS-220 nm purity 100%.

*The $SiO_2$ was washed with aqueous 6 M HCl until colorless, neutralized with distilled water, and dried in an oven at 80-100° C. prior to use.

12h

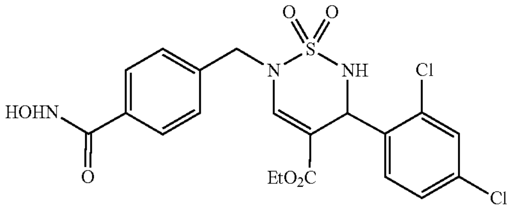

Ethyl 3-(2,4-dichlorophenyl)-6-(4-(hydroxycarbamoyl)benzyl)-3,6-dihydro-2H-1,2,6-thiadiazine-4-carboxylate 1,1-dioxide (12h). To a solution of 11h (0.190 g, 0.325 mmol) in MeOH (5.0 mL) and $CH_2Cl_2$ (1.0 mL) was added Amberlyst-15 (0.0517 g, 253 mmol) at room temperature under $N_2$. After 17 h of stirring, the reaction mixture was filtered through Celite®, rinsed with MeOH, and concentrated. The residue was purified by trituration (4:1; hexanes: EtOAc) to afford 12h (0.133 g, 82%) as a white solid: Mp 97° C. (dec); IR (ATR, $CH_2Cl_2$) 3188, 2862, 1627, 1265, 1175 $cm^{-1}$; $^{1}$H NMR (500 MHz; DMSO-$d_6$) δ 11.24 (s, 1H), 9.06 (s, 1H), 8.76 (d, 1H, J=7.3 Hz), 7.79 (s, 1H), 7.77 (d, 2H, J=8.2 Hz), 7.65 (d, 1H, J=2.2 Hz), 7.46 (d, 2H, J=8.3 Hz), 7.39 (dd, 1H, J=8.5, 2.1 Hz), 7.24 (d, 1H, J=8.5 Hz), 5.64 (d, 1H, J=7.2 Hz), 4.95 (d, 1H, J=16.3 Hz), 4.88 (d, 1H, J=16.3 Hz), 4.03-3.92 (m, 2H), 1.02 (t, 3H, J=7.1 Hz); $^{13}$C NMR (126 MHz; DMSO-$d_6$) δ 164.4, 164.0, 143.2, 139.7, 134.7, 133.9, 133.3, 132.3, 131.3, 128.8, 127.7, 127.2, 126.8, 102.8, 60.0, 54.0, 51.4, 14.0; HRMS (ESI$^+$) m/z calcd for $C_{20}H_{20}O_6N_3Cl_2S$ $[M+H]^+$ 500.0444, found 500.0469; LCMS-220 nm purity 100%.

13e

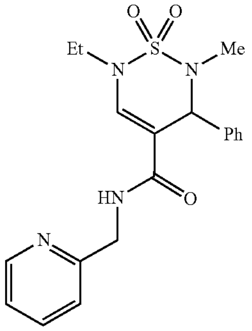

6-Ethyl-2-methyl-3-phenyl-N-(pyridin-2-ylmethyl)-3,6-dihydro-2H-1,2,6-thiadiazine-4-carboxamide 1,1-dioxide (13e). To a vial containing acid 8e (0.0900 g, 0.304 mmol) in $CH_2Cl_2$ (0.85 mL) was added PyBOP (0.173 g, 0.333 mmol), 2-pyridiylmethylamine (34.0 μL, 0.330 mmol), and DIPEA (0.110 mL, 0.632 mmol). The reaction mixture was sealed under Ar and stirred for 23 h at rt. The reaction mixture was diluted with EtOAc (15 mL) and washed with sat. aq. $NH_4Cl$ (1×10 mL). The aqueous layer was extracted with EtOAc (3×10 mL). The combined organic layers were washed with sat. aq. $NaHCO_3$ (1×10 mL) and brine (1×10 mL), dried ($Na_2SO_4$), filtered, and concentrated under reduced pressure. The crude oil was purified by chromatography on $SiO_2$ (6:4; EtOAc:hexanes to 100% EtOAc) to give the amide 13e (0.100 g, 85%) as a colorless foam: IR (ATR) 3307, 1638, 1357, 1165 $cm^{-1}$; $^{1}$H NMR ($CDCl_3$, 500 MHz) δ 8.34 (d, 1H, J=4.8 Hz), 7.59 (dt, 1H, J=7.7, 1.8 Hz), 7.42-7.40 (m, 3H), 7.34-7.26 (m, 3H), 7.15-7.09 (m, 2H), 6.62 (bs, 1H), 5.52 (s, 1H), 4.51, 4.46 (dd, 2H, J=16.5, 4.7 Hz), 3.64 (dq, 2H, J=7.3, 1.8 Hz), 2.84 (s, 3H), 1.35 (t, 3H, J=7.2 Hz); $^{13}$C NMR ($CDCl_3$, 125 MHz) δ 165.9, 156.0, 148.9, 137.5, 136.8, 136.7, 128.9, 128.7, 128.5, 122.3, 122.0, 106.0, 66.5, 45.3, 44.6, 39.0, 15.5; HRMS (ESI$^+$) m/z calcd for $C_{19}H_{23}N_4O_3S$ $[M+H]^+$ 387.1491, found 387.1466.

14e

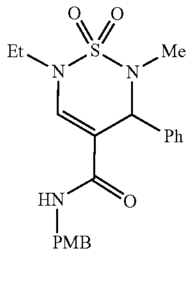

6-Ethyl-N-(4-methoxybenzyl)-2-methyl-3-phenyl-3,6-dihydro-2H-1,2,6-thiadiazine-4-carboxamide 1,1-dioxide (14e). To a solution of acid 8e (0.0974 g, 0.329 mmol), PyBOP (0.2052 g, 0.3944 mmol), and p-methoxybenzylamine (0.0520 mL, 0.398 mmol) in $CH_2Cl_2$ (0.9 mL) was added DIPEA (0.125 mL, 0.718 mmol). The reaction mixture was sealed under and atmosphere of Ar, stirred at rt for 23 h, concentrated under reduced pressure, and partitioned between EtOAc (10 mL) and water (10 mL). The organic layer was washed with 1 M $NaHSO_4$ (2×5 mL), sat. aq. $NaHCO_3$ (1×5 mL), and brine (1×10 mL), dried ($Na_2SO_4$), filtered, and concentrated under reduced pressure. The crude residue was purified by chromatography on $SiO_2$ (2:8 to 1:1; EtOAc:hexanes) to give a light yellow oil that was dissolved in $CHCl_3$ (3×10 mL) and concentrated under reduced pressure to remove trace EtOAc to give amide 14e (0.114 g, 83%) as a light yellow sticky foam: IR (ATR) 3405, 3297, 2973, 2931, 1637, 1357, 1338 $cm^{-1}$; $^1H$ NMR ($CDCl_3$, 500 MHz) δ 7.39 (d, 1H, J=0.7 Hz), 7.39-7.32 (m, 5H), 6.90 (d, 2H, J=8.7 Hz), 6.76-6.74 (m, 2H), 5.41 (s, 1H), 5.30 (t, 1H, J=5.1 Hz), 4.32, 4.23 (dd, 2H, J=14.7, 5.8 Hz), 3.77 (s, 3H), 3.62 (q, 2H, J=7.2 Hz), 2.77 (s, 3H), 1.34 (t, 3H, J=7.2 Hz); $^{13}C$ NMR ($CDCl_3$, 125 MHz) δ 165.6, 159.1, 137.9, 136.4, 130.1, 128.98, 128.96, 128.9, 128.7, 114.1, 105.8, 66.2, 55.4, 45.4, 43.4, 38.4, 15.5; HRMS ($ESI^+$) m/z calcd for $C_{21}H_{26}N_3O_4S$ $[M+H]^+$ 416.1644, found 416.1648.

15e

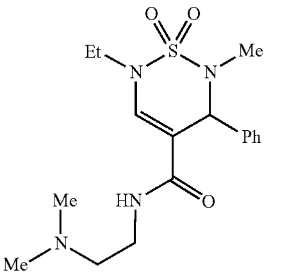

N-(2-(Dimethylamino)ethyl)-6-ethyl-2-methyl-3-phenyl-3,6-dihydro-2H-1,2,6-thiadiazine-4-carboxamide 1,1-dioxide (15e). To a vial containing acid 8e (0.0900 g, 0.304 mmol) in $CH_2Cl_2$ (0.85 mL) was added PyBOP (0.173 g, 0.333 mmol), N,N-dimethylethylene diamine (36.0 μL, 0.330 mmol), and DIPEA (0.110 mL, 0.632 mmol). The reaction mixture was sealed under Ar and stirred for 23 h at rt. The reaction mixture was diluted with EtOAc (15 mL) and washed with sat. aq. $NH_4Cl$ (1×10 mL). The aqueous layer was extracted with EtOAc (3×10 mL). The combined organic layers were washed with sat. aq. $NaHCO_3$ (1×10 mL) and brine (1×10 mL), dried ($Na_2SO_4$), filtered, and concentrated under reduced pressure. The crude material was purified by chromatography on $SiO_2$ (1:99 to 1:9; MeOH:$CHCl_3$) to give amide 15e (0.0847 g, 76%) as a light yellow foam: IR (ATR) 3420, 3307, 2975, 1638, 1357, 1340 $cm^{-1}$; $^1H$ NMR ($CDCl_3$, 500 MHz) δ 7.41-7.29 (m, 5H), 7.37 (s, 1H), 6.04 (bs, 1H), 5.45 (s, 1H), 3.64 (q, 2H, J=7.3 Hz), 3.27-3.18 (m, 2H), 2.79 (s, 3H), 2.39, 2.52 (ddd, 2H, J=12.1, 6.6, 4.9 Hz), 2.06 (s, 6H), 1.35 (3H, J=7.2 Hz); $^{13}C$ NMR ($CDCl_3$, 125 MHz) δ 166.5, 137.7, 136.8, 128.9, 128.7, 128.5, 105.9, 66.3, 57.7, 45.4, 44.7, 38.5, 37.0, 15.5; HRMS ($ESI^+$) m/z calcd for $C_{17}H_{27}N_4O_3S$ $[M+H]^+$ 367.1804, found 367.1797.

16e

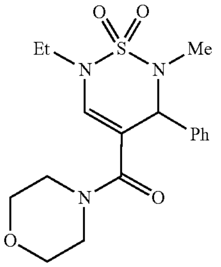

(6-Ethyl-2-methyl-1,1-dioxido-3-phenyl-3,6-dihydro-2H-1,2,6-thiadiazin-4-yl)(morpholino)methanone (16e). To a vial containing acid 8e (0.0900 g, 0.304 mmol) in $CH_2Cl_2$ (0.85 mL) was added PyBOP (0.173 g, 0.333 mmol), morpholine (29.0 uL, 0.332 mmol), and DIPEA (0.110 mL, 0.632 mmol). The reaction mixture was sealed under and atmosphere of Ar and stirred for 23 h at rt. The reaction mixture was diluted with EtOAc (15 mL) and washed with sat. aq. $NH_4Cl$ (1×10 mL). The aqueous layer was extracted with EtOAc (3×10 mL). The combined organic layers were washed with sat. aq. $NaHCO_3$ (1×10 mL) and brine (1×10 mL), dried ($Na_2SO_4$), filtered, and concentrated under reduced pressure. The crude reaction mixture was purified by chromatography on $SiO_2$ (3:7 to 1:1; EtOAc:hexanes) to give amide 16e (0.0933 g, 84%) as a colorless white powder: Mp 116-117° C. ($CHCl_3$); IR (ATR) 2969, 2923, 2852, 1623, 1610, 1357 $cm^{-1}$; $^1H$ NMR ($CDCl_3$, 500 MHz) δ 7.37-7.32 (m, 5H), 6.56 (d, 1H, J=1.6 Hz), 5.68 (d, 1H, J=1.5 Hz), 3.62, 3.58 (dq, 2H, J=14.5, 7.2 Hz), 3.54-3.47 (m, 2H), 3.43-3.34 (m, 4H), 3.34-3.27 (m, 2H), 2.54 (s, 3H), 1.34 (t, 3H, J=7.2 Hz); $^{13}C$ NMR ($CDCl_3$, 125 MHz) δ 167.6, 135.4, 134.2, 129.2, 129.1, 128.7, 109.8, 66.6, 66.5, 45.2, 34.5, 15.3; HRMS ($ESI^+$) m/z calcd for $C_{17}H_{24}N_3O_4S$ $[M+H]^+$ 388.1307, found 388.1314.

17e

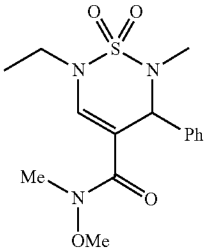

6-Ethyl-N-methoxy-N,2-dimethyl-3-phenyl-3,6-dihydro-2H-1,2,6-thiadiazine-4-carboxamide 1,1-dioxide (17e). To a round bottom flask containing acid 8e (0.999 g, 3.37 mmol), dimethylhydroxylamine hydrochloride (0.441 g, 4.52 mmol), and PyBOP (2.07 g, 3.98 mmol) was added $CH_2Cl_2$ (9.9 mL). The solution was cooled to 0° C. and treated with DIPEA (2.05 mL, 11.8 mmol), slowly warmed to rt, and stirred for 23 h. The reaction mixture was concentrated under reduced pressure and partitioned between EtOAc (40 mL) and water (20 mL). The organic layer was washed with 1 M $NaHSO_4$ (2×20 mL), sat. aq. $NaHCO_3$ (1×20 mL), and brine (1×20 mL), dried ($Na_2SO_4$), filtered, and concentrated under reduced pressure. The crude residue was purified by chromatography on $SiO_2$ (2:8 to 1:1; EtOAc:hexanes) to give a light yellow oil. The oil was dissolved in $CHCl_3$ (3×10 mL) and concentrated under reduced pressure to remove trace EtOAc to give 17e (1.03 g, 90%) as a light yellow sticky oil: IR (ATR) 2977, 2936, 1627, 1163 $cm^{-1}$; $^{1}H$ NMR ($CDCl_3$, 500 MHz) δ 7.36-7.31 (m, 5H), 7.05 (d, 1H, J=1.8 Hz), 5.92 (d, 1H, J=1.8 Hz), 3.65, 3.61 (dq, 2H, J=14.4, 7.2 Hz), 3.54 (s, 3H), 2.99 (s, 3H), 2.43 (s, 3H), 1.36 (t, 3H, J=7.2 Hz); $^{13}C$ NMR ($CDCl_3$, 125 MHz) δ 167.7, 137.7, 136.1, 129.2, 128.7, 128.6, 108.4, 65.7, 61.1, 45.1, 34.0, 33.2, 15.5; HRMS ($ESI^+$) m/z calcd for $C_{15}H_{22}N_3O_4S$ $[M+H]^+$ 340.1331, found 340.1330.

17f

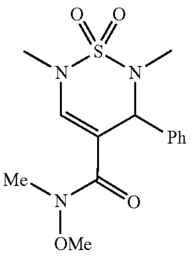

N-Methoxy-N,2,6-trimethyl-3-phenyl-3,6-dihydro-2H-1,2,6-thiadiazine-4-carboxamide 1,1-dioxide (17f). To a solution of acid 8f (5.0772 g, 17.984 mmol), dimethylhydroxylamine hydrochloride (2.330 g, 23.89 mmol), PyBOP (11.306 g, 21.730 mmol) was added $CH_2Cl_2$ (51 mL) and stirred at rt for 5 min then cooled to 0° C. for 10 min. The cooled solution was treated dropwise over 5 min with DIPEA (10.95 mL, 62.92 mmol) and slowly warmed to rt and stirred for 24.25 h. The reaction mixture was diluted with EtOAc (150 mL) and water (100 mL). The organic layer was separated and washed with 1 M $NaHSO_4$ (2×50 mL), sat. aq. $NaHCO_3$ (1×50 mL), and brine (1×50 mL), dried ($Na_2SO_4$), filtered, and concentrated under reduced pressure. The crude material was purified by chromatography on $SiO_2$ (2:8 to 1:1; EtOAc:hexanes) to give a light yellow oil that was dissolved in $CHCl_3$ (100 mL) and washed with 1 M $NaHSO_4$ (2×50 mL), $NaHCO_3$ (1×50 mL), and brine (1×50 mL), dried ($Na_2SO_4$), filtered, and concentrated under reduced pressure to give the amide 17f (5.50 g, 94%) a light yellow oil: IR (ATR) 2936, 1629, 1163 $cm^{-1}$; $^{1}H$ NMR ($CDCl_3$, 400 MHz) δ 7.35-7.29 (m, 5H), 6.96 (d, 1H, J=1.8 Hz), 5.91 (d, 1H, J=1.8 Hz), 3.53 (s, 3H), 3.25 (s, 3H), 2.97 (s, 3H), 2.46 (s, 3H); $^{13}C$ NMR ($CDCl_3$, 100 MHz) δ 167.6, 139.2, 135.9, 129.2, 128.7, 128.6, 108.7, 65.7, 61.1, 36.4, 34.0, 33.2; HRMS ($ESI^+$) calcd for $C_{14}H_{20}N_3O_4S$ $[M+H]^+$ 326.1175, found 326.1186.

18g

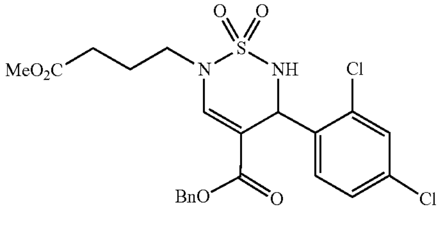

Benzyl 3-(2,4-dichlorophenyl)-6-(4-methoxy-4-oxobutyl)-3,6-dihydro-2H-1,2,6-thiadiazine-4-carboxylate 1,1-dioxide (18g). To a solution of 10g (0.150 g, 0.35 mmol, 1 eq) in $CH_2Cl_2$ (1.7 mL) was sequentially added benzyl alcohol (0.11 mL, 1.063 mmol, 3 eq), EDCI (0.170 g, 0.886 mmol, 2.5 eq), DMAP (0.022 g, 0.180 mmol, 0.5 eq), and TEA (125 μL, 0.886 mmol, 2.5 eq). Reaction progress was monitored by TLC (3:7; EtOAc:hexanes). After stirring at rt for 25 h, the reaction mixture was quenched with $NaHCO_3$ (2 mL) and extracted with $CH_2Cl_2$ (3×2 mL). The combined organic layers were washed with brine (10 mL), dried ($Na_2SO_4$), filtered, and concentrated. Purification by chromatography on $SiO_2$ (3:7, EtOAc:hexanes) afforded 18g (0.109 g, 60%) as a clear foam: Mp 47-49° C.; IR (ATR) 3210 3033, 2953, 2852, 1731, 1697, 1623, 1588, 1561 $cm^{-1}$; $^{1}H$ NMR (500 MHz, $CDCl_3$) δ 7.54 (s, 1H), 7.38 (d, 1H, J=2 Hz), 7.28 (m, 3H), 7.22 (d, 1H J=8.5 Hz), 7.13 (dd, 1H, J=2, 8.3 Hz), 7.05 (dd, 2H, J=7.5, 2.0 Hz), 5.91 (s, 1H), 5.13 (d, 1H, J=12 Hz), 4.95 (d, 1H, J=12 Hz), 4.90 (brs, 1H), 3.69 (t, 2H, J=7.0 Hz), 3.68 (s, 3H), 2.45 (t, 2H, J=7 Hz), 2.08 (dquint, 2H, J=10.0, 7.0 Hz); $^{13}C$ NMR (125 MHz, $CDCl_3$) δ 173.3, 164.6, 142.9, 135.6, 135.2, 134.7, 133.7, 130.6, 129.8, 128.6, 128.4, 128.2, 127.2, 104.5, 66.5, 55.8, 52.0, 49.7, 30.7, 24.8); HRMS ($ESI^+$) m/z calcd for $C_{22}H_{23}O_6N_2Cl_2S$ $[M+H]^+$ 513.0648, found 513.0663; LCMS-220 nm purity 100%.

19f

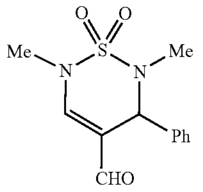

2,6-Dimethyl-3-phenyl-3,6-dihydro-2H-1,2,6-thiadiazine-4-carbaldehyde 1,1-dioxide (19f). To a solution of Weinreb amide 17f (1.2654 g, 3.8890 mmol) in THF (26 mL) cooled to −78° C. was added dropwise $LiAlH_4$ (1 M in $Et_2O$, 7.80 mL, 7.80 mmol) over 5 min. The reaction mixture was stirred for 2 h at −78° C., warmed to 0° C., stirred for 15 min, diluted with $Et_2O$ (80 mL), and quenched with water (100 mL). 1 M HCl (40 mL) was added, the phases were separated, and the aqueous layer was extracted with $Et_2O$ (3×25 mL). The combined organic layers were washed with brine (1×50 mL), dried ($MgSO_4$), filtered, and concentrated under reduced pressure to give a light yellow oil. The crude material was purified by chromatography on $SiO_2$ (4:6 to 6:4; EtOAc:hexanes) to give the aldehyde 19f (0.7267 g, 70%) as a colorless foam: IR (ATR) 1659, 1610, 1363, 1307, 1167 $cm^{-1}$; $^{1}H$ NMR ($CDCl_3$, 400 MHz) δ 9.38 (s, 1H), 7.34-7.26 (m, 5H), 7.13 (s, 1H), 5.51 (s, 1H), 3.35 (s, 3H), 2.93 (s, 3H); $^{13}C$ NMR ($CDCl_3$, 100 MHz) δ 187.7, 150.3, 136.4, 128.3, 127.7, 113.9, 64.8, 39.9, 37.2; HRMS ($ESI^+$) m/z calcd for $C_{12}H_{14}N_2O_3S$ $[M+H]^+$ 267.0803, found.

20f

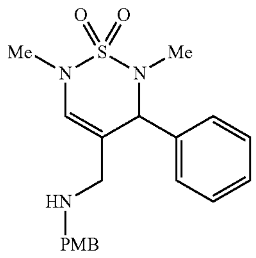

4-(((4-Methoxybenzyl)amino)methyl)-2,6-dimethyl-3-phenyl-3,6-dihydro-2H-1,2,6-thiadiazine 1,1-dioxide (20f).

To a solution of aldehyde 19f (0.0603 g, 0.226 mmol) in $CH_2Cl_2$ (0.28 mL) was added 4-methoxybenzylamine (0.0320 mL, 0.245 mmol) and Ti(i-PrO)$_4$ (0.205 mL, 0.676 mmol). The reaction mixture was sealed under Ar and stirred at rt for 24 h. The reaction mixture was diluted with EtOAc (10 mL), quenched with water (10 mL), stirred at rt for 5 min, and filtered through a pad of Celite®. The organic layer was separated and the aqueous layer was extracted with EtOAc (3×10 mL). The combined organic layers were washed with brine (1×10 mL), dried ($Na_2SO_4$), filtered, concentrated under reduced pressure to give a light yellow oil that was dried under high vacuum for several hours to give the imine that was taken on without further purification.

To a solution of imine in MeOH (0.9 mL) cooled to 0° C. was slowly added $NaBH_4$ (0.0261 g, 0.690 mmol). The reaction mixture was stirred at 0° C. for 30 min and warmed to rt and stirred for 3.5 h. The reaction mixture was diluted with $CH_2Cl_2$ (10 mL), washed with 5% aq. $K_2CO_3$ (2×10 mL) and brine (1×10 mL), dried ($Na_2SO_4$), filtered, and concentrated under reduced pressure. The crude oil was purified by chromatography through a short plug of $SiO_2$ (4:6 to 1:1; EtOAc:hexanes w/2% TEA) to give the amine 20f (0.0604 g, 69%) as a light yellow oil: IR (ATR) 3329, 2900, 2831, 1510, 1241, 1158 cm$^{-1}$; $^1$H NMR ($CDCl_3$, 400 MHz) δ 7.39-7.30 (m, 5H), 7.12 (d, 2H, J=8.2 Hz), 6.82 (d, 2H, J=8.2 Hz), 6.04 (s, 1H), 4.80 (s, 1H), 3.79 (s, 3H), 3.61, 3.51 (d, 2H, J=13.0 Hz), 3.09 (s, 3H), 2.89, 2.85 (d, 2H, J=14.6 Hz), 2.58 (s, 3H), 1.42 (bs, 1H)$^{13}$C NMR ($CDCl_3$, 100 MHz) δ 158.8, 137.1, 132.2, 129.4, 129.1, 128.82, 128.77, 128.3, 121.8, 113.9, 69.1, 55.4, 52.2, 49.8, 38.0, 34.7; HRMS (ESI$^+$) calcd for $C_{20}H_{26}N_3O_3S$ [M+H]$^+$ 388.1695, found 388.1707.

21f

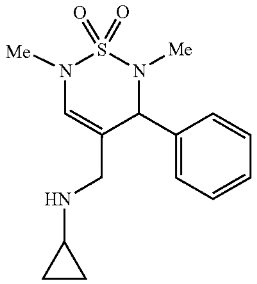

4-((Cyclopropylamino)methyl)-2,6-dimethyl-3-phenyl-3,6-dihydro-2H-1,2,6-thiadiazine 1,1-dioxide (21f). To a solution of aldehyde 19f (0.0603 g, 0.226 mmol) in $CH_2Cl_2$ (0.28 mL) was added cyclopropylamine (0.0170 mL, 0.245 mmol) and Ti(i-PrO)$_4$ (0.200 mL, 0.676 mmol). The reaction mixture was sealed under Ar and stirred at rt for 21 h. The reaction mixture was diluted with EtOAc (10 mL), quenched with brine (10 mL), and filtered through a pad of Celite®. The organic layer was separated and the aqueous layer was extracted with EtOAc (3×10 mL). The combined organic layers were washed with brine (1×10 mL), dried ($Na_2SO_4$), filtered, and concentrated under reduced pressure. The oil was dried under high vacuum overnight to give the imine as a colorless foam that was taken on without purification.

To a solution of imine (0.0691 g, 0.226 mmol) in MeOH (0.4 mL) and THF (0.4 mL) cooled to 0° C. was slowly added $NaBH_4$ (0.0261 g, 0.690 mmol). The reaction mixture was stirred at 0° C. for 15 min then warmed to rt. After 1.5 h the reaction mixture was diluted with $CH_2Cl_2$ (10 mL), washed with 5% aq. $K_2CO_3$ (2×10 mL) and brine (1×10 mL), dried ($Na_2SO_4$), filtered, and concentrated under reduced pressure. The crude oil was purified by chromatography through a short plug of $SiO_2$ (2:8 to 1:1; EtOAc:hexanes w/2% TEA) to give the amine 21f (0.0455 g, 65%) as a colorless solid: Mp 87-88° C. ($CHCl_3$); IR (ATR) 3308, 2839, 1338, 1158, 755, 744 cm$^{-1}$; $^1$H NMR ($CDCl_3$, 400 MHz) δ 7.40-7.30 (m, 5H), 6.03 (s, 1H), 4.74 (s, 1H), 3.08 (s, 3H), 2.94, 2.86 (d, 2H, J=13.7 Hz), 2.55 (s, 3H), 2.00 (m, 1H), 1.41 (bs, 1H), 0.41-0.32 (m, 1H), 0.32-0.24 (m, 2H), 0.12-0.02 (m, 1H); $^{13}$C NMR ($CDCl_3$, 100 MHz) δ 137.0, 129.1, 128.8, 128.1, 122.1, 69.1, 50.4, 38.0, 34.5, 29.8, 6.7, 6.0; HRMS (ESI$^+$) m/z calcd for $C_{12}H_{15}N_2O_2S$ [M−$C_3H_6N$]$^+$ 251.0849, found 251.0841.

Biological Assays: For HD assays, HEK293H cells were grown in DMEM (Sigma-Aldrich, Saint Louis, MO) supplemented with 10% fetal bovine serum (GE Healthcare Hyclone) and 1% penicillin/streptomycin (Thermo Fisher Scientific, Waltham, MA) at 37° C. and at a 5% $CO_2$ atmosphere. Cells were seeded at 250,000 cells/plate in Poly-D-Lysine Coated 35 mm MatTek dishes (P35GC-1.5-10-C, MatTek Corporation, Ashland, MA). After 24 h growth, a total of 4 μg of mCherry tagged-polyglutamine-expanded (17-polyQ-expanded) huntingtin (HTT) was introduced using Lipofectamine 2000 (Invitrogen, Thermo Fisher Scientific) according to the manufacturer's instructions. HTT-17polyQ (Crotti A., et al., Nat Neurosci. 2014, 17(4): 513-21. PMID: 24584051) was fused to mCherry and the HTT-17polyQ-mcherry was cloned between KpnI and BamHI sites in the pcDNA3.1 vector. The following day, cells were treated with vehicle (DMSO) as control or with 10 μM of the examined compounds for 6 h. The cells were then washed with PBS and fixed in 4% formaldehyde for 15 min at room temperature. Finally, cells were stained with DAPI (1:250 in PBS) for 4 h and maintained in PBS for confocal microscope imaging.

Samples were imaged using a Nikon A1 point scanning confocal with a 60× objective and a 1.68 numerical aperture. Complete volumes of cells were acquired at 0.5-μm steps, and volumes were reconstructed and analyzed using Nikon's NIS-Elements software (Nikon Instrument, Melville, NY). Bright spot detection tool was used to identify and quantify the number of protein aggregates ("dots") per cell. A non-parametric Kruskal-Wallis test analysis was performed using Prism software (GraphPad, La Jolla, CA). Statistically significant differences between control (DMSO) and compound treated samples are indicated by asterisks in figure. To obtain representative images from this experiment, maximum intensity projections of 0.5-μm steps though the entire cell were generated using Nikon's NIS-Elements software.

For HDAC 1-3 assays, kits from BioVision Incorporated (https://www.biovision.com/) were used and their recommended protocols followed. For HDAC 4-8 assays, kits from BPS Bioscience (https://bpsbioscience.com/) were used and their recommended protocols followed. For a summary of results, see Table 6. Each compound was dissolved in DMSO to generate a 100 μM stock solution, then diluted using HPLC-grade water to prepare 10 μM, 2 μM, and 1 μM solutions. These solutions were used for the assays. For the HDAC 1-3 assay, samples were subjected to an additional 2× dilution and for HDAC 4, 5, 6, 7, and 8 assays the additional dilution was 10×. The standards Trichostatin A (TSA) and Vorinostat (SAHA) were measured each time an HDAC assay was performed (Table 7). Assays utilized a BioTek Synergy H1 microplate reader and black Nunc MicroWell 96-well optical-bottom plates with polymer base.

HDAC 1-3: 10 μL of each diluted compound (10 μM) and 40 μL of HPLC-grade water were mixed and added into a well on the plate. Different concentrations of TSA and SAHA (for standard curves) were added to their respective wells. 50 μL of HPLC-grade water was added to each positive control well. Then, 50 μL of the reaction mixture was added to each well and the solution was mixed thoroughly. The reaction mixture consisted of 500 μL of 10×HDAC Assay buffer, 100 μL of HeLa nuclear extract, 250 μL of HDAC substrate, and 1.65 mL of HPLC-grade water. The plate was then warmed in an incubator at 37° C. with a rocker platform and was incubated for 30 min. After the incubation, 10 μL of Lysine Developer solution was added to each well. The plate was kept in the incubator for an additional 30 min. Afterwards, the plate was analyzed using a BioTek Synergy H1 microplate reader, taking two independent readings per well that were subsequently averaged.

HDAC 4 (and, by analogy, HDAC 5, 6, 7, and 8): 40 μL of the parent solution was added to each well on the plate. The parent solution was prepared from a fluorogenic HDAC substrate, a 1 mg/mL solution of bovine serum albumin (BSA) in water, and HDAC assay buffer. 5 μL of the inhibitor buffer (10% DMSO in water) was added to the wells designated as "Blank" and "Positive Control" (no inhibitor). 5 μL of the test compound was added to each well designated as "Test Inhibitor". Different concentrations of TSA (for a standard curve) was added to each well designated as "Standard." 5 μL of HDAC assay buffer was added to the "Blank" wells. Then, 5 μL of HDAC 4 human recombinant enzyme was added to the wells designated as "Positive Control", "Test Inhibitor", and "Standard." The plate was then warmed in an incubator at 37° C. with a rocker platform for 30 min After the incubation, 50 μL of 2×HDAC Developer solution was added to each well. The plate was returned to the incubator and was shaken on the rocker for an additional 15 min. at room temperature. Afterwards, the plate was analyzed using a BioTek Synergy H1 microplate reader, taking two independent readings per well that were subsequently averaged.

TABLE 6

Percent inhibition of 10g, 10i, 12g, and 12h in HDAC 1-8 assays

| Entry | Compound | HDAC 1-3[a] | HDAC 4[a] | HDAC 5[b] | HDAC 6[b,c] | HDAC 7[c] | HDAC 8[a,c] |
|---|---|---|---|---|---|---|---|
| 1 | 10g | NIA | NIA | NIA | NIA | 1% | 60%[e] |
| 7 | 10i | NIA | NIA | 9% | 40%[d] | NIA | 37%[e] |
| 8 | 12g | 1% | 5% | NIA | 10%[d] | NIA | 46%[e] |
| 9 | 12h | 22% | 23% | 19% | 20%[d] | 40% | 58%[e] |

[a]Compound tested at 1 uM;
[b]Compound tested at 200 nM;
[c]Compound tested at 100 nM.
[d]Activity was variable, data shown is the average of 2 independent measurements;
[e]Data shown is the average of 2 independent measurements.
NIA = no inhibitory activity noted.

TABLE 7

Percent HDAC inhibition of Trichostatin A (TSA) and Vorinostat (SAHA) positive controls.

| Entry | HDAC | Standard | Concentration (uM) | Percent Inhibition |
|---|---|---|---|---|
| 1 | 1-3 | TSA | 1 | 68% |
| | | | 0.1 | 49% |
| | | | 0.05 | 33% |
| | | | 0.005 | NIA |
| | | | 0.0025 | NIA |
| | | SAHA | 1 | 29% |
| | | | 0.1 | 3% |
| | | | 0.05 | NIA |
| | | | 0.005 | NIA |
| | | | 0.0025 | NIA |
| 2 | 4 | TSA | 10 | 77% |
| | | | 7 | 67% |
| | | | 3 | 35% |
| | | | 1 | 17% |
| | | | 0.5 | NIA |
| 3 | 5 | TSA | 10 | 85% |
| | | | 5 | 73% |
| | | | 2 | 63% |
| | | | 1 | 41% |
| | | | 0.5 | 20% |
| | | | 0.2 | NIA |
| 4 | 6 | SAHA | 0.5 | 94% |
| | | | 0.1 | 82% |
| | | | 0.01 | 47% |
| | | | 0.005 | 25% |
| | | | 0.001 | 6% |
| 5 | 7 | TSA | 5 | 83% |
| | | | 1 | 37% |
| | | | 0.5 | NIA |
| | | | 0.1 | NIA |
| | | | 0.01 | 9% |
| 6 | 8 | TSA | 10 | 97% |
| | | | 5 | 87% |
| | | | 1 | 80% |
| | | | 0.1 | 67% |
| | | | 0.01 | 51% |
| | | SAHA | 5 | 96% |
| | | | 2 | 86% |
| | | | 1 | 70% |
| | | | 0.2 | 67% |
| | | | 0.05 | 54% |

NIA = no inhibitory activity noted.

In summary, a versatile strategy for the preparation and selective functionalization of thiadiazine 1,1-dioxides, a relatively rare heterocycle that has previously been underutilized in medicinal chemistry screening campaigns was developed. The identification of active analogs of Hsp70 agonist, i.e. thiadiazines 10g, 10i, and 12g, in a relevant cell based biological assay highlights the potential application of thiadiazine 1,1-dioxides in hit identification in general, and specifically in Huntington's Disease and perhaps other neurodegenerations associated with the accumulation of toxic protein aggregates.

Figure 4:
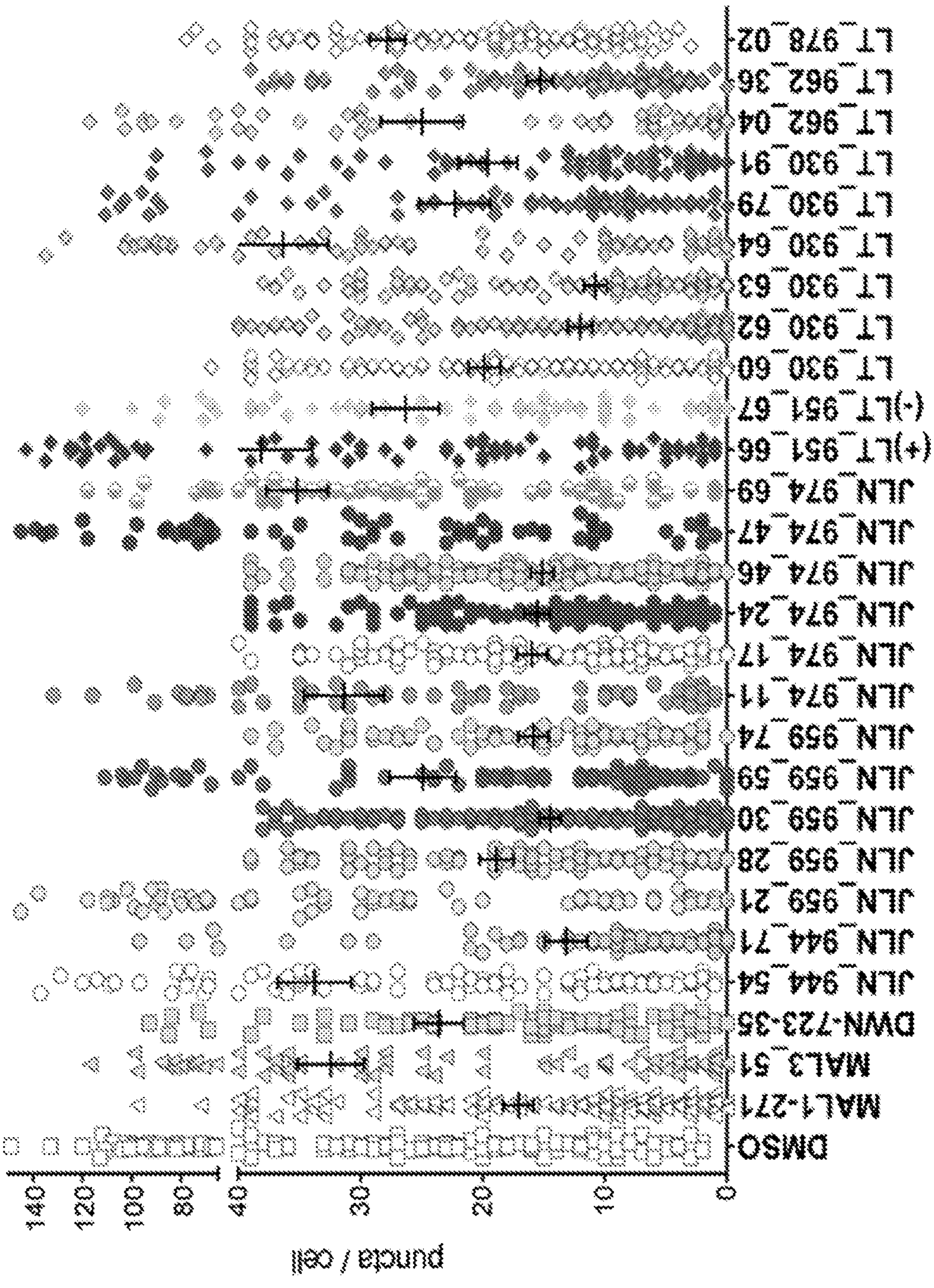
FIG. 4 is a graph showing the effect of treating HEK293H cells transfected with HTT17Q-mCherry (pCAG 17Q HTT-N548) with specific compounds (10 μM) for 6 h.

Example 2: Synthesis and Analysis of Thiadiazine Analogs and Derivatives Thereof The thiadiazine analogs and derivatives thereof according to FIGS. 7-10 were synthesized and investigated for their ability to blunt the formation of toxic aggregates in HEK293 cells that express an HTT17Q-mCherry (pCAG 17Q HTT-N548). See especially FIG. 4. The experimental procedure for synthesis of structures 930-62, 930-63, (+)-951-66, (−)-951-67, 959-30, 959-74, and macrocyclic compounds are provided below.

Experimental Procedures.

2-35

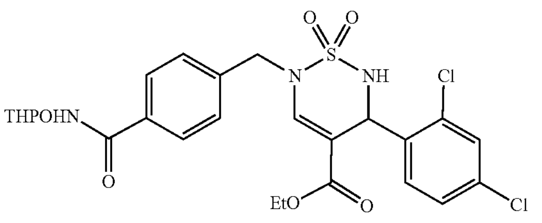

Ethyl 3-(2,4-dichlorophenyl)-6-(4-(((tetrahydro-2H-pyran-2-yl)oxy)carbamoyl)benzyl)-3,6-dihydro-2H-1,2,6-thiadiazine-4-carboxylate 1,1-dioxide (2-35). A solution of carboxylic acid compound 7h (1.80 g, 3.71 mmol) in $CH_2Cl_2$ (12 mL) was treated with O-(tetrahydro-2H-pyran-2-yl)hydroxylamine (1.24 g, 10.6 mmol). The mixture was cooled to 0° C., and treated with $T_3P$ (50%, 3.30 mL, 5.54 mmol) and TEA (1.60 mL, 11.5 mmol). The reaction mixture was warmed to rt, and stirred under $N_2$. After 4 h, the mixture was diluted with $CH_2Cl_2$ (150 mL), washed with 0.25 M HCl (100 mL), brine (100 mL), dried ($Na_2SO_4$), filtered, and concentrated. Purification by chromatography on $SiO_2$ (100% hexanes to 100% EtOAc), afforded 2-35 (1.76 g, 81%, dr ~1:1 based on $^1H$ NMR) as a white solid: Mp 115-117° C. (dec, hexanes); IR ($CH_2Cl_2$) 3183, 2949, 2871, 1627, 1269, 1176 $cm^{-1}$; $^1H$ NMR (500 MHz; $CDCl_3$) δ 9.35 (s, 1H), 7.64 (app d, J=8.0 Hz, 2H), 7.63 (app d, J=7.9 Hz, 2H), 7.43 (app d, J=5.5 Hz, 2H), 7.41 (app d, J=2.1 Hz, 2H), 7.36 (app dd, J=8.2, 2.1 Hz, 4H), 7.24 (app dd, J=8.4, 1.5 Hz, 2H), 7.17 (app dd, J=8.4, 2.0 Hz, 2H), 6.24-6.20 (m, 2H), 5.91 (app d, J=7.7 Hz, 2H), 5.02 (s, 2H), 4.80 (d, J=15.9 Hz, 1H), 4.78 (d, J=15.8 Hz, 1H), 4.63 (d, J=15.8 Hz, 1H), 4.62 (d, J=15.9H, 1H), 4.03-3.93 (m, 6H), 3.65-3.63 (m, 2H), 1.88-1.81 (m, 8H), 1.66-1.57 (m, 2H), 1.016 (t, J=7.1 Hz, 3H), 1.014 (t, 3H, J=7.1 Hz); $^{13}C$ NMR (500 MHz; $CDCl_3$) δ 165.7, 164.9, 141.96, 141.93, 139.47, 139.46, 135.0, 134.7, 133.8, 131.98, 131.97, 130.7, 129.7, 128.37, 128.35, 128.1, 127.0, 105.59, 105.56, 102.9, 62.95, 62.91, 55.5, 52.2, 52.1, 28.2, 25.1, 18.7, 14.1; HRMS ($ESI^+$) m/z calcd for $C_{25}H_{26}O_7N_3Cl_2S$ $[M-H]^-$ 582.0863, found 582.0860.

2-36b

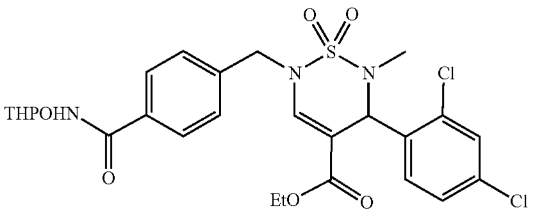

Ethyl 3-(2,4-dichlorophenyl)-2-methyl-6-(4-(((tetrahydro-2H-pyran-2-yl)oxy)carbamoyl) benzyl)-3,6-dihydro-2H-1,2,6-thiadiazine-4-carboxylate 1,1-dioxide (2-36b). A solution of carboxylic acid 2-35 (0.205 g, 0.351 mmol) in acetonitrile (3.0 mL) was treated with $K_2CO_3$ (0.145 g, 1.05 mmol) and methyl iodide (65.0 μL, 1.04 mmol) at rt under $N_2$. After 3 h, LCMS indicated an incomplete reaction, and more $K_2CO_3$ (0.149 g, 1.08 mmol) was added to the reaction mixture. After an additional 2 h of stirring, the reaction mixture was complete and was treated with $H_2O$ (15 mL) and EtOAc (15 mL). The layers were transferred to a separatory funnel and separated. The aqueous layer was extracted with EtOAc (2×20 mL). The combined organic layers were washed with brine (1×15 mL), dried ($Na_2SO_4$), filtered, and concentrated. Purification by chromatography on $SiO_2$ (0-100 EtOAc in hexanes) afforded 2-36b (92% purity by $^1H$ NMR (MeOH), 0.157 g, 69%) as a yellow oil: $^1H$ NMR (500 MHz; $CDCl_3$) δ 8.82 (s, 1H), 7.80 (d, J=8.1 Hz, 2H), 7.50 (s, 1H), 7.47 (d, J=8.1 Hz, 2H), 7.42 (bs, 1H), 7.19-7.15 (m, 2H), 5.51 (s, 1H), 5.09 (s, 1H), 4.82 (app dd, J=15.6, 1.7 Hz, 1H), 4.71 (app dd, J=15.6, 2.2 Hz, 1H), 4.12-3.98 (m, 3H), 3.69-3.65 (m, 1H), 2.96 (s, 3H), 1.93-1.85 (m, 3H), 1.72-1.63 (m, 3H), 1.10 (t, J=7.1 Hz, 3H); HRMS ($ESI^+$) m/z calcd for $C_{26}H_{30}Cl_2N_3O_7S$ $[M+H]^+$ 598.1176, found 598.1177.

930-62

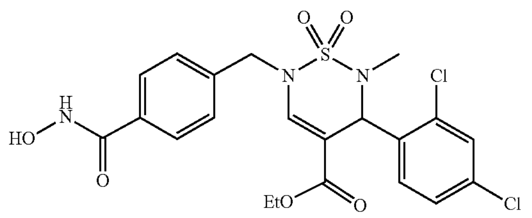

Ethyl 3-(2,4-dichlorophenyl)-6-(4-(hydroxycarbamoyl) benzyl)-2-methyl-3,6-dihydro-2H-1,2,6-thiadiazine-4-carboxylate 1,1-dioxide (930-62). To a solution of 2-36b (92% purity (MeOH), 0.155 g, 0.239 mmol) in MeOH (3.0 mL) and $CH_2Cl_2$ (0.8 mL) was added Amberlyst-15 (0.0439 g, 206 mmol) at room temperature under $N_2$. After 30 h of stirring, the mixture was filtered through Celite, rinsed with MeOH, and concentrated. The residue was purified by trituration (5:1 hexanes; EtOAc) to afford 930-62 (0.109 g, 89%) as an off-white solid: Mp 93° C. (dec.); IR ($CH_2Cl_2$) 3234, 3060, 2984, 1697, 1626, 1372, 1167 $cm^{-1}$; $^1H$ NMR (500 MHz; DMSO-$d_6$) δ 11.23 (s, 1H), 9.06 (s, 1H), 7.95 (s, 1H), 7.77 (d, J=8.3 Hz, 2H), 7.65 (d, J=2.2 Hz, 1H), 7.47 (d, J=8.3 Hz, 2H), 7.37 (dd, J=8.4, 2.2 Hz, 1H), 7.18 (d, J=8.4 Hz, 1H), 5.48 (s, 1H), 4.98 (d, J=16.0 Hz, 1H), 4.88 (d, J=16.0 Hz, 1H), 4.09-3.97 (m, 2H), 2.87 (s, 3H), 1.07 (t, J=7.1 Hz, 3H); $^{13}C$ NMR (126 MHz; DMSO-$d_6$) δ 164.6, 163.9, 142.3, 139.4, 134.6, 134.1, 133.2, 132.5, 131.5, 128.7, 127.8, 127.3, 126.6, 100.1, 62.9, 60.1, 52.1, 14.0; HRMS ($ESI^+$) m/z calcd for $C_{21}H_{22}O_6N_3Cl_2S$ $[M+H]^+$ 514.0601, found 514.0626; LCMS-220 nm purity 100%.

2-36D

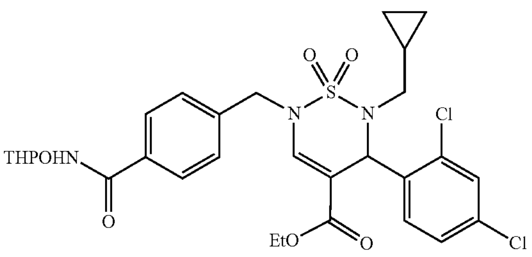

Ethyl 2-(cyclopropylmethyl)-3-(2,4-dichlorophenyl)-6-(4-(((tetrahydro-2H-pyran-2-yl)oxy)carbamoyl)benzyl)-3, 6-dihydro-2H-1,2,6-thiadiazine-4-carboxylate 1,1-dioxide (2-36d). A solution of 2-35 (0.2060 g, 0.352 mmol) in acetonitrile (3.0 mL) was treated with $K_2CO_3$ (0.147 g, 1.06 mmol) and (bromomethyl)cyclopropane (35.0 µL, 0.361 mmol) at rt under $N_2$. After 5 h, LCMS indicated an incomplete reaction, and more $K_2CO_3$ (0.146 g, 1.06 mmol) was added to the reaction mixture. After an additional 2 h, more (bromomethyl)cyclopropane (0.240 mL, 2.47 mmol) was added. After another 24 h of stirring, the reaction mixture was complete and was treated with $H_2O$ (15 mL) and EtOAc (15 mL). The layers were transferred to a separatory funnel and separated. The aqueous layer was extracted with EtOAc (2×20 mL). The combined organic layers were washed with brine (1×15 mL), dried ($Na_2SO_4$), filtered, and concentrated. Purification by chromatography on $SiO_2$ (0-100% EtOAc in hexanes) afforded 2-36d (6% MeOH impurity, 0.117 g, 49%) as a yellow oil: $^1H$ NMR (500 MHz; $CDCl_3$) δ 8.78 (s, 1H), 7.80 (d, J=8.1 Hz, 2H), 7.48 (d, J=8.2 Hz, 2H), 7.46 (s, 1H), 7.40 (d, J=2.0 Hz, 1H), 7.23 (d, J=8.4 Hz, 1H), 7.17 (dd, J=8.4, 2.0 Hz, 1H), 5.91 (s, 1H), 5.09 (s, 1H), 4.80 (d, J=15.9 Hz, 1H), 4.72 (d, J=15.7 Hz, 1H), 4.07 (q, J=7.1 Hz, 2H), 4.03-3.99 (m, 1H), 3.69-3.67 (m, 1H), 3.42 (dd, J=14.4, 6.8 Hz, 1H), 3.18 (dd, J=14.4, 7.3 Hz, 1H), 1.93-1.85 (m, 3H), 1.71-1.57 (m, 3H), 1.21-1.14 (m, 1H), 1.11 (t, J=7.1 Hz, 3H), 0.62-0.54 (m, 2H), 0.31-0.25 (m, 2H); HRMS ($ESI^+$) m/z calcd for $C_{29}H_{34}Cl_2N_3O_7S$ $[M+H]^+$ 638.1489, found 638.1486.

930-63

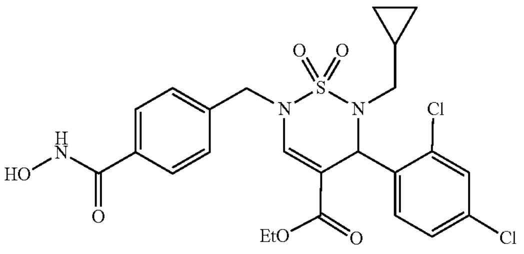

Ethyl 2-(cyclopropylmethyl)-3-(2,4-dichlorophenyl)-6-(4-(hydroxycarbamoyl)benzyl)-3,6-dihydro-2H-1,2,6-thiadiazine-4-carboxylate 1,1-dioxide (930-63). To a solution of 2-36d (94% purity (MeOH), 0.115 g, 0.170 mmol) in MeOH (3.0 mL) and $CH_2Cl_2$ (0.8 mL) was added Amberlyst-15 (0.0340 g, 160 mmol) at rt under $N_2$. After 24 h of stirring, the mixture was filtered through Celite®, rinsed with MeOH, and concentrated. The residue was purified by trituration (10:1; Hexanes:EtOAc) to afford 930-63 (0.0631 g, 67%) as a beige solid: Mp 89° C. (dec.); IR ($CH_2Cl_2$) 3253, 3066, 2981, 1695, 1626, 1371, 1184, 1168 $cm^{-1}$; $^1H$ NMR (500 MHz; DMSO-$d_6$) δ 11.23 (s, 1H), 9.06 (s, 1H), 7.91 (s, 1H), 7.76 (d, J=8.2 Hz, 2H), 7.63 (d, J=2.2 Hz, 1H), 7.46 (d, J=8.2 Hz, 2H), 7.46 (dd, J=8.5, 2.2 Hz, 1H), 7.23 (d, J=8.5 Hz, 1H), 5.82 (s, 1H), 4.96 (d, J=16.0 Hz, 1H), 4.90 (d, J=16.0 Hz, 1H), 4.06-4.02 (m, 2H), 3.28 (dd, J=14.4, 6.8 Hz, 1H), 3.05 (dd, J=14.4, 7.4 Hz, 1H), 1.15-1.09 (m, 1H) 1.07 (t, J=7.0 Hz, 3H), 0.58-0.53 (m, 1H), 0.49-0.45 (m, 1H), 0.26-0.19 (m, 2H); $^{13}C$ NMR (126 MHz; DMSO-$d_6$) δ 164.5, 163.8, 142.6, 139.3, 134.9, 133.9, 133.2, 132.5, 132.0, 128.7, 127.9, 127.2, 126.6, 101.4, 60.3, 60.1, 57.5, 52.3, 14.1, 8.4, 4.4, 3.4; HRMS ($ESI^+$) m/z calcd for $C_{24}H_{26}O_6N_3Cl_2S$ $[M+H]^+$ 554.0914, found 554.0940; LCMS-220 nm purity 98.7%.

2-40

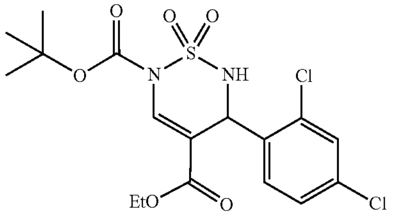

2-(tert-Butyl) 4-ethyl 5-(2,4-dichlorophenyl)-5,6-dihydro-2H-1,2,6-thiadiazine-2,4-dicarboxylate 1,1-dioxide (2-40). A solution of the thiadiazine compound 4d (5.06 g, 14.4 mmol) in acetonitrile (120 mL) was treated with $K_2CO_3$ (4.45 g, 13.2 mmol). After stirring at rt for 25 min, $Boc_2O$ (2.8 g, 13.0 mmol) was added and the reaction mixture was stirred for 7 h. The mixture was treated with $H_2O$ (300 mL), transferred to a separatory funnel, and extracted with EtOAc (3×300 mL). The combined organic layers were washed with brine (200 mL), dried ($Na_2SO_4$), filtered, and concentrated. The residue was purified by chromatography on $SiO_2$ (100% hexanes to 1:1; EtOAc:hexanes) to afford 2-40 (5.08 g, 86%) as a white solid: Mp 56-58° C. (dec.); IR ($CH_2Cl_2$) 3246, 2985, 1745, 1709, 1372, 1254, 1141 $cm^{-1}$; $^1H$ NMR (500 MHz; DMSO-$d_6$) δ 9.36 (d, J=5.5 Hz, 1H), 8.07 (d, J=0.6 Hz, 1H), 7.69 (d, J=2.2 Hz, 1H), 7.38 (dd, J=8.4, 2.2 Hz, 1H), 7.27 (d, J=8.4 Hz, 1H), 5.59 (d, J=5.2 Hz, 1H), 4.12-4.01 (m, 2H), 1.52 (m, 9H), 1.09 (t, J=7.1 Hz, 3H); $^{13}C$ NMR (126 MHz; DMSO-$d_6$) δ 163.7, 147.5, 135.9, 133.9, 133.7, 133.3, 131.4, 128.9, 127.0, 108.2, 86.1, 60.7, 53.1, 27.4, 13.8; HRMS ($ESI^+$) m/z calcd for $C_{17}H_{19}O_6N_2Cl_2S$ $[M-H]^+$ 449.0335, found 449.0333.

2-49

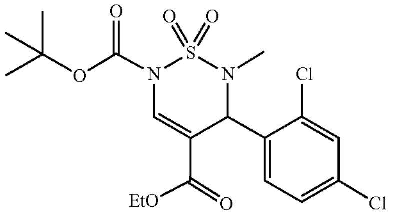

2-(tert-Butyl) 4-ethyl 5-(2,4-dichlorophenyl)-6-methyl-5,6-dihydro-2H-1,2,6-thiadiazine-2,4-dicarboxylate 1,1-dioxide (2-49). To a suspension of carbamate 2-40 (3.40 g, 7.53 mmol) and $K_2CO_3$ (6.25 g, 45.2 mmol) in acetonitrile (30 mL) was added iodomethane (2.81 mL, 45.2 mmol). The reaction mixture was stirred at rt under $N_2$ for 2 h, diluted with water (100 mL) and EtOAc (100 mL). The layers were transferred to a separatory funnel and separated. The aqueous layer was extracted with EtOAc (2×100 mL). The combined organic layers were washed with sat. $NaHCO_3$ (1×10 mL) and brine (1×10 mL), dried ($Na_2SO_4$), filtered, and concentrated to provide 2-49 (3.37 g, 96%) as a white solid: $^1H$ NMR (300 MHz; $CDCl_3$) δ 8.12 (s, 1H), 7.69 (d, J=2.1 Hz, 1H), 7.36 (dd, J=8.4, 2.1 Hz, 1H), 7.23 (d, J=8.4 Hz, 1H), 5.55 (s, 1H), 4.19-4.04 (m, 2H), 3.08 (s, 3H), 1.51 (s, 9H), 1.13 (t, J=7.1 Hz, 3H); HRMS ($ESI^+$) calcd for $C_{18}H_{22}O_6N_2Cl_2NaS$ $[M+Na]^+$ 487.0468, found 487.0457.

2-50

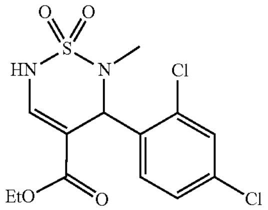

Ethyl 3-(2,4-dichlorophenyl)-2-methyl-3,6-dihydro-2H-1,2,6-thiadiazine-4-carboxylate 1,1-dioxide (2-50). A solution of the carbamate 2-49 (2.48 g, 5.33 mmol) in $CH_2Cl_2$ (13 mL) was treated with TFA (4.00 mL, 53.9 mmol). The reaction mixture was stirred at rt under $N_2$, and after 3 h, TLC (2:1 Hex:EtOAc) indicated reaction completion. The reaction mixture was treated with water (80 mL) and sat. $NaHCO_3$ (80 mL), pH~7-8, transferred to a separatory funnel, and the organic layer was washed with brine (50 mL), dried ($Na_2SO_4$), filtered, and concentrated under vacuum to provide 2-50 (1.89 g, 97%) as a beige solid: Mp 187-189° C.; IR ($CH_2Cl_2$) 3191, 1665, 1626, 1417, 1368, 1287, 1156, 1147 $cm^{-1}$; $^1H$ NMR (500 MHz; DMSO-$d_6$) δ 11.29 (s, 1H), 7.65 (s, 1H), 7.63 (d, J=2.2 Hz, 1H), 7.34 (dd, J=8.4, 2.2 Hz, 1H), 7.17 (d, J=8.4 Hz, 1H), 5.44 (s, 1H), 4.08-3.96 (m, 2H), 2.88 (s, 3H), 1.09 (t, J=7.1 Hz, 3H); $^{13}C$ NMR (500 MHz; DMSO-$d_6$) δ 164.9, 139.1, 135.0, 134.2, 133.0, 131.5, 128.6, 126.5, 98.6, 63.0, 60.0, 39.42, 14.0; HRMS ($ESI^+$) m/z calcd for $C_{13}H_{15}O_4N_2Cl_2S$ $[M+H]^+$ 365.0124, found 365.0120.

Note: HSQC analysis shows the methyl peak overlapping with DMSO-$d_6$ carbon shifts. Methyl carbon of 2-50 and its derivatives is only seen in $^{13}C$ NMR in a concentrated NMR sample. For 2-50, the methyl peak is at 39.42.

Figure 11:
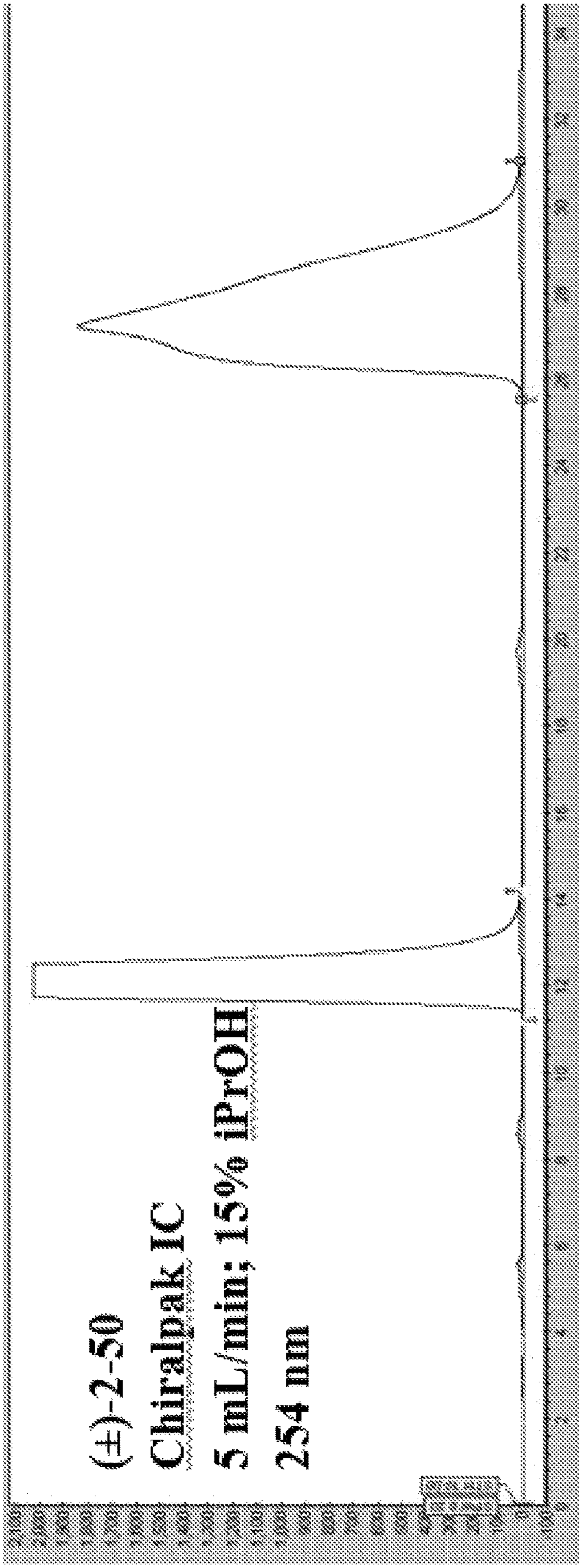
FIG. 11 shows SFC chromatograms of thiadiazine 1,1-dioxide compound identified as 2-50 and its separated enantiomers.
Figure 11:
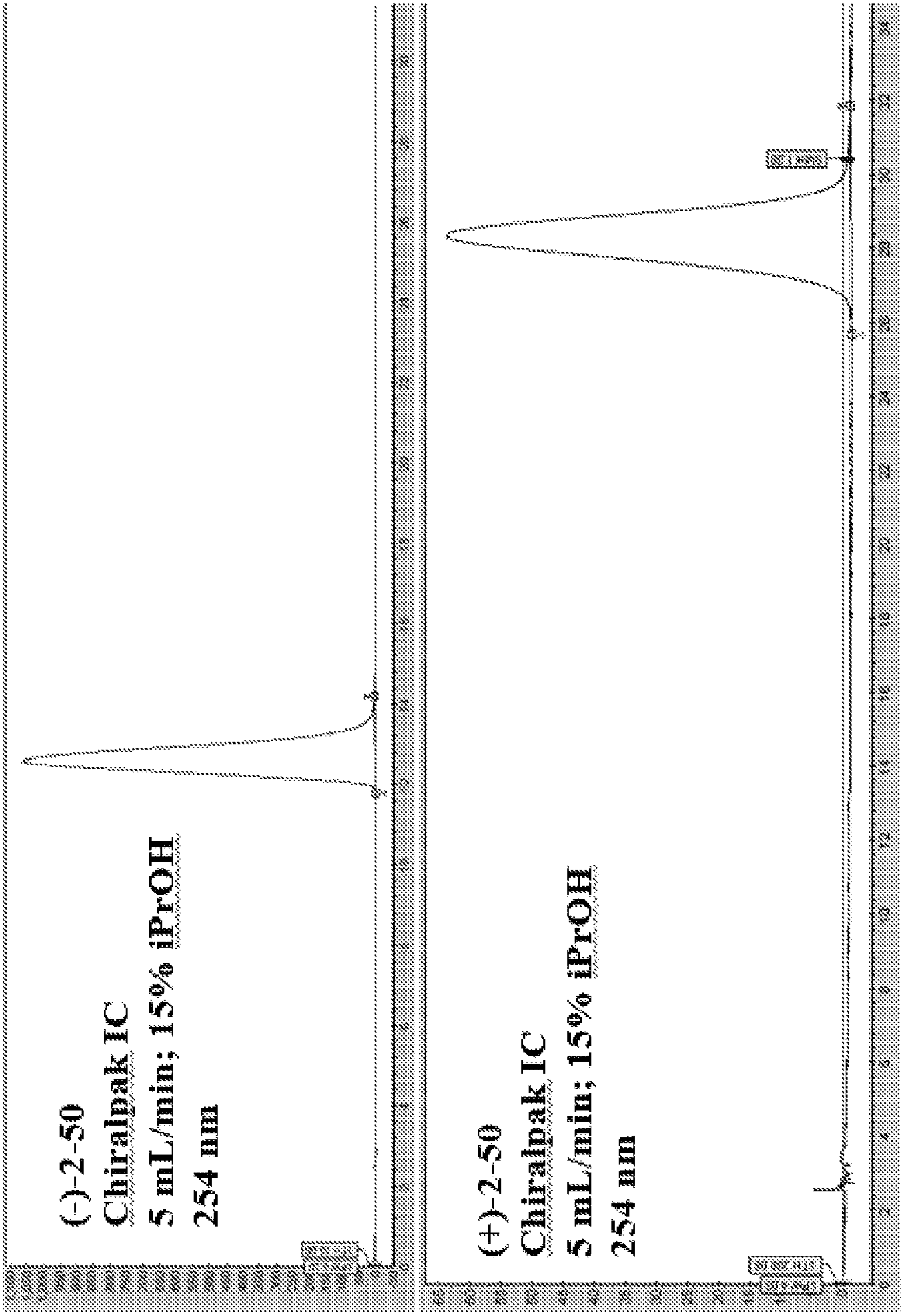

The enantiomers of 2-50 were separated by SFC semi-prep (Chiralpak IC: 5 mL/min; 15% iPrOH; 254 nm). FIG. 11 shows SFC chromatograms of 2-50 and separated enantiomers.

Peak 1 (RT: 12 min) $[\alpha]_D$ −179.1 (c 0.16, $CH_2Cl_2$); Mp 210-212° C.; $^1H$ NMR (300 MHz; DMSO-$d_6$) δ 11.28 (s, 1H), 7.65 (s, 1H), 7.63 (d, J=2.1 Hz, 1H), 7.34 (dd, J=8.4, 2.1 Hz, 1H), 7.17 (d, J=8.4 Hz, 1H), 5.43 (s, 1H), 4.11-3.94 (m, 2H), 2.88 (s, 3H), 1.09 (t, J=7.1 Hz, 3H); HRMS ($ESI^+$) m/z calcd for $C_{13}H_{15}O_4N_2Cl_2S$ $[M+H]^+$ 365.0124, found 365.0119.

Peak 2 (RT: 29 min) $[\alpha]_D$ +135.6 (c 0.16, $CH_2Cl_2$); Mp 178-180° C.; $^1H$ NMR (300 MHz; DMSO-$d_6$) δ 11.28 (s, 1H), 7.65 (s, 1H), 7.63 (d, J=2.1 Hz, 1H), 7.34 (dd, J=8.4, 2.1 Hz, 1H), 7.17 (d, J=8.4 Hz, 1H), 5.43 (s, 1H), 4.10-3.93 (m, 2H), 2.87 (s, 3H), 1.09 (t, J=7.1 Hz, 3H); HRMS ($ESI^+$) m/z calcd for $C_{13}H_{15}O_4N_2Cl_2S$ $[M+H]^+$ 365.0124, found.

(+)-2-52i

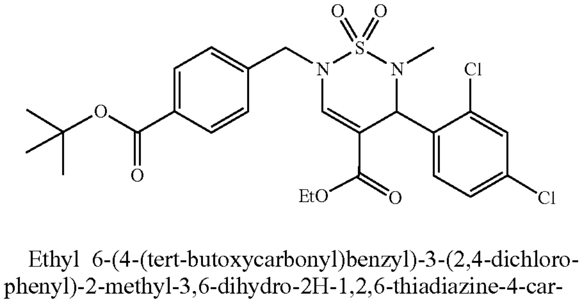

Ethyl 6-(4-(tert-butoxycarbonyl)benzyl)-3-(2,4-dichlorophenyl)-2-methyl-3,6-dihydro-2H-1,2,6-thiadiazine-4-carboxylate 1,1-dioxide ((+)-2-52i). To a suspension of (+)-2-50 (0.0705 g, 0.193 mmol) and $K_2CO_3$ (0.0819 g, 0.593 mmol) in acetonitrile (2.5 mL) was added 4-bromomethyl benzoic acid mono tert-butyl ester (0.0513 g, 0.89 mmol). The reaction mixture was stirred at rt under $N_2$. After 6 h, LCMS indicated SM, and more $K_2CO_3$ (0.0750 g, 0.547 mmol) was added. After an additional 17 h, LCMS indicated reaction completion, and the mixture was suspended in $H_2O$ (15 mL) and EtOAc (15 mL). The layers were transferred to a separatory funnel and separated, and the aqueous layer was extracted with EtOAc (2×10 mL). The combined organic layers were washed with sat. $NaHCO_3$ (10 mL) and brine (10 mL), dried ($Na_2SO_4$), filtered, and concentrated to provide (+)-2-52i (0.106 g, 99%) as a white solid: $^1H$ NMR (300 MHz; $CDCl_3$) δ 8.03 (d, J=8.3 Hz, 2H), 7.50 (s, 1H), 7.44 (d, J=8.4 Hz, 2H), 7.42-7.41 (m, 1H), 7.19-7.16 (m, 2H), 5.51 (s, 1H), 4.84 (d, J=15.4 Hz, 1H), 4.69 (d, J=15.6 Hz, 1H), 4.12-4.00 (m, 2H), 2.96 (s, 3H), 1.60 (s, 9H), 1.10 (t, J=7.1 Hz, 3H); HRMS ($ESI^+$) m/z calcd for $C_{25}H_{32}O_6N_3Cl_2S$ $[M+H]^+$ 572.13834, found 572.13967.

(+)-2-52

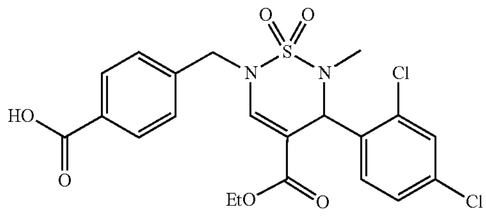

4-((5-(2,4-Dichlorophenyl)-4-(ethoxycarbonyl)-6-methyl-1,1-dioxido-5,6-dihydro-2H-1,2,6-thiadiazin-2-yl)methyl)benzoic acid ((+)-2-52). A solution of tert-butyl ester (+)-2-52i (0.102 g, 0.184 mmol) in $CH_2Cl_2$ (3.5 mL) was treated with TFA (0.136 mL, 1.84 mmol). The reaction mixture was stirred at rt under $N_2$. After 7 h, TLC (2:1 Hex:EtOAc) indicated reaction completion. The mixture was treated with $H_2O$ (5 mL) and sat. $NaHCO_3$ (5 mL), pH~7-8, transferred to a separatory funnel, and the organic layer was washed with brine (5 mL), dried ($Na_2SO_4$), filtered, and concentrated under vacuum to provide (+) 52 (0.0758 g, 83%) as a beige solid: $[\alpha]_D$ +40.9 (c 0.085, MeOH); Mp 92-94° C.; IR ($CH_2Cl_2$) 2929, 1697, 1629, 1378, 1281, 1169 $cm^{-1}$; $^1H$ NMR (300 MHz; DMSO-$d_6$) δ 12.99 (s, 1H), 7.97 (d, J=8.4 Hz, 2H), 7.96 (s, 1H), 7.64 (d, J=2.1 Hz, 1H), 7.52 (d, J=8.2 Hz, 2H), 7.37 (dd, J=8.5, 2.1 Hz, 1H), 7.19 (d, J=8.5 Hz, 1H), 5.49 (s, 1H), 5.02 (d, J=15.9 Hz, 1H), 4.91 (d, J=16.0 Hz, 1H), 4.12-3.94 (m, 2H), 2.87 (s, 3H), 1.07 (t, J=7.1 Hz, 3H); $^{13}C$ NMR (500 MHz; DMSO-$d_6$) δ 167.0, 164.6, 142.4, 141.3, 134.6, 134.1, 133.2, 131.5, 130.4, 129.7, 128.6, 128.0, 126.6, 100.1, 62.9, 60.1, 52.1, 14.0; HRMS ($ESI^+$) m/z calcd for $C_{21}H_{21}O_6N_2Cl_2S$ $[M+H]^+$ 499.04919, found 499.04870.

(+)-951-66

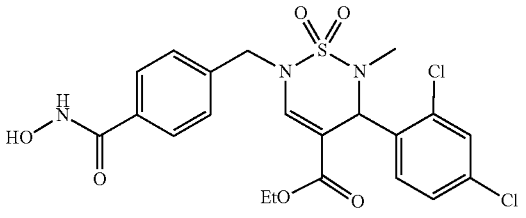

(+)-Ethyl 3-(2,4-dichlorophenyl)-6-(4-(hydroxycarbamoyl) benzyl)-2-methyl-3,6-dihydro-2H-1,2,6-thiadiazine-4-carboxylate 1,1-dioxide ((+)-951-66). A solution of carboxylic acid (+)-2-52 (0.0758 g, 0.152 mmol) in $CH_2Cl_2$ (0.8 mL) was treated with 0-(tetrahydro-2H-pyran-2-yl)hydroxylamine (0.0533 g, 0.456 mmol). The reaction mixture was cooled to 0° C., and treated with $T_3P$ (50%, 0.136 mL, 0.228 mmol) and TEA (0.0635 mL, 0.455 mmol). After warming to rt and stirring under $N_2$ for 9 h, the reaction mixture was diluted with EtOAc (8 mL), washed with 0.5 M HCl (8 mL), brine (8 mL), dried ($Na_2SO_4$), filtered, and concentrated. Purification by chromatography on $SiO_2$ (0-100% EtOAc in hexanes) afforded the amide (0.0616 g, 68%) as a white solid. Characterization was consistent with that of the racemic material. The white solid (0.0600 g, 0.100 mmol) in MeOH (3.0 mL) and $CH_2Cl_2$ (0.8 mL) was treated with Amberlyst-15 (0.0430 g, 202 mmol) at rt under $N_2$. After 17 h of stirring, the mixture was filtered through Celite, rinsed with MeOH, and concentrated. The residue was purified by trituration (5:1 hexanes:EtOAc) to afford (+)-951-66 (0.0330 g, 64%) as an off-white solid: $[\alpha]_D$ +46.0 (c 0.12, MeOH); Mp 105-109° C.; IR ($CH_2Cl_2$) 3241, 3061, 2983, 1670, 1626, 1373, 1167 $cm^{-1}$; $^1H$ NMR (500 MHz; DMSO-$d_6$) δ 11.23 (s, 1H), 9.05 (s, 1H), 7.95 (s, 1H), 7.77 (d, J=8.1 Hz, 2H), 7.64 (d, J=1.8 Hz, 1H), 7.47 (d, J=8.1 Hz, 2H), 7.37 (dd, J=8.4, 1.8 Hz, 1H), 7.18 (d, J=8.4 Hz, 1H), 5.48 (s, 1H), 4.98 (d, J=15.9 Hz, 1H), 4.88 (d, J=15.9 Hz, 1H), 4.09-3.97 (m, 2H), 2.87 (s, 3H), 1.07 (t, J=7.1 Hz, 3H); $^{13}C$ NMR (126 MHz; DMSO-$d_6$) δ 164.6, 163.8, 142.3, 139.4, 134.6, 134.1, 133.2, 132.5, 131.5, 128.7, 127.8, 127.3, 126.6, 100.1, 62.9, 60.1, 52.1, 14.0; HRMS ($ESI^+$) m/z calcd for $C_{21}H_{22}O_6N_3Cl_2S$ $[M+H]^+$ 514.0601, found 514.0578; LCMS-220 nm purity 97.4%.

(-)-2-52l

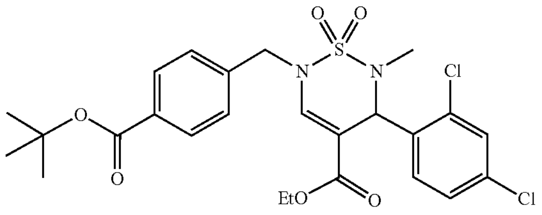

Ethyl 6-(4-(tert-butoxycarbonyl)benzyl)-3-(2,4-dichlorophenyl)-2-methyl-3,6-dihydro-2H-1,2,6-thiadiazine-4-carboxylate 1,1-dioxide ((−)-2-52i). To a suspension of (−)-2-50 (0.0580 g, 0.159 mmol) and $K_2CO_3$ (0.132 g, 0.953 mmol) in acetonitrile (2.5 mL) was added 4-bromomethyl benzoic acid mono tert-butyl ester (0.0431 g, 0.159 mmol). The reaction mixture was stirred at rt under $N_2$. After 23 h, TLC (5:1 Hex:EtOAc) indicated consumption of SM, and the mixture was suspended in $H_2O$ (15 mL) and EtOAc (15 mL). The layers were separated, and the aqueous layer was extracted with EtOAc (2×10 mL). The combined organic layers were washed with sat. $NaHCO_3$ (10 mL) and brine (10 mL), dried ($Na_2SO_4$), filtered, and concentrated to provide (−)-2-52i (0.0880 g, 100%) as a white solid: $^1H$ NMR (300 MHz; $CDCl_3$) δ 8.03 (d, J=8.2 Hz, 2H), 7.50 (s, 1H), 7.44 (d, J=8.2 Hz, 2H), 7.42-7.41 (m, 1H), 7.19-7.17 (m, 2H), 5.51 (s, 1H), 4.84 (d, J=15.5 Hz, 1H), 4.69 (d, J=15.5 Hz, 1H), 4.13-3.98 (m, 2H), 2.96 (s, 3H), 1.60 (s, 9H), 1.10 (t, J=7.1 Hz, 3H); HRMS ($ESI^+$) m/z calcd for $C_{25}H_{32}O_6N_3Cl_2S$ $[M+H]^+$ 572.13834, found 572.13947.

(-)-2-52

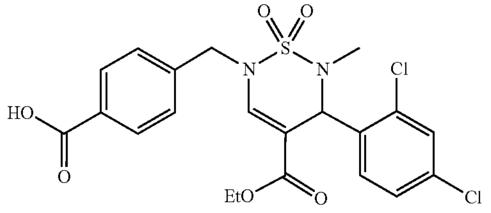

4-((5-(2,4-Dichlorophenyl)-4-(ethoxycarbonyl)-6-methyl-1,1-dioxido-5,6-dihydro-2H-1,2,6-thiadiazin-2-yl) methyl)benzoic acid ((−)-2-52). A solution of tert-butyl ester (−)-2-52i (0.0850 g, 0.153 mmol) in $CH_2Cl_2$ (3.0 mL) was treated with TFA (0.114 mL, 1.53 mmol). The reaction mixture was stirred at rt under $N_2$. After 7 h, TLC (2:1 Hex:EtOAc) indicated reaction completion. The mixture was treated with $H_2O$ (5 mL) and sat. $NaHCO_3$ (5 mL), pH~7-8, and the organic layer was washed with brine (5 mL), dried ($Na_2SO_4$), filtered, and concentrated under vacuum to provide (−)-2-52 (0.0697 g, 91%) as a beige solid: $[\alpha]_D$ −40.7 (c 0.086, MeOH); Mp 92-94° C.; IR ($CH_2Cl_2$) 2924, 1695, 1628, 1376, 1280, 1168 $cm^{-1}$; $^1H$ NMR (300 MHz; DMSO-$d_6$) δ 12.99 (s, 1H), 7.97 (d, J=8.4 Hz, 2H), 7.96 (s, 1H), 7.64 (d, J=2.1 Hz, 1H), 7.52 (d, J=8.2 Hz, 2H), 7.37 (dd, J=8.5, 2.1 Hz, 1H), 7.19 (d, J=8.5 Hz, 1H), 5.49 (s, 1H), 5.02 (d, J=16.0 Hz, 1H), 4.91 (d, J=16.0 Hz, 1H), 4.12-3.94 (m, 2H), 2.87 (s, 3H), 1.07 (t, J=7.1 Hz, 3H); HRMS ($ESI^+$) calcd for $C_{21}H_{21}O_6N_2Cl_2S$ $[M+H]^+$ 499.04919, found 499.04860.

(-)-951-67

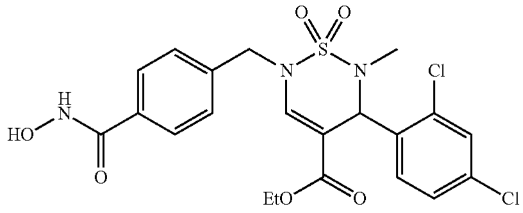

(−)-Ethyl 3-(2,4-dichlorophenyl)-6-(4-(hydroxycarbamoyl)benzyl)-2-methyl-3,6-dihydro-2H-1,2,6-thiadiazine-4-carboxylate 1,1-dioxide ((−)-951-67). A solution of carboxylic acid (−)-2-52 (0.0700 g, 0.140 mmol) in $CH_2Cl_2$ (1.2 mL) was treated with 0-(tetrahydro-2H-pyran-2-yl)hydroxylamine (0.0980 g, 0.837 mmol). The reaction mixture was cooled to 0° C., and treated with $T_3P$ (50%, 0.125 mL, 0.210 mmol) and TEA (0.0586 mL, 0.421 mmol). After warming to rt and stirring under $N_2$ for 14 h, the reaction mixture was diluted with EtOAc (8 mL), washed with 0.5 M HCl (8 mL), brine (8 mL), dried ($Na_2SO_4$), filtered, and concentrated. Purification by chromatography on $SiO_2$ (0-100% EtOAc in hexanes) afforded the amide (0.0510 g, 61%) as a white solid. Characterization was consistent with that of the racemic material. To a solution of the white solid (0.0510 g, 0.0852 mmol) in MeOH (2.5 mL) and $CH_2Cl_2$ (0.8 mL) was added Amberlyst-15 (0.0310 g, 146 mmol) at rt under $N_2$. After 17 h of stirring, the reaction mixture was filtered through Celite, rinsed with MeOH, and concentrated. The residue was purified by trituration (5:1 hexanes:EtOAc) to afford (−)-951-67 (0.0370 g, 84%) as an off-white solid: $[\alpha]_D$ −43.0 (c 0.12, MeOH); Mp 126-129° C.; IR ($CH_2Cl_2$)

3221, 2983, 1698, 1627, 1375, 1168 $cm^{-1}$; $^1H$ NMR (500 MHz; DMSO-$d_6$) δ 11.24 (s, 1H), 9.07 (s, 1H), 7.96 (s, 1H), 7.78 (d, J=8.2 Hz, 2H), 7.65 (d, J=2.1 Hz, 1H), 7.48 (d, J=8.2 Hz, 2H), 7.38 (dd, J=8.4, 2.1 Hz, 1H), 7.19 (d, J=8.4 Hz, 1H), 5.49 (s, 1H), 4.98 (d, J=15.9 Hz, 1H), 4.89 (d, J=15.9 Hz, 1H), 4.10-3.97 (m, 2H), 2.88 (s, 3H), 1.07 (t, J=7.1 Hz, 3H); $^{13}C$ NMR (126 MHz; DMSO-$d_6$) δ 164.6, 163.9, 142.3, 139.4, 134.6, 134.1, 133.2, 132.5, 131.5, 128.7, 127.8, 127.3, 126.6, 100.1, 62.9, 60.1, 52.1, 14.0; HRMS ($ESI^+$) m/z calcd for $C_{21}H_{22}O_6N_3Cl_2S$ $[M+H]^+$ 514.0601, found 514.0581; LCMS-220 nm purity 98.4%.

10g-1

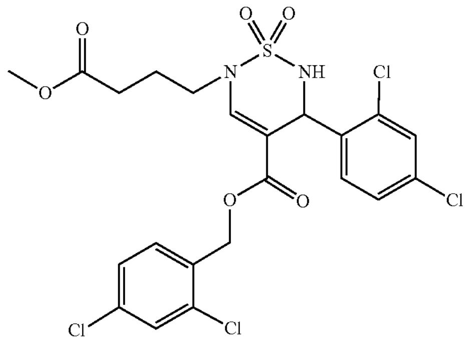

Methyl 4-(4-(2,4-dichlorobenzyl)-5-(2,4-dichlorophenyl)-1,1-dioxido-5,6-dihydro-2H-1,2,6-thiadiazin-2-yl)butanoate (10g-1): To a solution of 10g (100 mg, 1.0 eq) in DCM (1.2 mL, [rxn]=0.2 M) was added 2,4 dichloro benzyl alcohol (169 mg, 4.0 eq), EDCI (137 mg, 0.71 mmol, 3.0 eq), DMAP (29.0 mg, 1.0 eq), and TEA (0.1 mL, 3.0 eq) under $N_2$. The resulting colorless solution was stirred at rt for 23 hours. Reaction progress was monitored with TLC (eluent—30% EtOAc in hexane). Upon completion, the solution was diluted with DCM (5.0 mL) and $NaHCO_3$ (5.0 mL). Aqueous phase was extracted with DCM (5.0 mL*3). Organic layers were combined, washed with brine, dried over $Na_2SO_4$, concentrated and purified with column chromatography (eluent—30% EtOAc in hexane) to afford product as clear film (24% yield): IR (ATR, $CH_2Cl_2$) 3234, 2926, 2855, 1708, 1624, 1591 $cm^{-1}$; $^1H$ NMR (500 MHz; $CDCl_3$) δ 7.55 (1H, s), 7.35 (2H, dd, J=2.0, 8.0 Hz), 7.15 (1H, d, J=2.0 Hz), 7.14-7.11 (2H, m), 6.97 (2H, d, J=1.0 Hz), 5.89 (1H, d, J=14 Hz), 5.19 (1H, d, J=14 Hz), 4.99-4.97 (2H, m), 3.69-3.66 (5H, m), 2.44 (2H, t, J=7.5 Hz), 2.02-2.12 (2H, m); $^{13}C$ NMR (125 MHz; $CDCl_3$) δ 173.3, 164.3, 143.3, 135.2, 135.1, 134.7, 131.9, 131.0, 130.6, 129.6, 127.2, 127.1, 104.0, 63.2, 55.7, 52.1, 49.8, 30.7, 24.8; HRMS ESP m/z calcd for $C_{22}H_{21}O_6N_2Cl_4S$ [M+H 580.98689, found 580.98645.

959-30

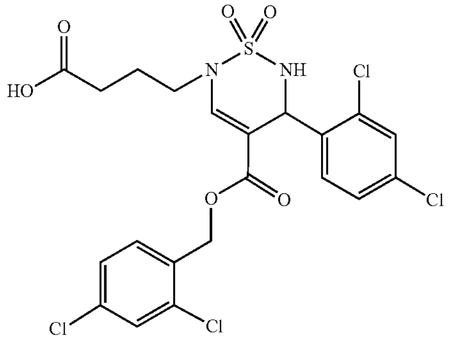

4-(4-(2,4-dichlorobenzyl)-5-(2,4-dichlorophenyl)-1,1-dioxido-5,6-dihydro-2H-1,2,6-thiadiazin-2-yl)butanoic acid (959-30): To the solution of (10g-1) (36 mg, 1.0 eq) in THF/$H_2O$ (0.6 mL, [rxn]=0.1 M) was added LiOH·$H_2O$ (5.0 mg, 2.0 eq) in one portion. The solution was stirred at rt for 1h. Reaction progress was monitored with TLC (eluent=30% EtOAc in hexane). Upon completion, the solution was diluted with EtOAc (2.0 mL) and acidified until pH=3 with 5M HCl. Aqueous layer was extracted with EtOAc (2.0 mL*3). Organic layers were combined, washed with brine, dried over $Na_2SO_4$. Crude was further purified with chromatography (Eluent: 2% MeOH in DCM spiked with 0.5% AcOH) to afford title compound as colorless foam. Yield: 67%; $^1H$ NMR (500 MHz; DMSO-$d_6$) δ 8.66 (1H, d, J=1.0 Hz), 7.82 (1H, s), 7.59-7.58 (2H, m), 7.37 (1H, dd, J=2.0, 8.0 Hz), 7.32 (1H, dd, J=2.0, 8.0 Hz), 7.23-7.21 (2H, m), 5.61 (1H, d, J=1.0 Hz), 5.16 (1H, d, J=14 Hz), 5.02 (1H, d, J=14 Hz), 3.67 (2H, t, J=7.5 Hz), 2.31 (2H, t, J=7.5 Hz), 1.91-1.83 (2H, m); $^{13}C$ NMR (125 MHz; DMSO-$d_6$) δ 173.8164.0, 144.1, 134.5, 133.9, 133.5, 133.3, 132.6, 131.4, 131.1, 128.8, 128.7, 127.2, 126.7, 62.2, 53.7, 48.7, 30.2, 24.9; HRMS $ESI^+$ m/z calcd for $C_{21}H_{19}O_6N_2Cl_4S$ $[M+H]^+$ 566.97124, found 566.97171.

18g-1

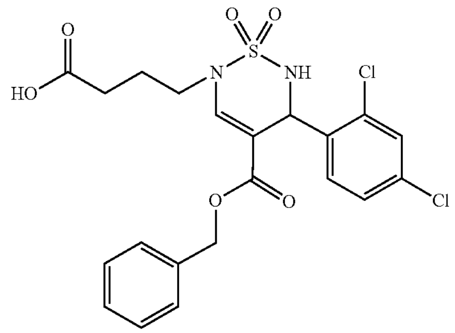

4-(4-((benzyloxy)carbonyl)-5-(2,4-dichlorophenyl)-1,1-dioxido-5,6-dihydro-2H-1,2,6-thiadiazin-2-yl)butanoic acid (18g-1): To a solution of (18g) (270 mg, 1.0 eq) in 1/1 THF/MeOH (5.3 mL, [rxn]=0.1 M) was added LiOH·$H_2O$ (1M solution, 1.1 mL, 1.10 mmol, 2.0 eq). The resulting solution was stirred at rt for 2 hours. Reaction progress was done with TLC. Upon completion, the solvent was removed under reduced pressure and the residue was partitioned between $H_2O$ (50 mL) and DCM (50 mL). Aqueous layer was acidified with 1M HCl until pH=3 and extracted with 10% MeOH in DCM (50 mL*3). Organic layer was dried over $MgSO_4$ and concentrated to afford product as clear foam; Yield: 80.1%; $^1H$ NMR (500 MHz; $CDCl_3$) δ 7.55 (1H, s), 7.36 (1H, d, J=2.0), 7.29-7.27 (2H, m, overlapping with $CDCl_3$), 7.19 (1H, d, J=8.0 Hz), 7.11 (1H, dd, J=2.0, 8.0 Hz), 7.03-7.01 (2H, m), 5.87 (1H, d, J=8.0 Hz), 5.18 (1H, d, J=8.0 Hz), 5.09 (1H, d, J=12.5 Hz), 4.92 (1H, d, J=12.5 Hz), 3.72-3.62 (2H, m), 2.48 (2H, t, J=7.2 Hz), 2.06 (2H, q, J=7.2 Hz); $^{13}C$ NMR (125 MHz; $CDCl_3$) δ 177.3, 164.8, 142.9, 135.4, 135.1, 134.6, 133.6, 130.6, 129.8, 128.6, 128.4, 128.1, 127.1, 104.4, 66.6, 55.6, 49.3, 30.4, 24.5

959-74

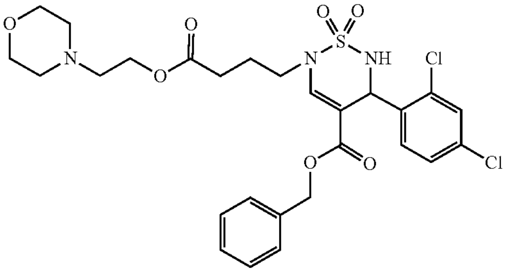

Benzyl 3-(2,4-dichlorophenyl)-6-(4-(2-morpholinoethoxy)-4-oxobutyl)-3,6-dihydro-2H-1,2,6-thiadiazine-4-carboxylate 1,1-dioxide (959-74): To a suspension of (18g-1) (210 mg, 1.0 eq) in DCM (7.0 mL, [rxn]=0.06 M), was added EDCI (97 mg, 1.2 eq), HOBt (68 mg, 1.2 mmol), and DMAP (25 mg, 0.5 eq). After 30 mins of activation, 2-morpholinoethan-1-ol (61 microL, 1.2 eq) was added to the reaction. The resulting yellow solution was stirred for 42 hours. Then, the solution was transferred to a separatory funnel, washed with 1M HCl (50 mL), saturated $Na_2CO_3$ (50 ml), $H_2O$ (30 mL*3), and brine. Organic layer was dried over $Na_2SO_4$, concentrated and purified with column chromatography (10% MeOH in EtOAc; $R_f$: 0.4) to afford title compound as clear foam; Yield: 62%; IR (ATR, DCM): 2953, 1720, 1626 $cm^{-1}$; $^1H$ NMR (500 MHz; $CDCl_3$) δ 7.55 (1H, s), 7.36 (1H, d, J=2.0 Hz), 7.24-7.27 (2H, m, overlapping with $CDCl_3$), 7.22 (2H, d, J=8.5 Hz), 7.12 (1H, dd, J=2.0, 8.5 Hz), 7.03 (2H, d, J=6.0 Hz), 5.88 (2H, s) 5.11 (1H, d, J=12 Hz), 4.93 (1H, d, J=12 Hz) 4.20 (2H, t, J=5.5 Hz), 3.68-3.65 (6H, m), 2.61 (2H, t, J=5.5 Hz), 2.48 (3H, s), 2.43 (3H, t, J=7.0 Hz), 2.05 (2H, q, J=7.0 Hz); $^{13}C$ NMR (125 MHz; $CDCl_3$) δ 172.7, 164.6, 142.9, 135.5, 135.0, 134.6, 133.8, 130.7, 129.7, 128.3, 128.0, 127.0, 104.2, 66.9, 66.5, 61.7, 57.1, 55.4, 53.9, 49.3, 30.8, 24.8; HRMS $ESI^+$ m/z calcd for $C_{27}H_{32}O_7N_3Cl_2S$ $[M+H]^+$ 612.13325, found 612.13382.

Synthesis of thiadiazine-containing macrocycle: As illustrated in Scheme 5, heterocycle 4d was subjected to Mitsunobu alkylation with homo allylic alcohol to give rise to 5.4. In consideration of the chelation of $N_3$ to the Ru catalyst, the $N_3$ activity was secured with a methyl group. The methyl-substituted product was hydrolyzed and alkylated with allylic bromide to furnish corresponding precursor 5.5. 5.5 was subjected to RCM under refluxing DCM in the presence of 6 mol % second generation Hoveyda-Grubbs catalyst (labelled as Ru—C). Dimerized product was isolated with 11% yield. This unsaturated dimer was further reduced with $H_2$ and Pd/C to 5.7, and the saturated product was confirmed with X-ray crystallography. The observance of solely dimer product could come from the fact that the reaction was run at high concentration, 15 mM. Typical RCM were found to have concentration ranging from 1-5 mM.

Scheme 5: RCM attempt for construction of macrocycle

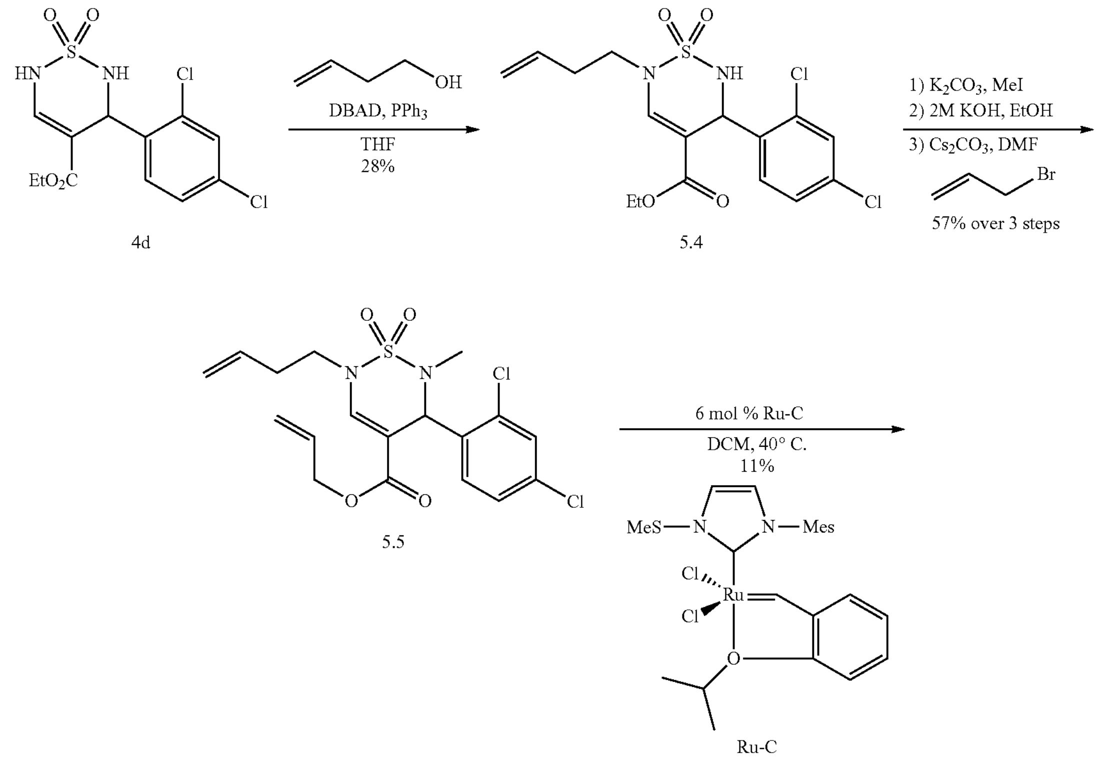

-continued

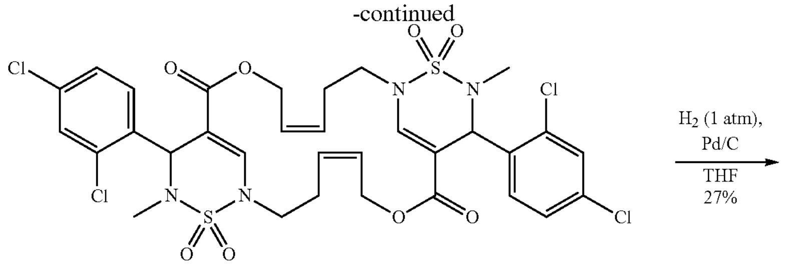

5.6

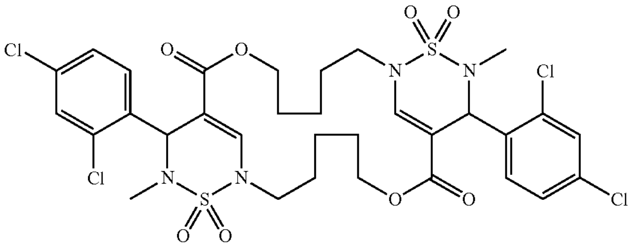

5.7

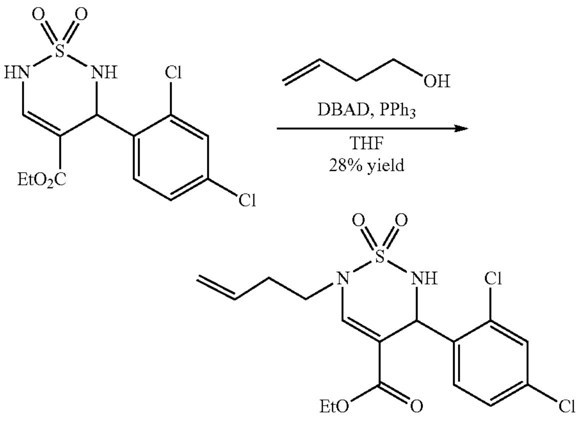

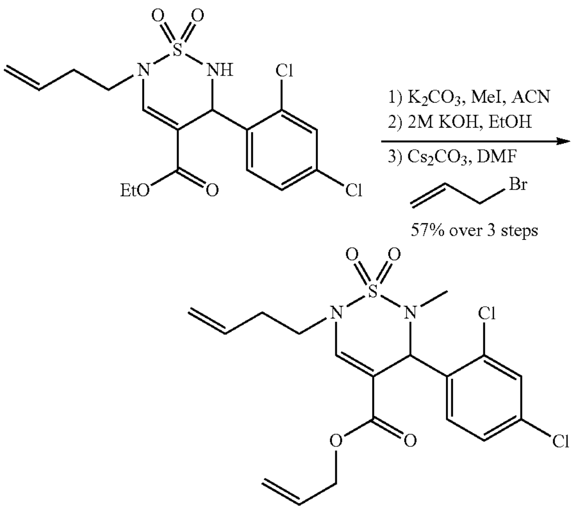

Ethyl 6-(but-3-en-1-yl)-3-(2,4-dichlorophenyl)-3,6-dihydro-2H-1,2,6-thiadiazine-4-carboxylate 1,1-dioxide (5.4): To a 0° C. solution of (4d) (4.0 g, 1.0 eq), and but-3-en-1-ol (1.27 g, 1.2 eq) in THF (63 mL) was added $PPh_3$ (3.6 g, 1.2 eq) and DBAD (3.2 g, 1.2 eq) portion wise (~5-6 addition). The solution was stirred at 0° C. for 1 hour and at rt for another 13 hours. The reaction was quenched with water (50 mL), transferred to a separatory funnel, and extracted with EtOAc (50 mL*3). The combined organic layers were washed with brine, dried over $MgSO_4$, filtered, concentrated and purified with chromatography to afford title compound as colorless oil. Yield: 28%.

Purification: Column 1: 100% DCM; $R_f$: 0.29; Stain: $KMnO_4$ then, Column 2: 15% EtOAc in PE; Stain: $KMnO_4$.

$^1H$ NMR (400 MHz; $CDCl_3$) δ 7.51 (1H, d, J=0.4 Hz), 7.45 (1H, d, J=2.0 Hz), 7.29-7.27 (1H, m, J=8.4 Hz, overlapping with $CDCl_3$), 7.22 (1H, dd, J=8.4 Hz), 5.91 (1H, d, J=8.0 Hz), 5.86-5.79 (1H, m), 5.24-5.19 (2H, m), 4.84 (1H, 8.0 Hz), 4.11-4.03 (2H, m), 3.76-3.63 (2H, m), 2.54 (2H, q, J=7.2 Hz), 1.11 (3H, t, J=7.2 Hz). $^{13}C$ NMR (100 MHz; $CDCl_3$) δ 164.8, 142.7, 135.1, 134.7, 133.8, 133.6, 130.6, 129.8, 127.1, 104.2, 60.8, 55.8, 49.9, 34.2, 14.2. HRMS $ESI^+$ m/z calcd for $C_{16}H_{19}O_4N_2Cl_2S$ $[M+H]^+$ 405.04371, found 405.04388.

Allyl 6-(but-3-en-1-yl)-3-(2,4-dichlorophenyl)-2-methyl-3,6-dihydro-2H-1,2,6-thiadiazine-4-carboxylate 1,1-dioxide (5.5): To a suspension of (5.4) (1.3 g, 1.0 eq) and $K_2CO_3$ (2.66 g, 6.0 eq) in ACN (50 mL, [rxn]=0.06 M) was added MeI (1.2 mL, 6.0 eq) in one portion. The reaction was left to stir at rt for 15 hours. Then, the mixture was filtered over a pad of celite. Eluent was concentrated and carried on. To the previous crude in EtOH (30 mL, [rxn]=0.1 M) was added 2M KOH solution (19 mL, 12 eq) in one portion. The solution was stirred at 80-85° C. for 5 hours. Upon completion, the reaction was cooled to rt, diluted with EtOAc and acidified with 4M HCl until pH=3. Aqueous phase was extracted with EtOAc (50 mL*3 mL). Organic phase was washed with brine, dried over $MgSO_4$, concentrated to afford orange foam. The orange foam was carried on as crude for next step. To the solution of the acid crude in DMF (32 mL, [rxn]=0.06 M) was added $Cs_2CO_3$ (1.35 g, 1.3 eq) and allyl bromide (0.33 mL, 1.2 eq). The reaction was left to stir at rt for 15 hours. Upon completion, the reaction was diluted with $H_2O$ (300 mL) and extracted with EtOAc (150 mL*3). Organic layers were washed with brine, dried over $MgSO_4$, concentrated, and purified with column chromatography to afford title compound as thick yellow oil. Yield: 57% over 3 steps.

Eluent: 0-20% EA in PE; $R_f$: 0.28; Stain: $KMnO_4$ $^1H$ NMR (400 MHz; $CDCl_3$) δ 7.58 (1H, s), 7.41 (1H, d, J=2.0 Hz), 7.20 (1H, d, J=8.4 Hz), 7.16 (1H, dd, J=2.0, 8.4 Hz), 5.82-5.76 (1H, m), 5.52 (1H, s), 5.22-5.09 (4H, m), 4.58-4.53 (2H, m), 3.68-3.64 (2H, m), 3.01 (3H, s), 2.52-2.51 (2H, m). $^{13}C$ NMR (100 MHz; $CDCl_3$) δ 165.1, 142.5, 135.0, 134.7, 134.0, 133.4, 132.0, 131.0, 129.5, 126.6, 119.0, 118.1, 99.9, 65.3, 63.4, 50.1, 40.0, 34.4. HRMS $ESI^+$ m/z calcd for $C_{18}H_{21}O_4N_2Cl_2S$ $[M+H]^+$ 431.5936 found 431.05881. IR (DCM) 3081, 2933, 2118,698, 1622, 1588, 1561.

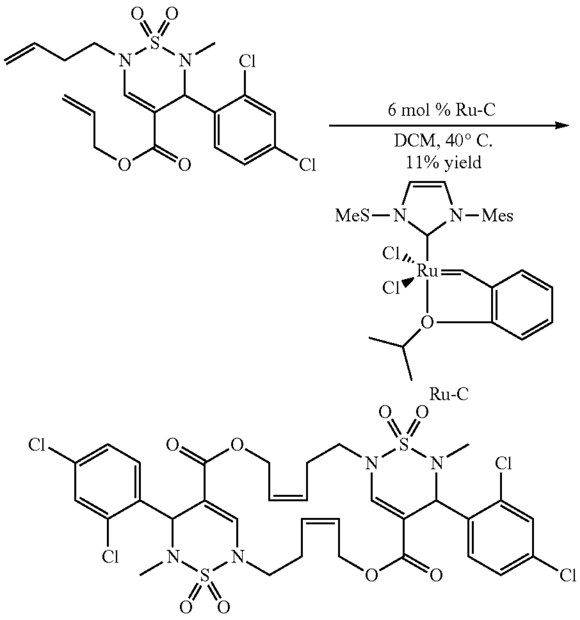

(4Z,9E,16Z,21E)-10,22-bis(2,4-dichlorophenyl)-11,23-dimethyl-7,19-dioxa-12,24-dithia-1,11,13,23-tetraazatricyclo[19.3.1.1$^{9,13}$]hexacosa-4,9(26),16.21(25)-tetraene-8,20-dione 12,12,24,24-tetraoxide (5.6): To a solution of (5.5) (802 mg, 1.0 equiv.) in DCM (125 mL, 0.015 M) was added Hoveyda-Grubbs second generation (74 mg, 6.0 mol %) at room temperature. The resulting green solution was degassed by freeze-pump-thaw and stirred at reflux for 11 hours. Reaction progress was done with TLC (eluent—15% EtOAc in hexane) which indicated complete consumption of starting material. The dark yellow solution was exposed to air for 1 hour, concentrated and purified with chromatography to afford title compound as light brown solid. Yield: 11%.

Eluent: 15-60% EtOAc in hexane; $R_f$: 0.10 in 50%; Stain: $KMnO_4$ $^1H$ NMR (500 MHz; $CDCl_3$) δ 7.44-7.42 (1H, s), 7.42 (1H, d, J=2.0 Hz), 7.18 (1H, d, J=8.0 Hz), 7.15 (1H, d, J=2.0 Hz), 5.74 (1H, td, J=5.0, 15 Hz), 5.54 (1H, s), 5.51-5.46 (1H, m), 4.79 (1H, dd, J=5.0, 14 Hz), 49 (1H, dd, J=3.5, 14 Hz), 3.79-3.74 (1H, m), 3.65-3.60 (1H, m), 3.61 (3H, s), 2.46 (2H, m). $^{13}C$ NMR (125 MHz; $CDCl_3$) δ 165.0, 143.2, 135, 134.2, 134.0, 131.1, 129.7, 129.4, 128.6, 126.7, 98.8, 64.5, 63.4, 50.5, 40.1, 32.9. HRMS $ESI^+$ m/z calcd for $C_{32}H_{33}O_8N_4Cl_4S_2$ $[M+H]^+$ 805.04884, found 805.04804. IR (neat) 2931, 1692, 1623 1588 1563.

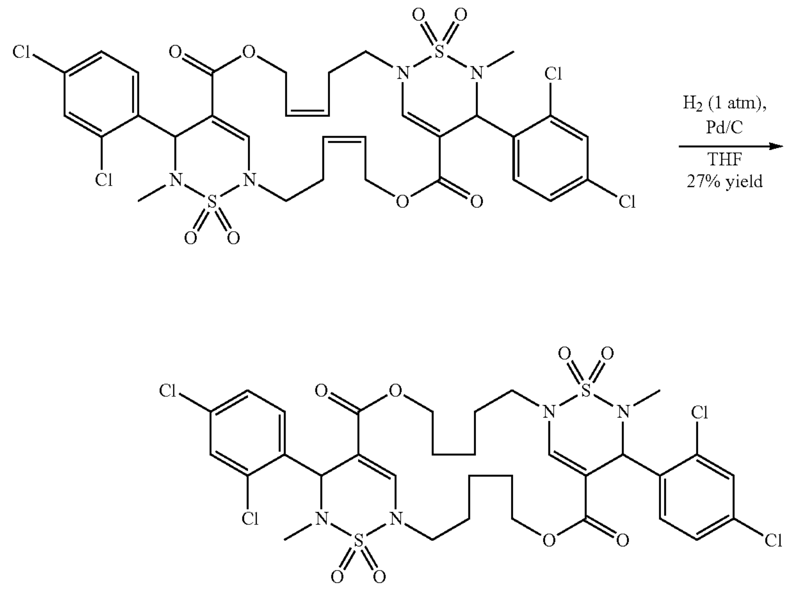

(9E,21E)-10,22-bis(2,4-dichlorophenyl)-11,23-dimethyl-7,19-dioxa-12,24-dithia-1,11,13,23-tetraazatricyclo [19.3.1.1$^{9,13}$]hexacosa-9(26),21(25)-diene-8,20-dione 12,12,24,24-tetraoxide (5.7): To a solution of Z isomer (5.6) (48 mg, 1.0 eq) in THF (4.0 mL, [rxn]=0.03 M) was added 10% Pd on C (24 mg, 0.1 eq) at rt under Na. The Na atmosphere was then replaced with $H_2$ from a double balloon, and the reaction mixture was stirred at rt for 15h. Reaction progress was done by TLC (eluent-50% EtOAc in hexane). Then, the reaction was filtered over a thin pad of celite. The eluent was concentrated to yield white solid. X-ray quality crystal was obtained from recrystallization with DCM. Yield: 27%.

$^1$H NMR (500 MHz; $CDCl_3$) δ 7.82 (1H, s), 7.63 (1H, d, J=2.0 Hz), 7.10-7.05 (2H, m), 5.47 (1H, s), 4.22-4.19 (1H, m), 4.06-4.02 (1H, m), 3.78-3.3.75 (2H, m), 2.92 (3H, s), 1.69-1.60 (1H, m), 1.51-1.46 (1H, m). $^{13}$C NMR (125 MHz; $CDCl_3$) δ 164.7, 143.1, 134.7, 134.3, 133.3, 131.4, 128.7, 126.6, 98.3, 64.0, 62.8, 54.9, 50.9, 29.5, 28.1, 23.0. HRMS ESI$^-$ m/z calcd for $C_{32}H_{37}O_8N_4C_{14}S_2$ $[M-H]^+$ 809.08014, found 809.08082.

Figure 5:
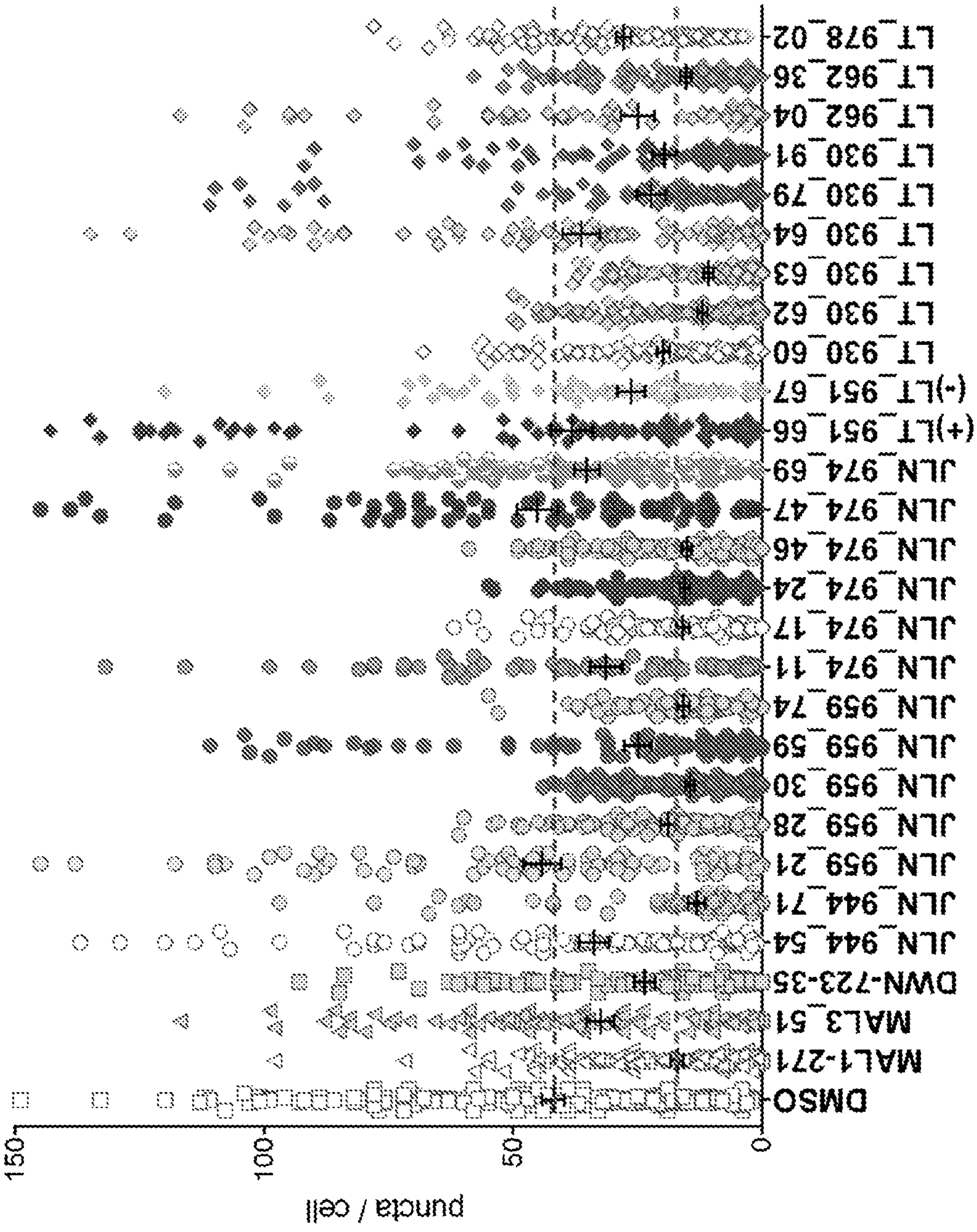
FIG. 5 is a graph showing the statistical significance between DMSO and specific compounds (10 μM) on HEK293H cells transfected with HTT17Q-mCherry (pCAG 17Q HTT-N548) treated for 6 h.
Figure 6:
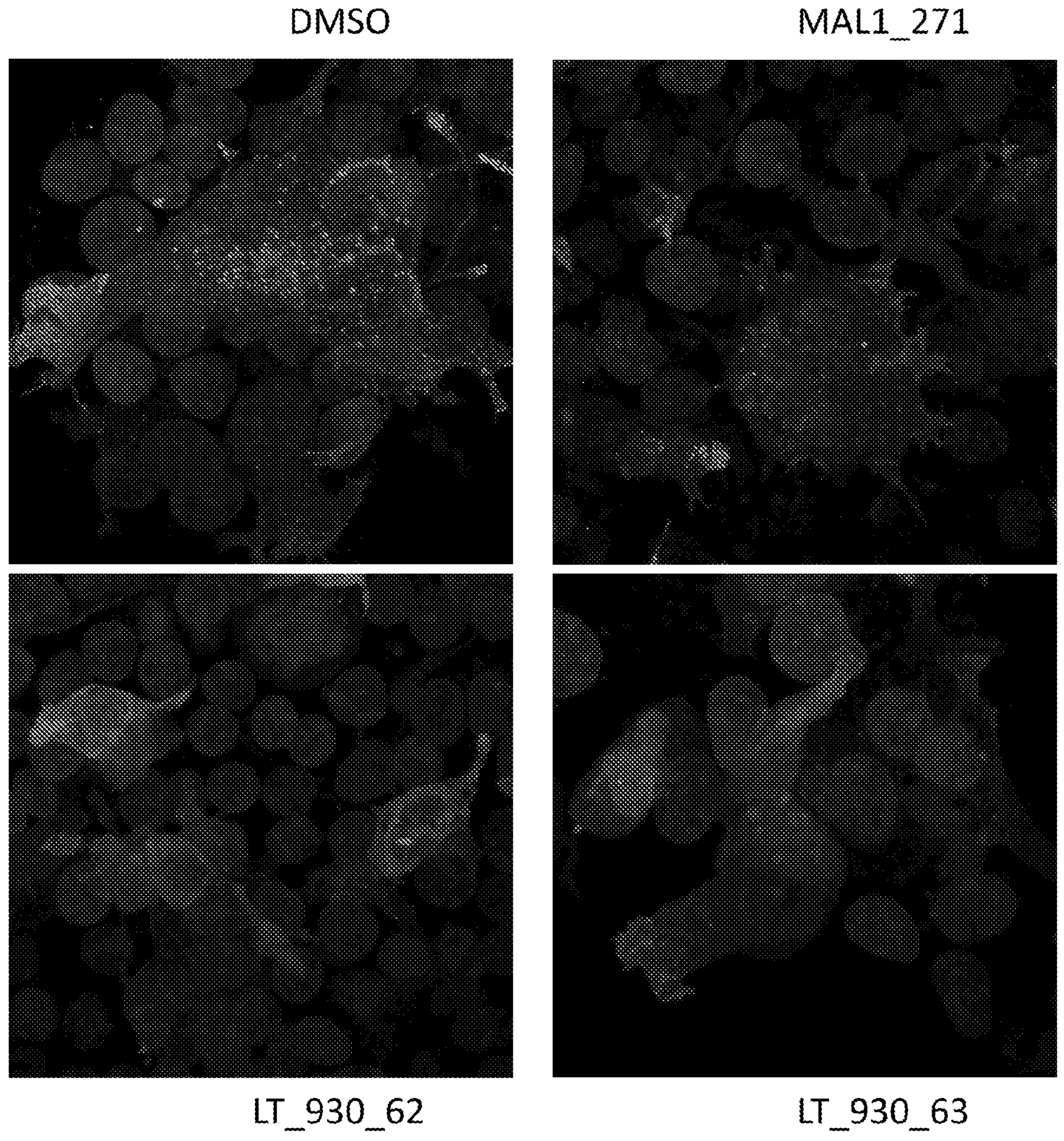
FIG. 6 shows images of HEK293H cells transfected with HTT17Q-mCherry (pCAG 17Q HTT-N548) and treated with DMSO or MAL1-271, LT_930_62, and LT_930_63 (10 μM) for 6 h.
Figure 7:
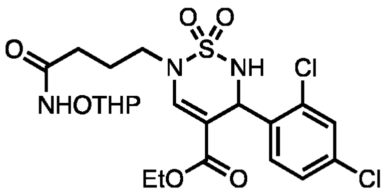
FIG. 7 shows structures of thiadiazine 1,1-dioxide analogs or derivatives thereof that were synthesized.
Figure 7:
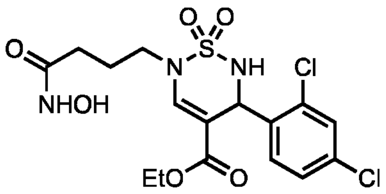
Figure 7:
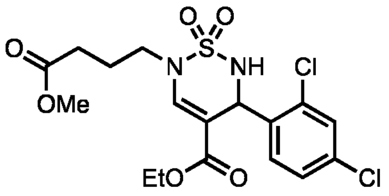
Figure 7:
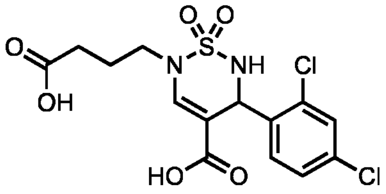
Figure 7:
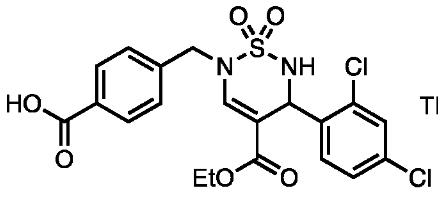
Figure 7:
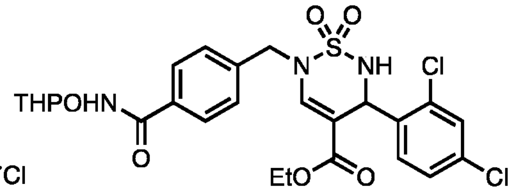
Figure 7:
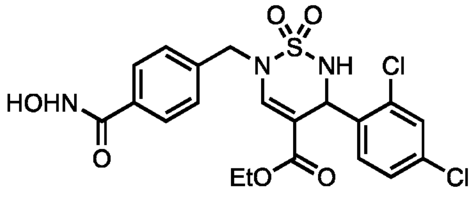
Figure 7:
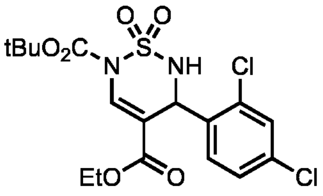
Figure 7:
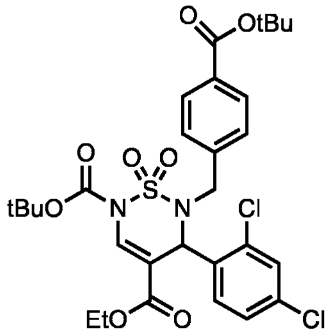
Figure 7:
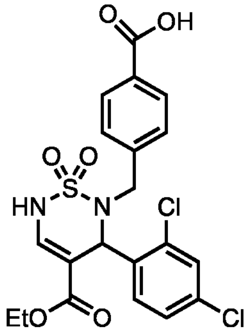
Figure 8:
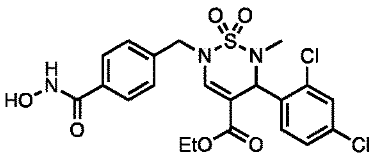
FIG. 8 shows structures of thiadiazine 1,1-dioxide analogs or derivatives thereof that were synthesized.
Figure 8:
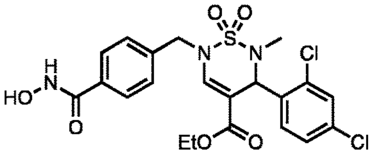
Figure 8:
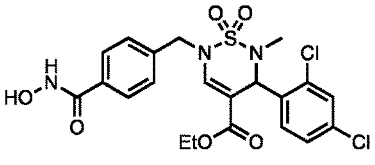
Figure 8:
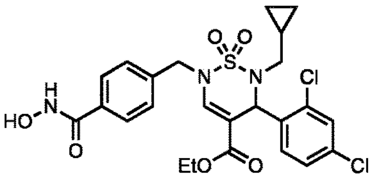
Figure 8:
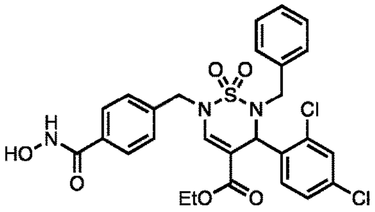
Figure 8:
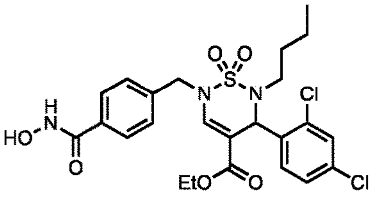
Figure 8:
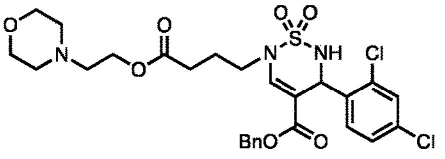
Figure 8:
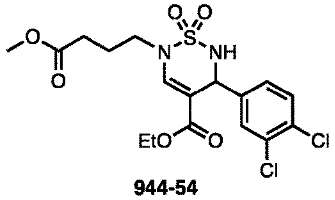
Figure 8:
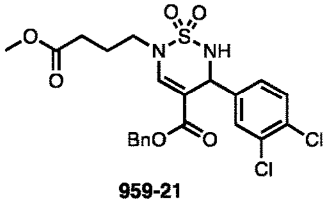
Figure 9:
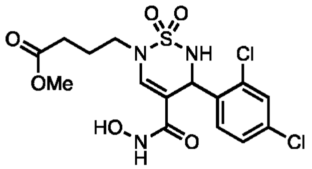
FIG. 9 shows structures of thiadiazine 1,1-dioxide analogs or derivatives thereof that were synthesized.
Figure 9:
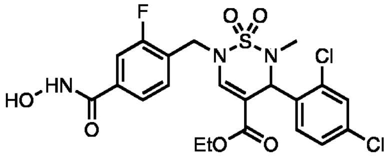
Figure 9:
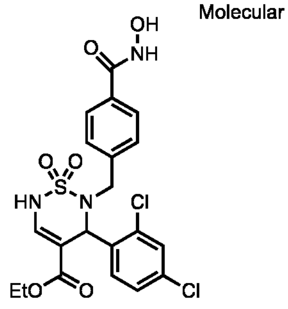
Figure 9:
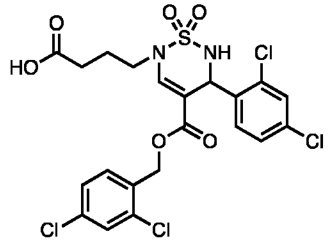
Figure 9:
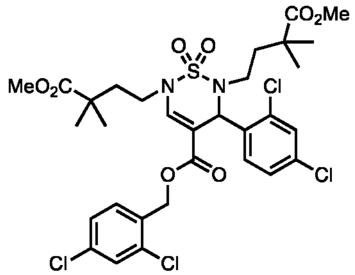
Figure 9:
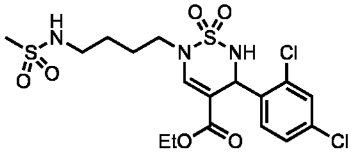
Figure 9:
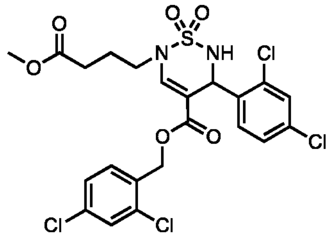
Figure 9:
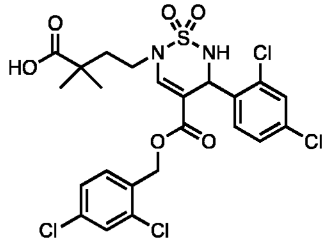
Figure 10:
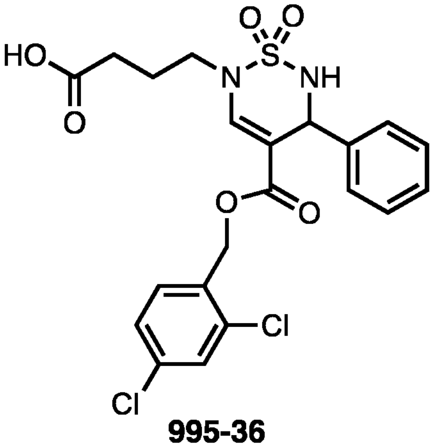
FIG. 10 shows structures of thiadiazine 1,1-dioxide analogs or derivatives thereof that were synthesized.
Figure 10:
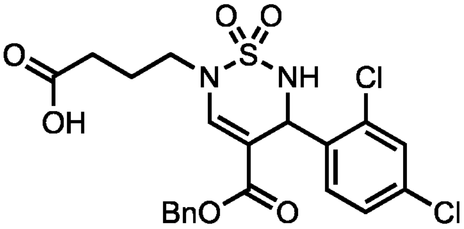
Figure 10:
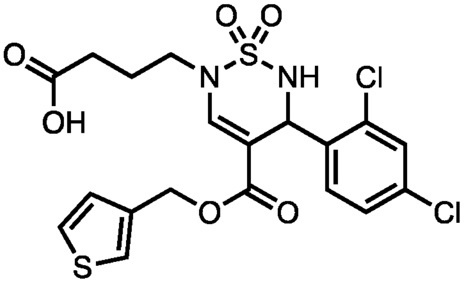
Figure 10:
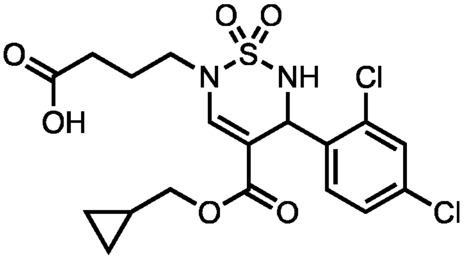
Figure 10:
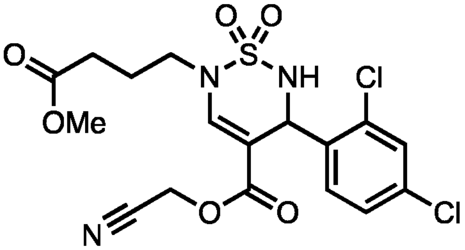
Figure 10:
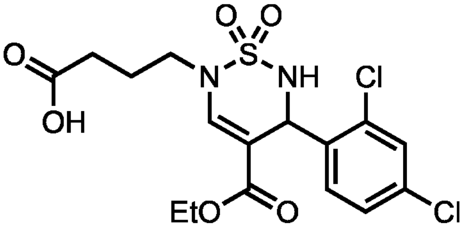
Figure 10:
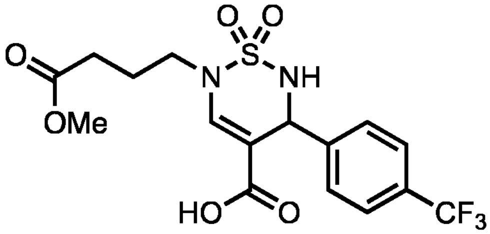
Figure 10:
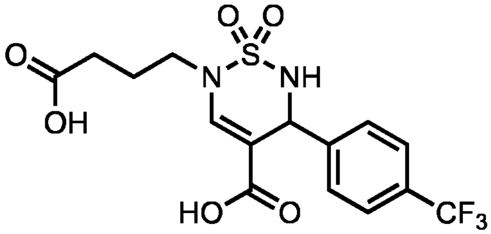

Results: Several analogs (10 μM) reduced the number of cellular puncta/aggregates compared to the DMSO control. See FIG. 5. Cells were stained for confocal microscope imaging with 4',6-diamidino-2-phenylindole (DAPI) and bright spot detection tool was used to identify and quantify the number of protein aggregates ("dots") per cell. See FIG. 6. Compared to the MAL1-271 positive control, most compounds were equally effective (Tables 8 and 9) while compounds 930-62 and 930-63 were more effective.

TABLE 8

Comparison of the effectiveness of the compounds to blunt formation of toxic aggregates in HEK293 cells that express an HTT17polyQ compared to DMSO.

| Compound | Effectiveness compared to DMSO | |
|---|---|---|
| MAL1-271 | **** | <0.0001 |
| MAL3_51 | * | 0.0201 |
| 723-35 | **** | <0.0001 |
| 944_54 | ns | 0.1661 |
| 944_71 | **** | <0.0001 |
| 959_21 | ns | >0.9999 |
| 959_28 | **** | <0.0001 |
| 959_30 | **** | <0.0001 |
| 959_59 | **** | <0.0001 |
| 959_74 | **** | <0.0001 |
| 974_11 | * | 0.0201 |
| 974_17 | **** | <0.0001 |
| 974_24 | **** | <0.0001 |
| 974_46 | **** | <0.0001 |
| 974_47 | ns | >0.9999 |
| 974_69 | ns | >0.9999 |
| (+)-951_66 | ns | 0.0691 |
| (−)-951_67 | **** | <0.0001 |
| 930_60 | **** | <0.0001 |
| 930_62 | **** | <0.0001 |
| 930_63 | **** | <0.0001 |
| 930_64 | ns | 0.3501 |
| 930_79 | **** | <0.0001 |
| 930_91 | **** | <0.0001 |
| 962_04 | **** | <0.0001 |
| 962_36 | **** | <0.0001 |
| 978_02 | ns | 0.7014 |

ns refers to data not shown.

TABLE 9

Comparison of the effectiveness of the compounds to blunt formation of toxic aggregates in HEK293 cells that express an HTT17polyQ compared to MAL1-271.

| Compound | Effectiveness compared to MAL1-271 | | |
|---|---|---|---|
| MAL3_51 | *** | 0.0002 | Less |
| 723-35 | ns | 0.1307 | Similar |
| 944_54 | **** | <0.0001 | Less |
| 944_71 | ns | 0.3463 | Similar |
| 959_21 | **** | <0.0001 | Less |
| 959_28 | ns | >0.9999 | Similar |
| 959_30 | ns | 0.0997 | Similar |
| 959_59 | ns | >0.9999 | Similar |
| 959_74 | ns | >0.9999 | Similar |
| 974_11 | ** | 0.0046 | Less |
| 974_17 | ns | >0.9999 | Similar |
| 974_24 | ns | >0.9999 | Similar |
| 974_46 | ns | >0.9999 | Similar |
| 974_47 | **** | <0.0001 | Less |
| 974_69 | **** | <0.0001 | Less |
| (+)-951_66 | *** | 0.0002 | Less |
| (−)-951_67 | ns | 0.2145 | Similar |
| 930_60 | ns | 0.7152 | Similar |
| 930_62 | * | 0.0487 | More |
| 930_63 | * | 0.0377 | More |
| 930_64 | **** | <0.0001 | Less |
| 930_79 | ns | >0.9999 | Similar |
| 930_91 | ns | >0.9999 | Similar |
| 962_04 | ns | >0.9999 | Similar |
| 962_36 | ns | >0.9999 | Similar |
| 978_02 | **** | <0.0001 | Less |

ns refers to data not shown.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A thiadiazine compound having a structure according to Formula I-A,

Formula I-A

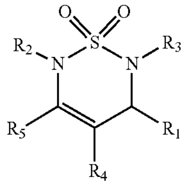

wherein $R_1$ is selected from aryl or heteroaryl, wherein $R_1$ is substituted with two or more halogens;

$R_2$ is selected from H, —R'$CO_2$H, —R'$CO_2$R", —R'$CONH_2$, —R'CONHR", —R'CONR'"R'", —R'CONHOH, —and —R'$NHSO_2$R", wherein R' is selected from $C_1$-$C_6$ alkyl and alkylaryl, and R", and R'" are independently selected from $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkylcycloalkyl, cycloalkenyl, cycloheteroalkyl, alkylcycloheteroalkyl, cycloheteroalkenyl, aryl, and heteroaryl, wherein R', R", and R'" are independently optionally substituted with one or more groups selected from halogen, hydroxyl, amino, or alkyl;

$R_3$ is selected from H, alkyl, alkylcycloalkyl, alkylaryl, alkylheteroaryl, —R'$CO_2$H, —R'$CO_2$R", —R'$CONH_2$, —R'CONHR", —R'CONR"R'", and —R'CONHOH, wherein R' is selected from $C_1$-$C_6$ alkyl, $C_2$-$C_6$ alkenyl, cycloalkyl, cycloalkenyl, cycloheteroalkyl, $C_1$-$C_6$ alkyl cycloalkyl, $C_1$-$C_6$ alkyl cycloheteroalkyl, $C_1$-$C_6$ alkyl-cycloalkenyl, aryl, $C_1$-$C_6$ alkylaryl, heteroaryl, and $C_1$-$C_6$ alkyl heteroaryl, and R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, cycloalkenyl, alkylcycloalkenyl, cycloheteroalkyl, aryl, and heteroaryl, wherein R', R", and R'" are independently optionally substituted with one or more groups selected from halogen, hydroxyl, carboxyl, amino, or alkyl;

$R_4$ is selected from —$CO_2$H, or —$CO_2$R", wherein R" is selected from hydrogen, $C_1$-$C_6$ alkyl, aryl, and alkylaryl; and $R_5$ is H;

wherein when $R_2$ is H, $R_3$ is not H.

2. The compound of claim 1, wherein $R_1$ is dichlorophenyl.

3. The compound of claim 1, wherein $R_2$ is selected from H, —$(CH_2)_3CO_2Me$, —$(CH_2)_3C(O)NHOH$, and

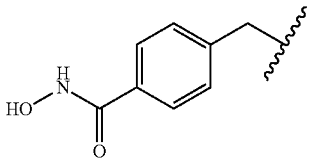 [SMILES: *Cc1ccc(C(=O)NO)cc1]

4. The compound of claim 1, wherein $R_2$ is not H.

5. The compound of claim 1, wherein $R_3$ is selected from H, $C_1$-$C_6$ alkyl, alkylcycloalkyl, and alkylaryl; optionally substituted with one or more groups selected from halogen, hydroxyl, carboxyl, and amino.

6. The compound of claim 1, wherein $R_3$ is selected from H, —$CH_3$,

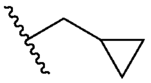, and 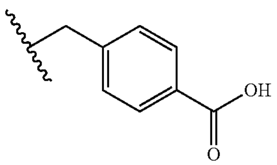

7. The compound of claim 1, wherein $R_3$ is not H.

8. The compound of claim 1, wherein $R_4$ is selected from —$CO_2$H or —$CO_2$R", and R" is —$CH_2CH_3$.

9. The compound of claim 1, wherein the compound has the following structure:

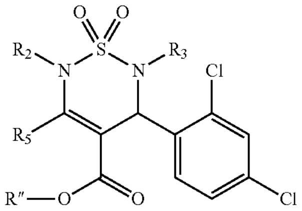

wherein

R" is selected from H and $C_1$-$C_6$ alkyl.

10. The compound of claim 1, having a structure below:

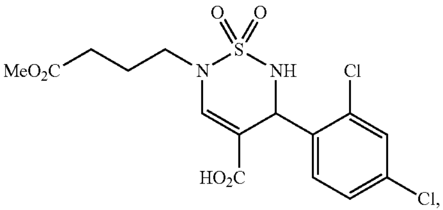,

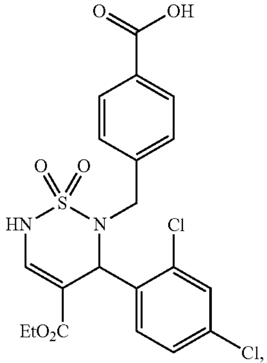,

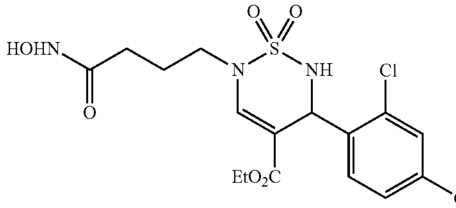,

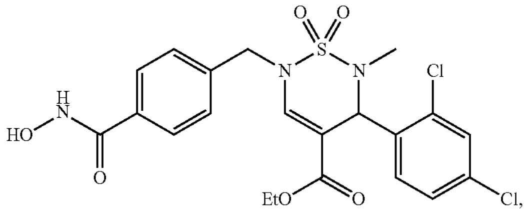, or

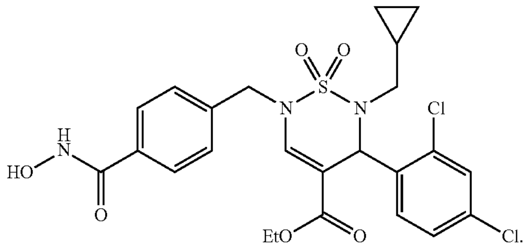.

11. The compound of claim 1, having a structure below:

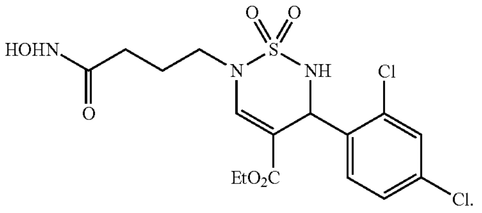

12. A pharmaceutical composition comprising a therapeutic effective amount of the compound of claim 1, and a pharmaceutically acceptable carrier.

13. A method of preparing the thiadiazine compound of claim 1, the method comprising:

a) condensing sulfamide with a 3,3-dialkoxypropionate to form a cyclic dimer;

b) condensing the cyclic dimer with an aldehyde, RICHO, to form a thiadiazine 1,1-dioxide core, and c) sequentially N-alkylating the thiadiazine 1,1-dioxide core to form the thiadiazine-1,1-dioxide compound.

* * * * *